(12) United States Patent
Seydoux et al.

(10) Patent No.: US 8,736,270 B2
(45) Date of Patent: May 27, 2014

(54) LOOK AHEAD LOGGING SYSTEM

(75) Inventors: Jean Seydoux, Houston, TX (US); Emmanuel Legendre, Houston, TX (US); Reza Taherian, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 667 days.

(21) Appl. No.: 12/674,366

(22) PCT Filed: Aug. 22, 2008

(86) PCT No.: PCT/US2008/074007
§ 371 (c)(1),
(2), (4) Date: Feb. 19, 2010

(87) PCT Pub. No.: WO2009/029517
PCT Pub. Date: Mar. 5, 2009

(65) Prior Publication Data
US 2011/0133740 A1 Jun. 9, 2011

Related U.S. Application Data

(63) Continuation-in-part of application No. 11/952,302, filed on Dec. 7, 2007, now Pat. No. 7,755,361, which is a continuation-in-part of application No. 11/160,533, filed on Jun. 28, 2005, now Pat. No. 7,786,733.

(60) Provisional application No. 60/968,275, filed on Aug. 27, 2007, provisional application No. 60/587,689, filed on Jul. 14, 2004.

(51) Int. Cl.
*G01V 3/00* (2006.01)

(52) U.S. Cl.
USPC ........... 324/338; 324/323; 324/324; 324/329; 324/331; 324/333

(58) Field of Classification Search
CPC ............... G01V 1/00; H01Q 1/00; E21B 1/00
USPC .......................... 324/331, 333–376, 323–329
See application file for complete search history.

(56) References Cited

U.S. PATENT DOCUMENTS 2,507,351 A * 5/1950 Scherbatskoy ............. 340/854.6
3,286,163 A * 11/1966 Holser et al. .................. 324/338
(Continued)

FOREIGN PATENT DOCUMENTS

CN 1559011 A 12/2004
CN 1648691 A 8/2005
(Continued)

OTHER PUBLICATIONS

Barkved et al. ("Valhall Field-Still on Plateau after 20 Years of Production", Society of Petroleum Engineers Inc. 2003), see attached document.*

(Continued)

*Primary Examiner* — Huy Q Phan
*Assistant Examiner* — Temilade S Rhodes-Vivour
(74) *Attorney, Agent, or Firm* — Kenneth Liu

(57) ABSTRACT

A technique utilizes the acquisition of data from desired subterranean regions via a logging system. The logging system is constructed for use in a wellbore and comprises a transmitter module having a transmitter antenna. Additionally, the logging system utilizes a receiver module spaced from the transmitter module and having a receiver antenna. The transmitter antenna and the receiver antenna are oriented to enable sensitivity in desired directions, such as ahead of the logging system.

29 Claims, 49 Drawing Sheets

(56) References Cited

U.S. PATENT DOCUMENTS

| | | | |
|---|---|---|---|
| 3,808,520 A * | 4/1974 | Runge | 324/343 |
| 4,697,190 A * | 9/1987 | Oswald | 343/719 |
| 4,716,973 A * | 1/1988 | Cobern | 175/50 |
| 4,739,325 A | 4/1988 | MacLeod | |
| 4,810,970 A * | 3/1989 | Warren et al. | 324/338 |
| 5,117,927 A | 6/1992 | Askew | |
| 5,157,605 A | 10/1992 | Chandler et al. | |
| 5,355,088 A * | 10/1994 | Howard, Jr. | 324/339 |
| 5,508,616 A | 4/1996 | Sato et al. | |
| 5,530,359 A * | 6/1996 | Habashy et al. | 324/338 |
| 5,661,402 A | 8/1997 | Chesnutt et al. | |
| 5,854,991 A * | 12/1998 | Gupta et al. | 702/7 |
| 5,955,884 A | 9/1999 | Payton et al. | |
| 6,057,784 A | 5/2000 | Schaaf et al. | |
| 6,163,155 A | 12/2000 | Bittar | |
| 6,181,138 B1 | 1/2001 | Hagiwara et al. | |
| 6,188,222 B1 | 2/2001 | Seydoux et al. | |
| 6,294,917 B1 | 9/2001 | Nichols | |
| 6,297,639 B1 | 10/2001 | Clark et al. | |
| 6,304,086 B1 | 10/2001 | Minerbo et al. | |
| 6,476,609 B1 | 11/2002 | Bittar | |
| 6,480,000 B1 | 11/2002 | Kong et al. | |
| 6,525,540 B1 | 2/2003 | Kong et al. | |
| 6,541,979 B2 | 4/2003 | Omeragic | |
| 6,556,014 B1 | 4/2003 | Kong et al. | |
| 6,556,015 B1 | 4/2003 | Omeragic et al. | |
| 6,594,584 B1 | 7/2003 | Omeragic et al. | |
| 6,646,441 B2 | 11/2003 | Thompson et al. | |
| 6,656,014 B2 | 12/2003 | Aulson | |
| 6,794,875 B2 | 9/2004 | Strickland | |
| 6,911,824 B2 | 6/2005 | Bittar | |
| 6,937,021 B2 * | 8/2005 | Rosthal | 324/339 |
| 6,952,101 B2 * | 10/2005 | Gupta | 324/339 |
| 6,958,610 B2 | 10/2005 | Gianzero | |
| 6,969,994 B2 * | 11/2005 | Minerbo et al. | 324/343 |
| 6,998,844 B2 | 2/2006 | Omeragic et al. | |
| 6,998,884 B2 | 2/2006 | Ng et al. | |
| 7,019,528 B2 | 3/2006 | Bittar | |
| 7,093,672 B2 | 8/2006 | Seydoux et al. | |
| 7,612,565 B2 | 11/2009 | Seydoux et al. | |
| 7,656,160 B2 | 2/2010 | Legendre et al. | |
| 7,786,733 B2 | 8/2010 | Seydoux et al. | |
| 7,924,013 B2 | 4/2011 | Seydoux et al. | |
| 8,466,683 B2 | 6/2013 | Legendre et al. | |
| 2003/0016020 A1 | 1/2003 | Gianzero | |
| 2003/0076107 A1 * | 4/2003 | Fanini et al. | 324/339 |
| 2003/0085707 A1 | 5/2003 | Minerbo et al. | |
| 2003/0184302 A1 * | 10/2003 | Omeragic et al. | 324/338 |
| 2003/0184303 A1 * | 10/2003 | Homan et al. | 324/338 |
| 2004/0017197 A1 * | 1/2004 | Chen et al. | 324/343 |
| 2004/0108853 A1 * | 6/2004 | Rosthal | 324/343 |
| 2004/0113609 A1 * | 6/2004 | Homan et al. | 324/202 |
| 2004/0140809 A1 * | 7/2004 | Mercer | 324/326 |
| 2004/0183538 A1 | 9/2004 | Hanstein et al. | |
| 2005/0140373 A1 | 6/2005 | Li et al. | |
| 2006/0011385 A1 | 1/2006 | Seydoux et al. | |
| 2006/0033502 A1 | 2/2006 | Bittar | |
| 2006/0038571 A1 * | 2/2006 | Ostermeier et al. | 324/338 |
| 2008/0143336 A1 * | 6/2008 | Legendre et al. | 324/339 |
| 2009/0015261 A1 | 1/2009 | Yang et al. | |
| 2009/0302851 A1 | 12/2009 | Bittar et al. | |
| 2011/0238220 A1 | 9/2011 | Seydoux et al. | |

FOREIGN PATENT DOCUMENTS

| | | |
|---|---|---|
| EP | 12009 A2 | 6/1980 |
| RU | 2069878 C1 | 11/1996 |
| RU | 2107313 C1 | 3/1998 |
| SU | 817648 A1 | 3/1981 |
| SU | 960701 A1 | 9/1982 |
| SU | 998995 A1 | 2/1983 |
| SU | 1004940 A1 | 3/1983 |
| SU | 1246035 A1 | 7/1986 |

OTHER PUBLICATIONS

First Office Action of Chinese Patent Application No. 200880113518.9 dated Jun. 21, 2012.

"Double Electromagnetic and Lateral Logging", Methodical Handbook, Moscow, Nedra, Russia, 1991.

Bonner, et al., "A New Generation of Electrode Resistivity Measurements for Formation Evaluation while Drilling", SPWLA 35th Annual Logging Symposium, Paper OO, 1994, pp. 1-25.

Korolev, et al., "Electromagnetic Logging by a Lateral Magnetic Dipole, Perspectives of Electromagnetic Well Scanning", Geofizika Scientific-Production Co. Russia, 1995.

Machetin, et al., "Temp—a New Dual-Electromagnetic and Laterology Apparatus-Tech. Complex", 13th European Formation Evaluation Sym. Trans., Budapest Ch. SPWLA, Paper K, 1990.

\* cited by examiner

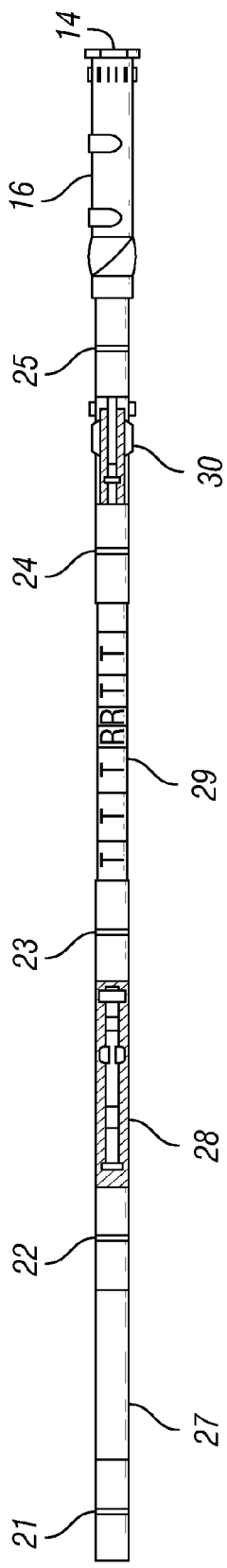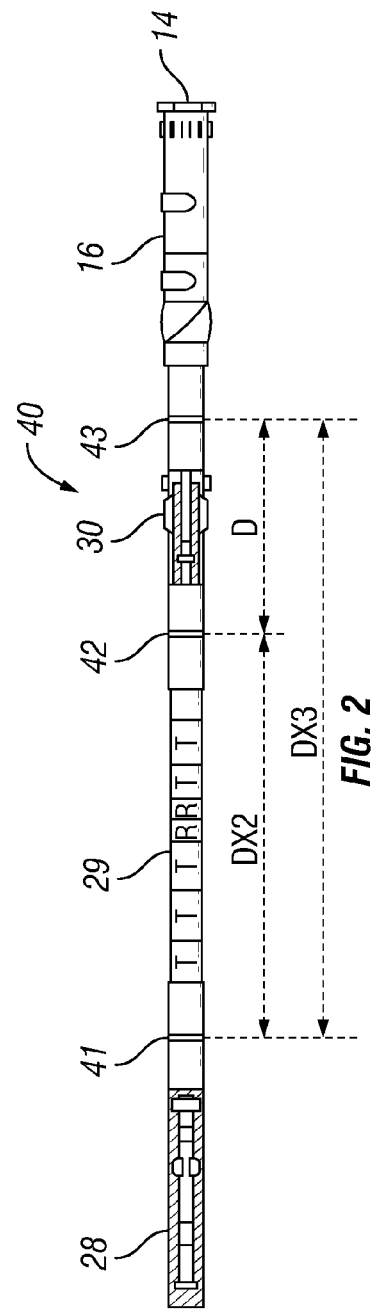
FIG. 1
FIG. 2

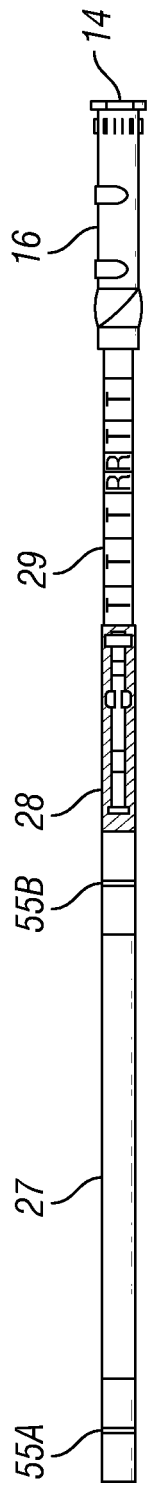
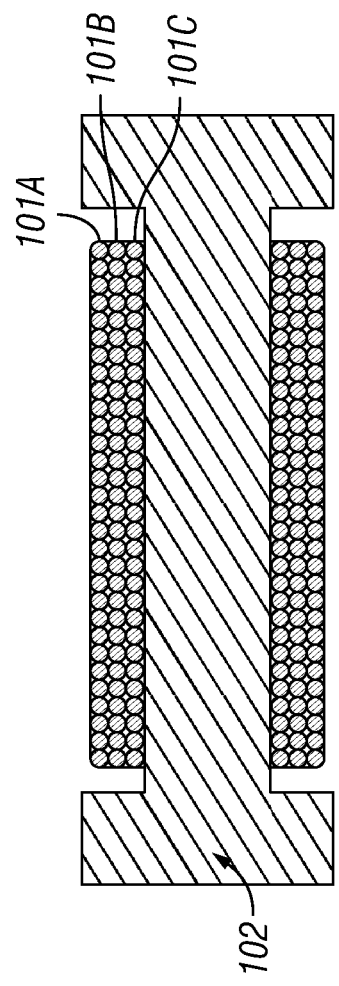
FIG. 8
FIG. 9

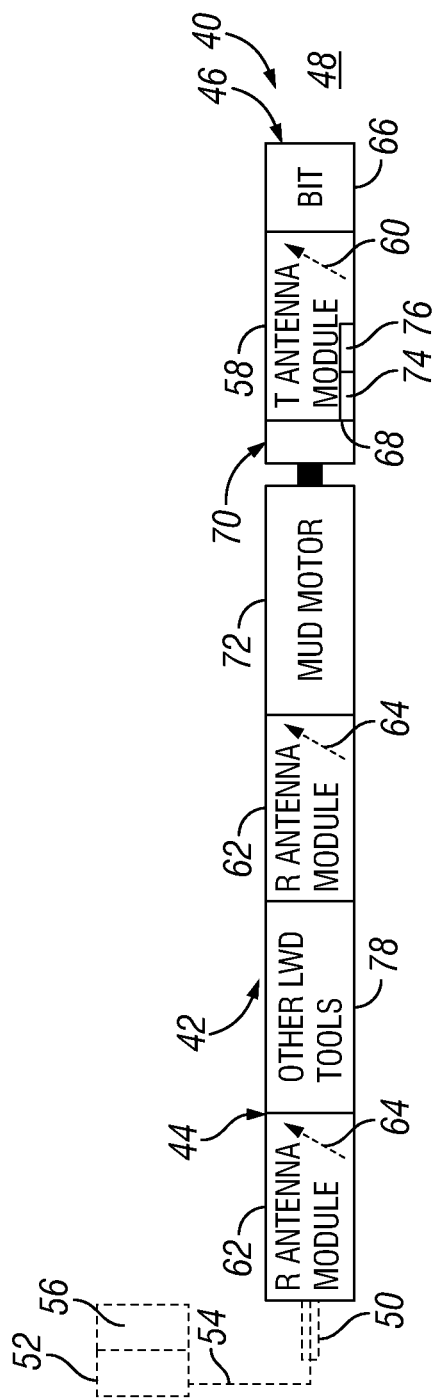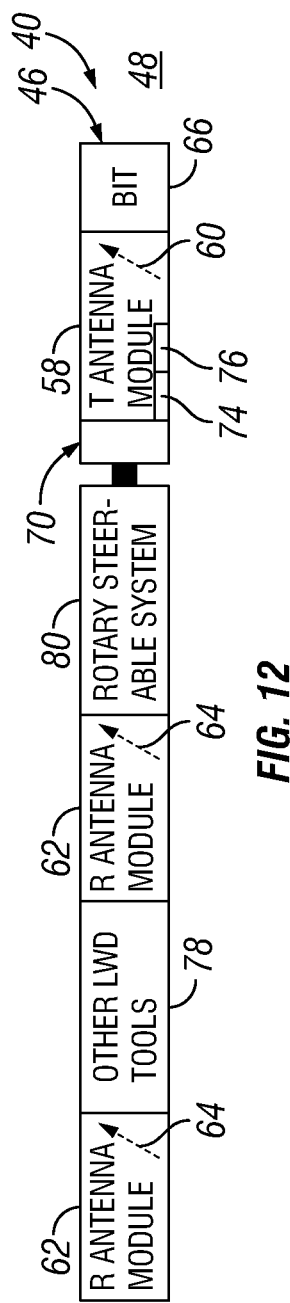
FIG. 11
FIG. 12

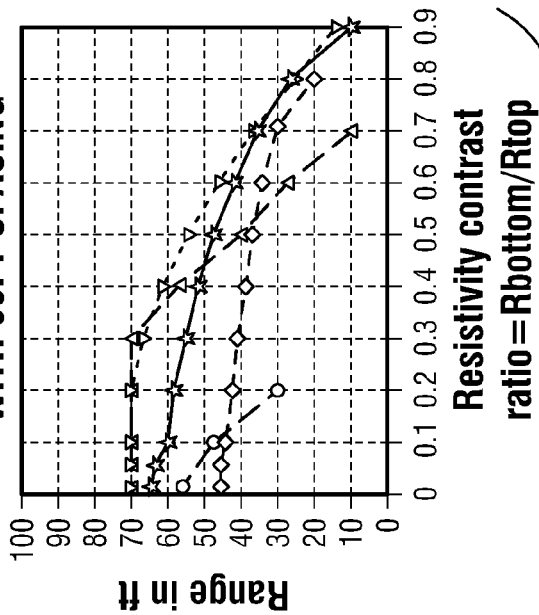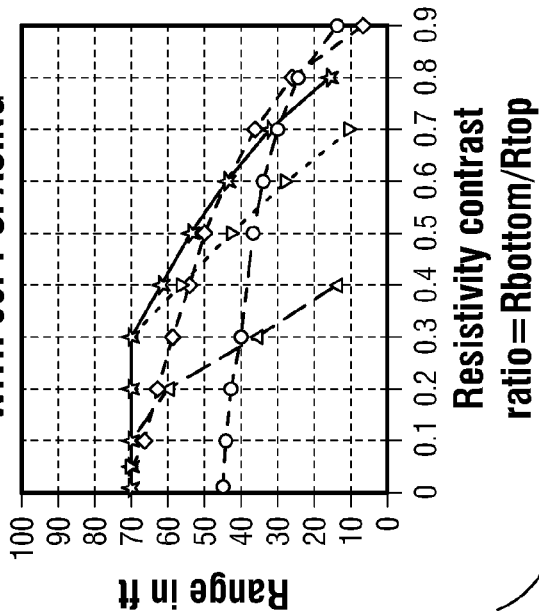
FIG. 32

LOOK AHEAD LOGGING SYSTEM

CROSS-REFERENCE TO RELATED APPLICATIONS

The present application is a U.S. National Stage application filed under 35 U.S.C. §371 based upon PCT International Application No. PCT/US08/74007 filed on Aug. 22, 2008, which claims priority to U.S. Provisional Patent Application No. 60/968,275, filed on Aug. 27, 2007. The present application is also a continuation-in-part of U.S. patent application Ser. No. 11/952,302, filed on Dec. 7, 2007 and now issued as U.S. Pat. No. 7,755,361, which is a continuation-in-part of U.S. patent application Ser. No. 11/160,533, filed on Jun. 28, 2005, now issued as U.S. Pat. No. 7,786,733, which claims priority to U.S. Provisional Patent Application No. 60/587,689. All of the applications referenced in this paragraph are incorporated by reference herein in their entireties.

BACKGROUND

In various well related operations, logging is performed to obtain information related to the subterranean environment in which a wellbore is formed. A logging tool is deployed downhole into the wellbore with a variety of sensors to obtain data helpful in understanding and utilizing the well. In some applications, logging-while-drilling techniques are used to obtain data while a wellbore is drilled. However, existing logging systems can be limited in their ability to obtain information from certain regions of the subterranean environment, such as regions forward or ahead of the logging system.

SUMMARY

In general, the present invention provides a system and method for acquiring data from desired subterranean regions via a logging system. The logging system is constructed for use in a wellbore and utilizes a transmitter module having a transmitter antenna. Additionally, the logging system comprises a receiver module having a receiver antenna, and the receiver module is spaced from the transmitter module. The transmitter antenna and the receiver antenna are oriented to enable sensitivity in desired directions, such as ahead of the logging system.

BRIEF DESCRIPTION OF THE DRAWINGS

Certain embodiments of the invention will hereafter be described with reference to the accompanying drawings, wherein like reference numerals denote like elements, and:

FIG. 1 shows a resistivity array according to an embodiment of the present invention;

FIG. 2 shows a resistivity array according to another embodiment of the present invention;

FIG. 8 shows a resistivity array according to an embodiment of the present invention;

FIG. 9 shows an antenna module according to an embodiment of the present invention;

FIG. 11 is a schematic illustration of a logging system for obtaining data related to a subterranean environment, according to an embodiment of the present invention;

FIG. 12 is a schematic illustration similar to that of FIG. 11 but showing another example of the system, according to an alternate embodiment of the present invention;

FIG. 32 is a graphical representation related to an example of the logging system regarding attenuation range sensitivity with respect to resistivity levels and contrast for a step down formation resistivity profile at two different transmission frequencies, according to an embodiment of the present invention;

DETAILED DESCRIPTION

Figure 3:
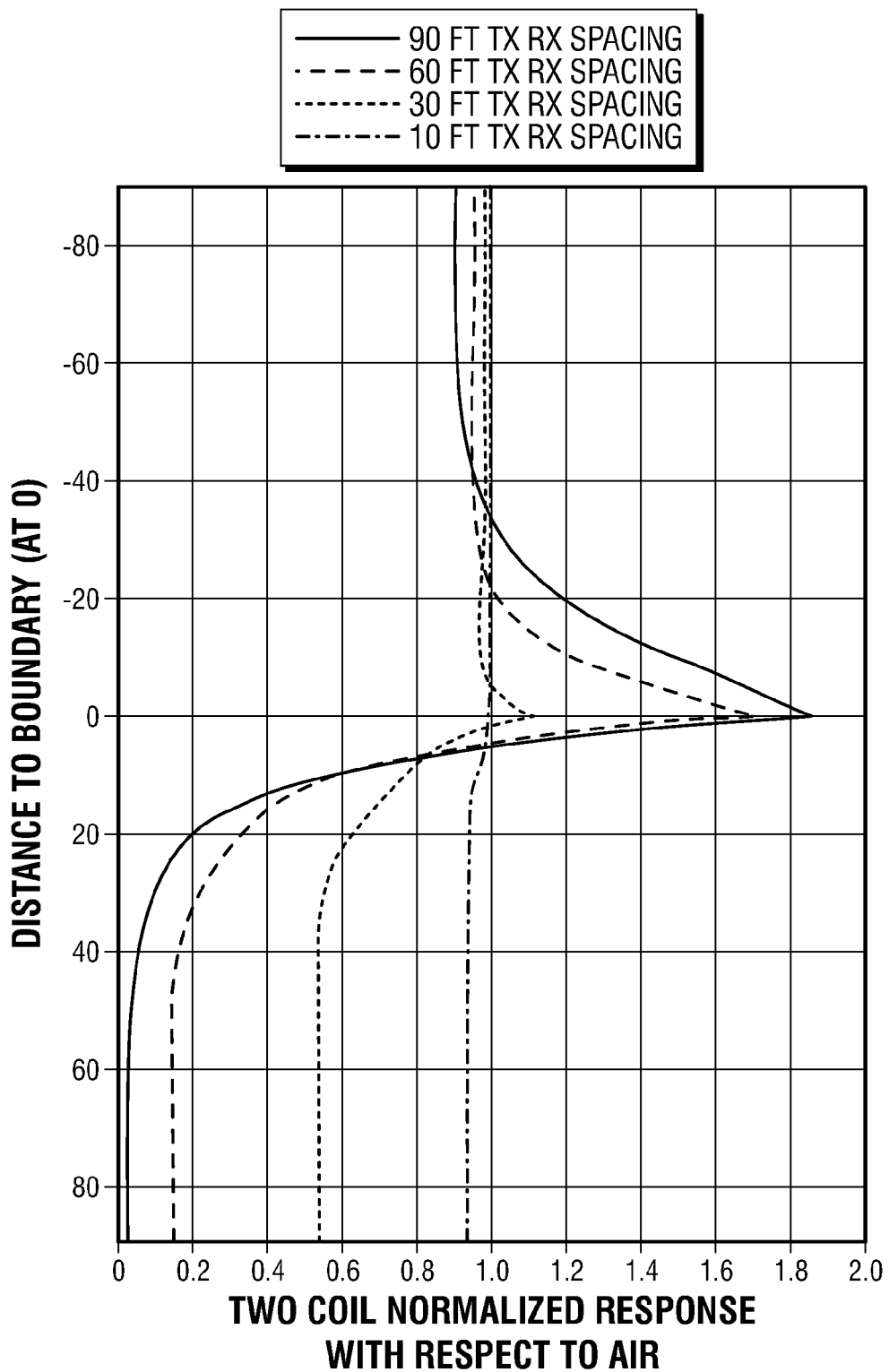
FIG. 3 shows examples of depth of investigation for a 10 kHz amplitude measurement obtained with various transmitter-receiver distances according to an embodiment of the present invention.

In the following description, numerous details are set forth to provide an understanding of the present invention. However, it will be understood by those of ordinary skill in the art that the present invention may be practiced without these details and that numerous variations or modifications from the described embodiments may be possible.

Embodiments of the invention relate to resistivity arrays having improved properties. Some embodiments of the invention relate to methods of using these tools in formation evaluation. Embodiments of the invention may permit inversion for more complicated formation models (i.e., formation model with more parameters) and/or may improve the robustness of resistivity measurement inversion (uncertainty reduction). Some embodiments of the invention may increase the flexibility of formation resistivity evaluation by providing more measurements, each of which may have different responses to different formation models.

Some embodiments of the invention provide resistivity arrays having a modular design. The modular design facilitates setting up different tool configurations for different measurement requirements. For example, by extending the number of transmitter, receiver combinations (for example, one embodiment with four transmitters and one receiver, forming four transmitter-receiver arrays), more depths of investigation can be obtained.

Some embodiments of the invention may include antennas that can function as a transceiver (i.e., as a transmitter and a receiver). This further provides tool configuration flexibility. In this implementation, for the same number of modules, a greater number of transmitter, receiver combinations can be achieved. Also, symmetrization of directional measurement can be achieved, without extending the length of the tool in a manner similar to the published U.S. Patent Application No. 2003/0085707 A1, by Minerbo et al.

Some embodiments of the invention relate to tools having a transmitter sub at a great distance from the receiver (e.g., >90 ft) to allow selective sensitivity to reservoir complexity. Such an embodiment may have an independently powered transmitter sub placed outside (far away from) a conventional bottom hole assembly.

Some embodiments of the invention relate to placement of a transmitter at or inside the drill bit, or very close to the drill bit, for look-ahead capability. Such an embodiment may have an independently powered system and data communication capability.

Some embodiments of the invention relate to having at least one module located in a separate well or borehole.

Some embodiments of the invention relate to methods of formation resistivity evaluation using measurement frequencies tailored to the expected formation. The frequency range, for example, may be up to 200 KHz.

Some embodiments of the invention related to combining modules of the invention with existing LWD resistivity arrays.

Some embodiments of the invention relate to coil designs that have multiple windings to permit the use of the same antenna for a wide range of frequencies. The multiple windings may be connected in series or parallel.

Some embodiments of the invention related to extension of the amplitude measurement to phase, relative phase and amplitude as well as phase shift and attenuation (propagation) that requires a sub to include two receiver antennas with relatively long spacing in the ten feet range.

Some embodiments of the invention relate to implementation of directional antennas (co-located or in close proximity) with or without metallic shields.

Tool Modularity

Some embodiments of the invention relate to resistivity arrays having modular designs. As used herein, a "resistivity array" is a configuration that includes at least one receiver module and at least one transmitter module attached at different locations on a drill string. The modular design allows the transmitter and receiver antennas to be placed at various locations within a BHA, or at locations in the drill string above the BHA. For example, FIG. 1 shows a resistivity array including four transmitter modules 21, 22, 23, 24 and one receiver module 25 placed among other LWD or MWD tools 27, 28, 29, 30 in a BHA. By inserting transmitter and/or receiver modules at different locations on a standard BHA, as shown in FIG. 2, or a drill string, specific depths of investigation can be implemented to optimize the formation model inversion process that uses such deep resistivity measurements. For example, in one embodiment, transmitter module 21 may be about 90 to 100 feet from receiver module 25. In addition, one or more module may be placed in a nearby borehole to provide a large spacing array.

The present inventors have found that unduly increasing the spacing between a transmitter and a corresponding receiver antenna complicates the ability for a receiver to pickup and couple the signals from a transmitter. Embodiments of the present invention may use a tri-axial antenna in a transmitter or receiver module, wherein the tri-axial antenna module has three antennas having magnetic moments in three different directions. The tri-axial antenna module will ensure that at least some of the transverse components of the tri-axial antenna can form substantial coupling with the transverse component of a corresponding transmitter or receiver. The use of a tri-axial antenna transceiver (or receiver) is advantageous because when the drill string is made up, it would be difficult to ensure that a single antenna transmitter will align with a single antenna receiver, with that difficulty increasing as the spacing increases. In contrast, the tri-axial antenna transceiver (or receiver) will always have a component substantially aligned with the magnetic moment of a corresponding receiver (or transceiver) in the resistivity array. In addition, tri-axial allows the determination of formation characteristics such as dip angle, anisotropy, shoulder bed effects.

Figure 4:
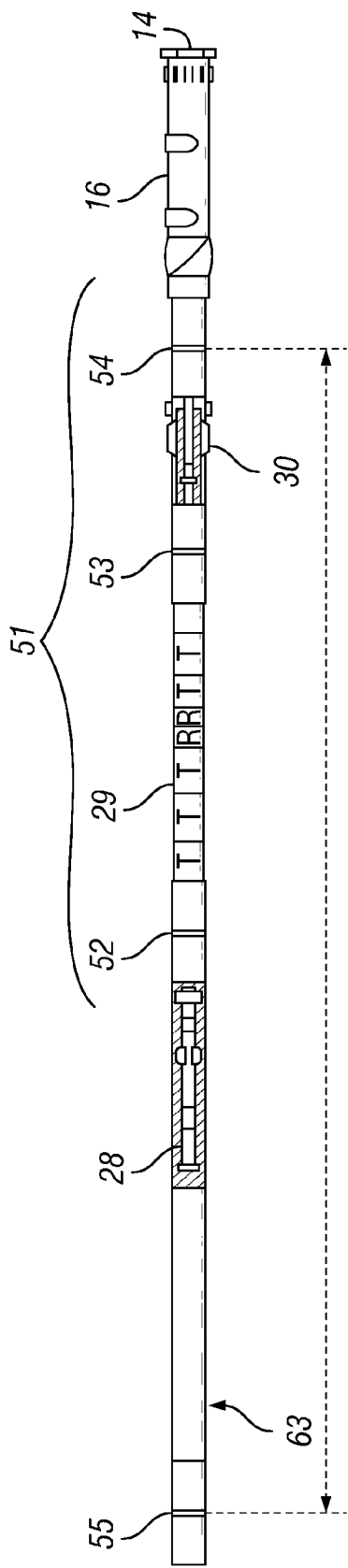
FIG. 4 shows a resistivity array according to an embodiment of the present invention.

FIG. 3 shows examples of depth of investigation for a 10 kHz amplitude measurement obtained with transmitter-receiver distances of 10, 30, 60 and 90 ft in the presence of a boundary with resistivity contrast of 1 to 10 ohms. The drill string (hence the resistivity array) is assumed parallel to the boundary and at various distances away from the boundary. As shown in FIG. 4, the 10 ft array is not very sensitive to the boundary; it shows only a slight magnitude changes in the vicinity of the boundary. The 30 ft array is more sensitive, showing a distinct transition at the boundary. The 60 ft array is even more sensitive; it shows very pronounced resistivity transition around the boundary. At this transmitter-receiver spacing, the signal magnitude starts to change at about 20-40 ft away from the boundary. With the 90 ft array, the signal magnitude change is even more profound. It is apparent that combination of different depths of investigation allows differentiations of geological formation at different radial distance. The modular design makes it easy to configure the tools for different array spacing. Further, the use of one or more tri-axial antennas as transmitters and/or receivers increases the spacing that may be achieved, which provides a corresponding increase in DOI.

Modular Subs as Transceivers

Some embodiments of the invention relate to resistivity array designs having transceiver antennas. In these tools, the antennas are not designed as separate transmitters or receivers. Instead, the same antenna can function as either a transmitter or a receiver. Such enhancement, besides being economically advantageous, allows more depth of investigation for the same number of subs, as illustrated in FIG. 2.

FIG. 2 shows a tool assembly 40 having three subs 41, 42, 43 that form two arrays with spacing of D and Dx2. Because the antennas 41 and 43 can function as a transmitter or a receiver, a third array having a spacing of Dx3 is also available with this tool configuration. Moreover, with the transceiver antennas, directional measurements can also be performed without having to have both transmitter and receiver belonging to a common downhole tool. For example, a set of symmetrized measurements may be obtained first with antenna 41 as the transmitter and antenna 43 as the receiver, then with antenna 43 as the transmitter and antenna 41 as the receiver.

Remote Subs as Transmitter/Transceivers

Some embodiments of the invention relate to tools having antenna subs placed far from other BHA tools (e.g., the receivers or transmitters). Wells often have curves and bends that limit the practical length of a BHA. Thus, conventional resistivity tools cannot have transmitters and receivers spaced farther than the practical length limit of the BHA (about 150 feet). Such tools cannot provide the depth of investigation that might be needed when placing a well path within a reservoir with a thickness that exceeds the maximum practical length of a standard drilling tool assembly.

FIG. 4 shows a resistivity array incorporating a remote sub in accordance with one embodiment of the invention. As shown, the resistivity array includes a conventional UDR 51 in the BHA. The UDR includes three antennas (transmitters, receivers, or transceivers) 52, 53, 54. Further up the drill string, the resistivity array also includes a remote module 55, which includes a transmitter, a receiver, or a transceiver. The antenna in the remote module 55 may be used with any of the antennas 52, 53, 54 to form an array having a large spacing. By using a remote module 55 with other conventional resistivity tools in the BHA, transmitter-receiver distances (i.e., array spacing) can be set to any desired distance. The remote module 55 may be independently powered. Furthermore, the remote module 55 may be operated by wireless telemetry, for example. In one embodiment, one or more drill collars 63 may be located between the remote module 55 and one or more of the antennas 52, 53, 54.

The location of the remote module 55 may be selected to be on the order of (or greater than) the reservoir thickness. Having an array spacing on the order of (or greater than) the reservoir thickness can provide distinct advantages that are otherwise unavailable to conventional resistivity tools.

Figure 6B:
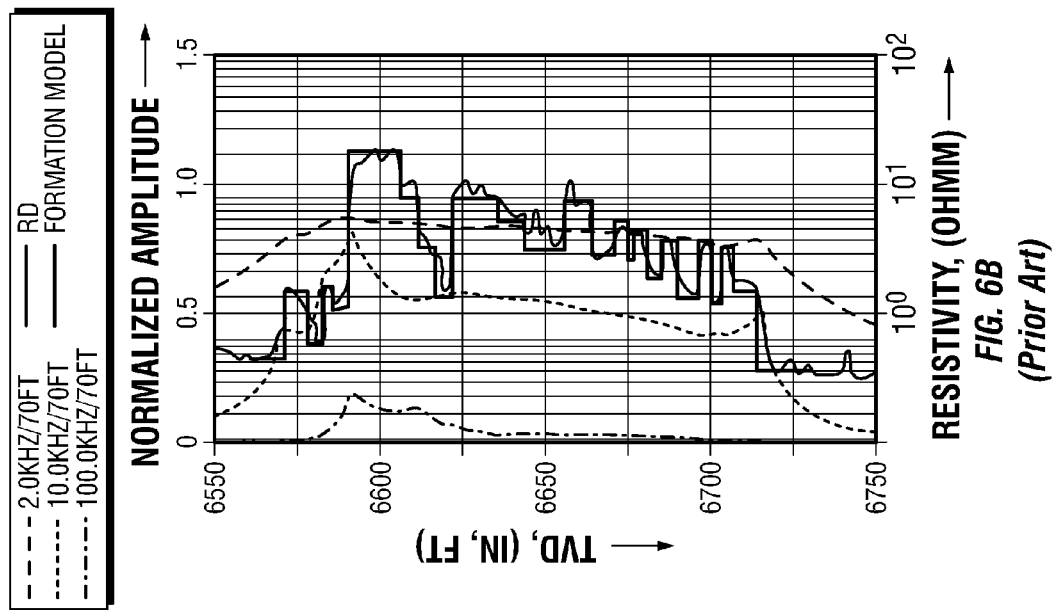
FIGS. 6A and 6B show amplitude responses of conventional prior art resistivity arrays.
Figure 6A:
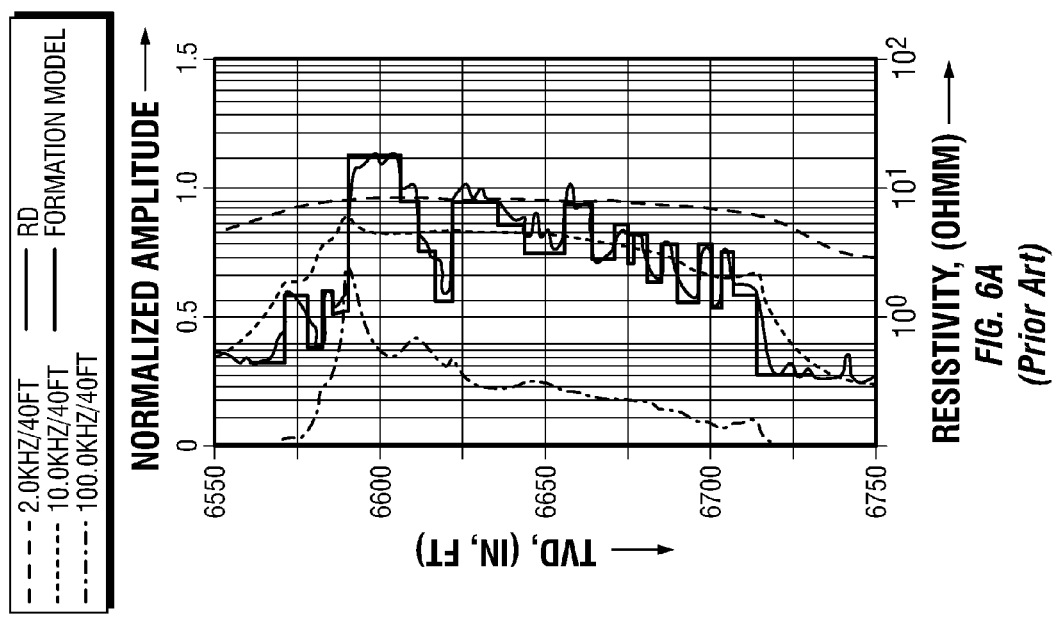
Figure 6D:
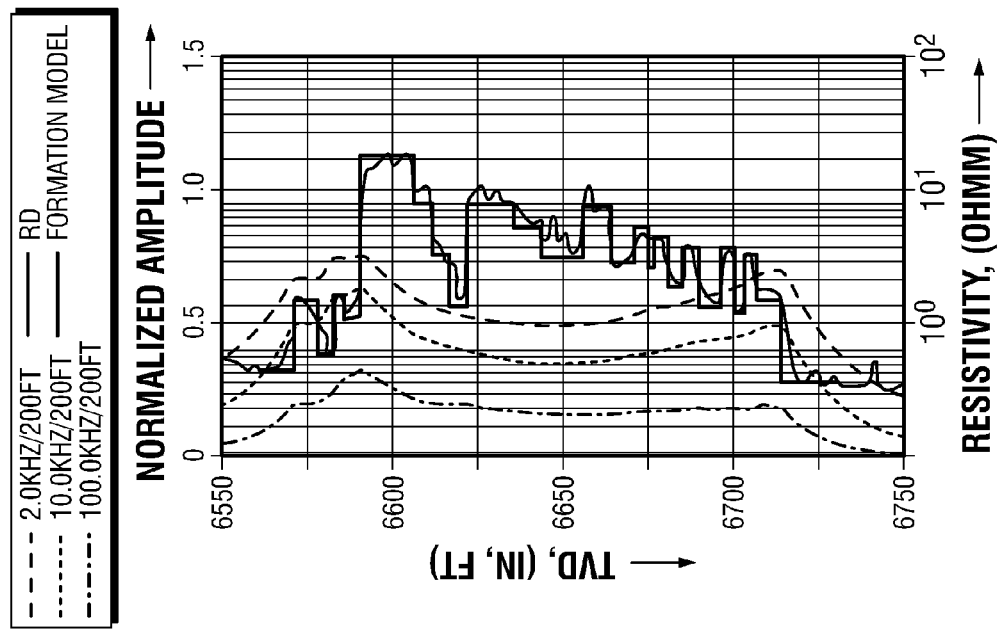
FIGS. 6C and 6D show amplitude responses of resistivity arrays according to an embodiment of the present invention.
Figure 6C:
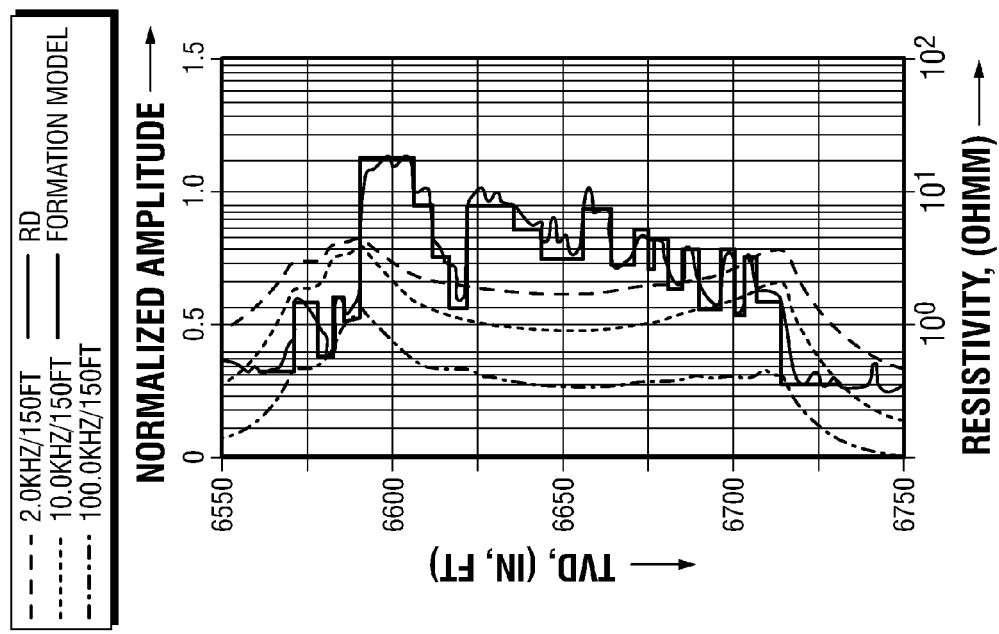

For example, FIGS. 6C and 6D show that the amplitude responses of the long array (the spacing of which is on the order of the bed thickness, 130 ft) are much simpler and clearly indicate where the bed boundaries are. The responses of this extra long array (especially at low frequencies) are not sensitive to the reservoir internal complexity. In contrast, as shown in FIGS. 6A and 6B, the amplitude responses of conventional prior art resistivity arrays (the spacing of which are smaller than the bed thickness, 130 ft) are more sensitive to resistivity variations within the bed, but less sensitive to bed boundaries. Results from FIGS. 6A-6D show that sensor distances (array spacing) and operational frequencies may be advantageously selected based on the properties of the reservoir being drilled, for example, the expected bed thickness or the ratio of the lowest reservoir layer resistivity and the resistivity of the cap and reservoir bottom.

Look-Ahead with Subs at the Bit

Some embodiments of the invention relate to resistivity tools having look-ahead ability. In accordance with embodiments of the invention, a sub may be placed proximate the drill bit in a way similar to that described in U.S. Pat. No. 6,057,784 issued to Schaff et al., and assigned to the assignee of the present invention. That patent is incorporated herein by reference in its entirety. In addition, an antenna can also be placed on a rotary steerable tool or directly inside a bit. By placing a transceiver at the bit, the resistivity measure point taken at the mid-distance between each transmitter/receiver pair is moved closer to the bit, thus allowing faster reaction time while drilling. This ability allows earlier real-time action to be taken to place the well based on geological events. Moreover, look-ahead of the bit is also possible by using the tool response tail that extends beyond a resistivity sensor pair.

Figure 5:
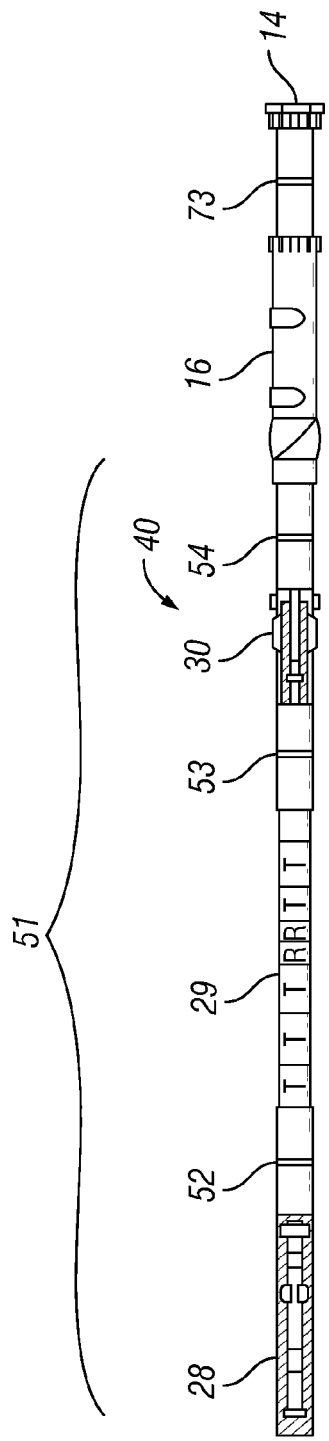
FIG. 5 shows a resistivity array according to an embodiment of the present invention.

FIG. 5 shows one example of a resistivity array in accordance with one embodiment of the invention. As shown, the resistivity tool 70 comprises a drill bit 14 at one end of the drill string. An antenna 73 (which may be a transmitter or a receiver antenna) is disposed on the drill string proximate the drill bit 14. In addition, the resistivity array includes a UDR 51 having three transceiver modules 52, 53, 34, which can function as receivers or transmitters. While three transceiver modules are shown in this example, one of ordinary skill in the art would appreciate that such a tool may have more or less transceiver modules. Further, receiver or transmitter modules may replace one or more of the transceiver modules. In one embodiment, antenna 73 may be a component of drill bit 14.

In accordance with some embodiments of the invention, the near-bit antenna 73 has a non-longitudinal magnetic moment, i.e., the magnetic moment of the antenna 73 is not in a direction parallel with the drill string axis. The non-longitudinal magnetic moment of the antenna 73 ensures that the antenna 73 has a component of the magnetic moment in the transverse direction (i.e., the direction perpendicular to the drill string axis). In addition, at least one of the transceiver modules (e.g., 52, 53, 54) comprises a tri-axial antenna, in which three antennas have magnetic moments in three different orientations. In some cases, the tri-axial antennas may have magnetic moments in three orthogonal orientations. The tri-axial antenna module will ensure that at least some of the transverse components of the tri-axial antenna can form substantial coupling with the transverse component of the near-bit antenna 73. The near-bit antenna 73 may be a transmitter, receiver, or a transceiver. In general, it is preferable for the near-bit antenna 73 to be a transmitter because a receiver antenna may see higher electrical noise from increase vibration and shock or from a possible presence of a high power rotary steerable tool. As a result, the motor assembly 16, which may include powered steering components, can disrupt a receiver antenna.

Multi-Frequency Measurement

Some embodiments of the invention relate to tools and methods that use multi-frequencies for resistivity measurements. In accordance with embodiments of the invention, frequencies may be selected to more efficiently cover the frequency spectrum in order to improve the inversion accuracy and flexibility of deep resistivity measurements. For example, in accordance with some embodiments of the invention, measurements may be acquired with a distribution of 3 or more frequencies per decade. These frequencies can be set or automatically selected, either before drilling or while drilling, to provide optimal formation inversion. The combination of transmitter receiver distance with frequency is integral in the determination of reservoir outer boundaries with complex internal layer. The combination of antenna spacing and frequency are preferably selected to respect the following equation for maximum sensitivity.

Let's define propagation coefficient k as: $k^2 = \epsilon\mu\omega^2 + i\sigma\mu\omega$, where $\epsilon$ is the electromagnetic permittivity, $\mu$ electromagnetic permeability, $\sigma$ conductivity, and $\omega$ the angular frequency. If L represents the Transmitter-Receiver spacing, then we want: $|k|.L \in [0.1; 10]$. The frequencies are preferably chosen to meet this criterion.

Figure 7:
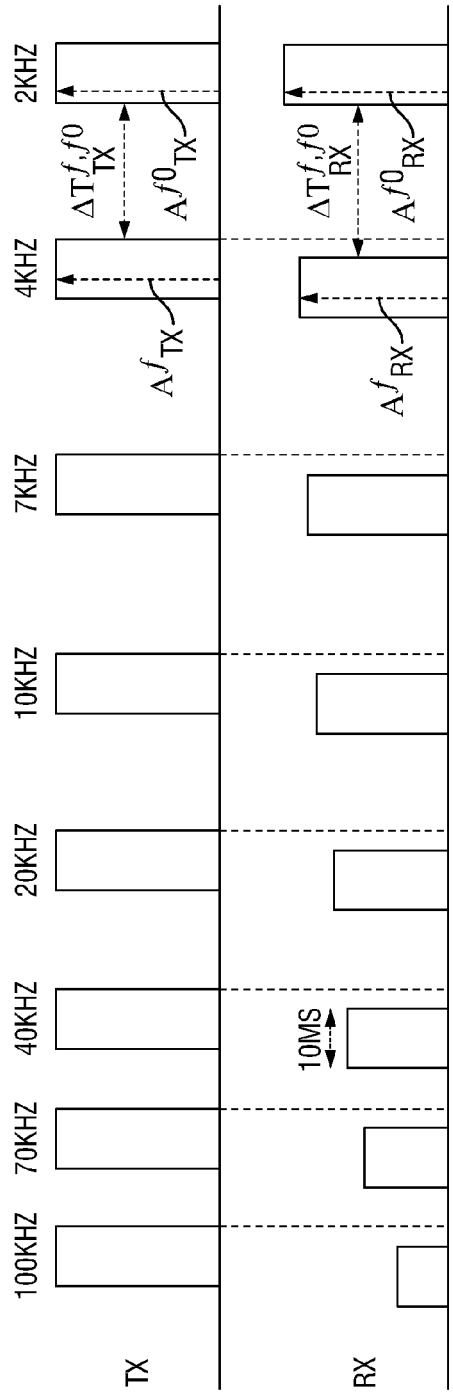
FIG. 7 shows a sequencing method according to an embodiment of the present invention.

The multi-frequency measurements can be efficiently performed using any implementation scheme known in the art. For example, FIG. 7 shows an example of a resistivity measurement sequence for multi-frequency measurement. In the scheme shown in FIG. 7, all TX pulses are assumed to have a controlled amplitude. Furthermore, one of ordinary skill in the art would appreciate that in the pulse scheme, as shown in FIG. 7, a single pulse may be implemented to carry two or more frequencies. Signal measurements may be performed by measuring the true voltages as sensed by the receivers. Alternatively, the signals may be measured as differential signals between a pair of pulses of different frequencies.

Combination of Subs with Existing LWD Tools

Some embodiments of the invention relate to resistivity arrays having remote subs, as described above, with other conventional resistivity tools. For example, FIG. 8 shows a tool including two remote sub transmitters, 55A and 55B, and a conventional LWD resistivity tool that may function as receivers for the remote transmitter modules to provide arrays with spacing much longer than what is possible with conventional resistivity arrays. One of ordinary skill in the art would appreciate that any conventional resistivity tool having one or more antennas for receiving resistivity signals may be used in combination with remote sub transmitters as disclosed herein. The option of running transmitter modules in combination with an existing "shallow" LWD tool (using their resistivity antennas as deep resistivity receivers) allows asset rationalization and integrated measurement capabilities.

Multi-Winding Antenna

Some embodiments of the invention relate to antennas that may be used efficiently in a wide frequency range. When an antenna is used to transmit a resistivity signal at a certain frequency, the antenna is most efficient when the frequency is below the self-resonance frequency of the antenna. Therefore, when a particular antenna is used in a wide frequency range, the antenna may not be efficient in certain frequency ranges. For example, to transmit at the highest frequency, the number of turns in the antenna should be low enough to be below the coil self resonance. On the other hand, to be optimum in transmission at a lower frequency, the number of turns needs to be increased. As a result, conventional antennas often have windings that represent a compromise for the intended operational frequency range.

In accordance with some embodiments of the invention, an antenna may have several layers of windings; each of the layers may be either wired in parallel for high frequency or in series for a lower frequency to efficiently balance the impedance load of the antenna when driven with a constant voltage. The switching between serial and parallel configurations may be controlled electronically.

FIG. 9 shows an exemplary antenna in accordance with one embodiment of the invention. Coil layers 101A-101C, in this example, are either connected in series to maximize the number of turns in the transmission at low frequency (for example, around 1 kHz range), or are connected in parallel for the higher frequency range (for example, 100 kHz). The coil layers 101A-101C are wrapped around a mandrel 102. One of ordinary skill in the art would appreciate that several layers of coils may be used in an antenna to provide finer tuning of the performance of the antenna.

Extension to Other Resistivity Measurement Techniques

Conventional deep resistivity measurements, such as that disclosed in U.S. Pat. No. 6,188,222, are based on induction mechanism and measures signal amplitudes, not phase or phase shifts or attenuations. Some embodiments of the invention relate to deep resistivity measurements based on propagation mechanism and measure phase shifts and attenuations (i.e., differential measurements), by introducing an extra receiver antenna with a spacing between the receiver pair on the order of 5 to 10 feet, which is significantly longer than the receiver pair spacing (typically limited to less than a foot) in a conventional propagation tool. The longer spacing between the receiver pair is desirable because of the lower frequencies used for deep EM measurement (1 to 200 kHz). A spacing between the receiver pairs on the order of 5 to 10 feet would ensure that the minimum phase shift that can be measured stays in the ~0.1 degree range.

In addition to using a receiver pair, differential measurements in phase and amplitude (i.e., phase shifts and attenuations) may also be performed with a proper pulse scheme, such as that shown in FIG. 7. The measurement scheme shown in FIG. 7 may use one (or more) of the transmitted pulses at a specific frequency as a time reference. Assuming a constant phase reference (or time difference) between pulses in the pulse train (this time difference can also be measured and communicated to the receiver via wireless telemetry), the phase reference (or time difference) for the received pulse trains can be determined with respect to the reference pulse.

The same technique (using the amplitude of a reference pulse for comparison) can also be applied to the amplitude ratio between each pulse in the pulse train and the reference pulse. In this case, the amplitude ratio at the transmitter may be kept constant or measured. The difference technique in pulse time of arrival and amplitude ratio reduces the dependence of the measurement on an accurate air calibration as needed for the amplitude measurement.

As an example, FIGS. 10A-10F show various measurements for a planar boundary with resistivity contrast of 1 and 100 ohms, using a tool having a transmitter-receiver spacing of 70 feet. This tool has transmitter and receiver antennas that have longitudinal magnetic moments (i.e., magnetic moments in a direction parallel with the longitudinal axis of the tool).

Figure 10A:
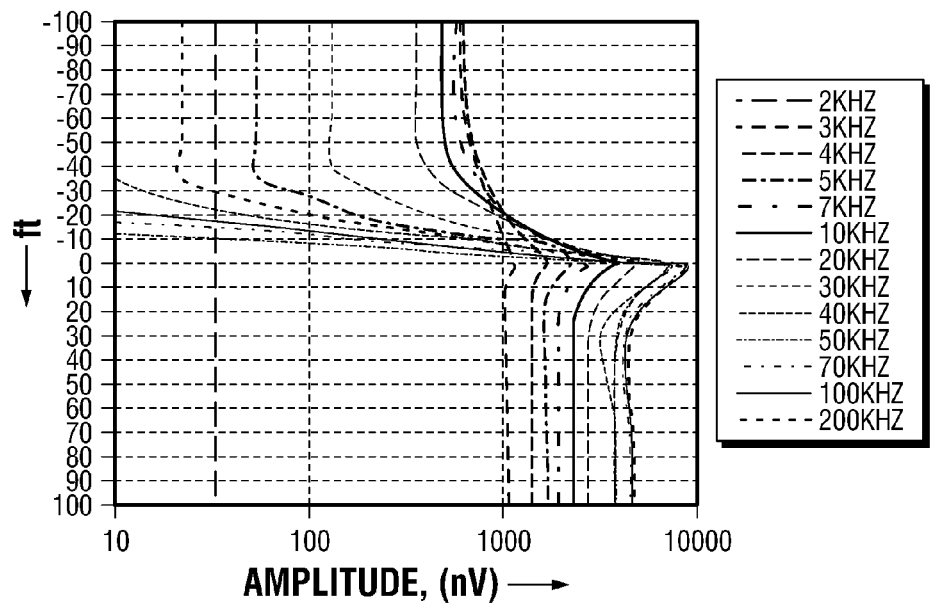
FIGS. 10A-10F show various measurements for a planar boundary with resistivity contrast according to an embodiment of the present invention.
Figure 10B:
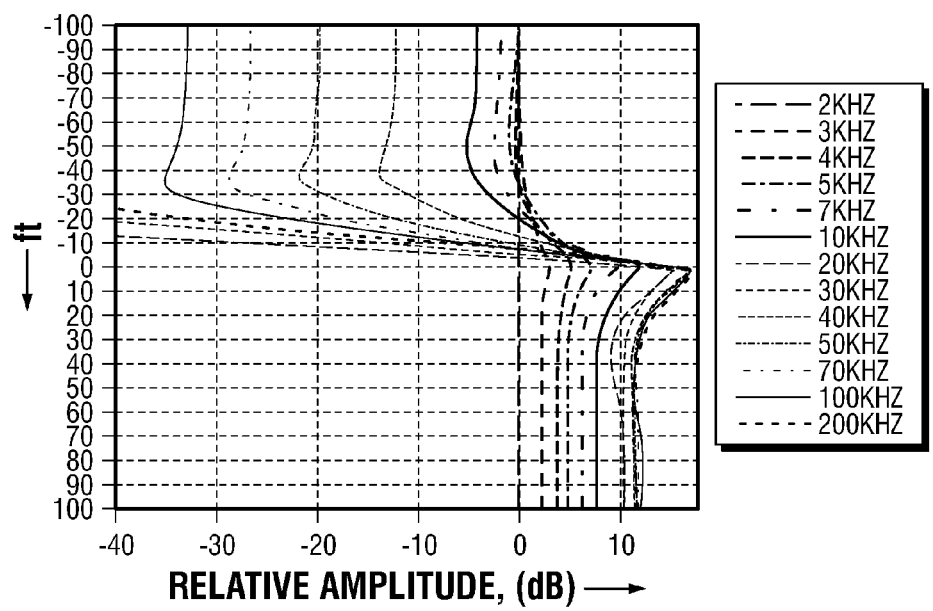
Figure 10C:
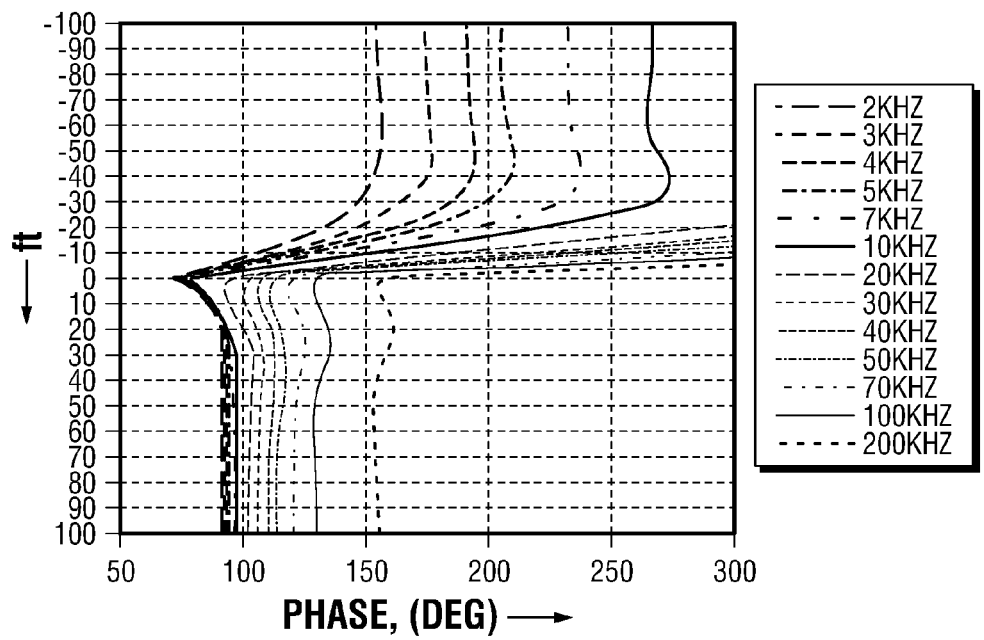
Figure 10D:
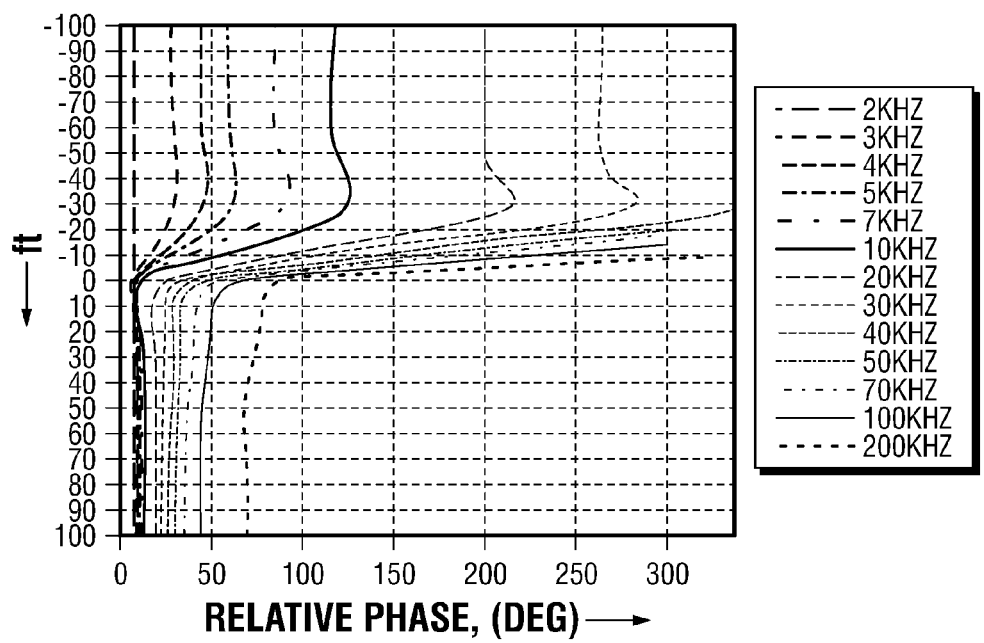

FIG. 10A and FIG. 10B show amplitude measurements and relative amplitude measurements, respectively, at various frequencies. In FIG. 10B, the relative amplitude measurements are with respect to the amplitude measurement at 2 KHz. FIG. 10C and FIG. 10D show phase measurements and relative phase measurements, respectively, at various frequencies. In FIG. 10D, the relative phase measurements are with respect to the phase measurement at 2 KHz.

Figure 10E:
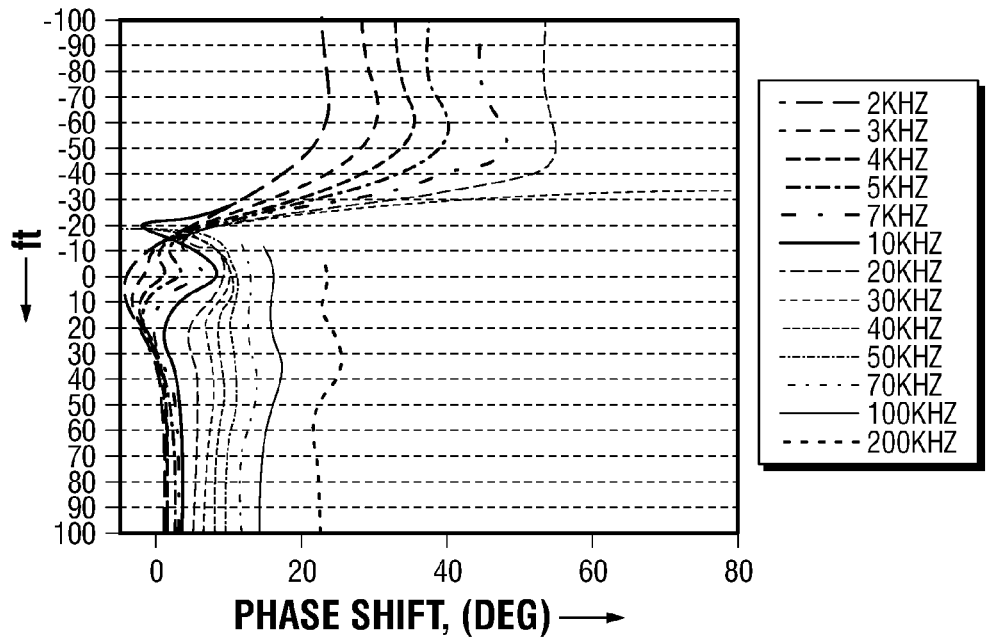
Figure 10F:
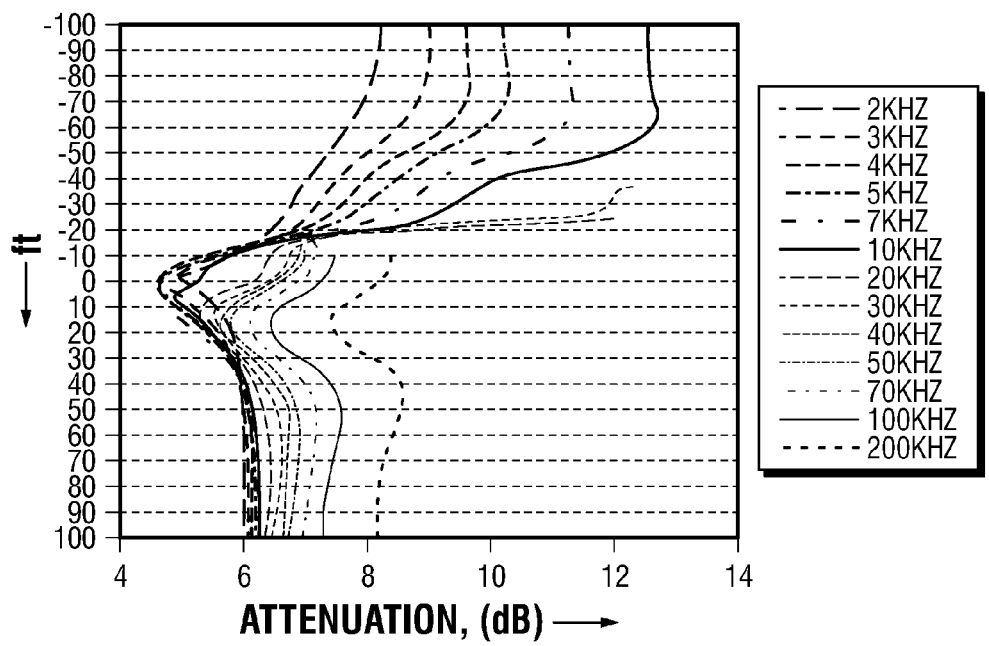

FIG. 10E and FIG. 10F show phase shift measurements and attenuations, respectively, at various frequencies, as measured with a pair receivers having an 8 feet spacing. With such a spacing, significant variations in Phase Shift and Attenuation can be readily observed. Both measurements provide another set of measurements with a different sensitivity allowing more independent measurements to be used during the inversion process.

Some embodiments of the invention relate to geo-steering. A method of geo-steering in accordance with embodiments of the invention may use any resistivity array described above and/or using a measurement method described above (e.g., multi-frequency measurements, use of a pulse schemes, etc.).

All measurements with the above-described embodiments of the invention can be extended to directional measurements. Directional measurements allow further sensitivity to the boundaries and will improve the inversion process accordingly. In some embodiments, the antenna(s) would have a transverse magnetic dipole combined with a normal "axial" antenna to provide both measurements from the same antenna. In a tri-axial antenna, as discussed above, one portion may be aligned with the axis of the BHA, while the other two portions are at angles relative thereto. Conventional shields can also be implemented with embodiments of the invention as desired. It will be appreciated that the antennas (and related electronics) of the embodiments of the invention may be implemented using one of many well-known antenna designs and packaging schemes. For example, the logging apparatus described in U.S. Pat. No. 6,188,222 may be used to implement the present invention.

While the embodiments described herein may illustrate logging-while-drilling tools to help explain various embodiments of the invention, a tool of the invention is not limited by any particular mode of conveyance. Therefore, a tool of the invention may be used in, for example, logging-while-drilling, logging-while-tripping, coil drilling, logging through the bit, liner drilling, casing drilling operations.

According to an alternate embodiment of the invention, another system and method facilitate obtaining data related to a subterranean region. For example, a logging while drilling, look-ahead system may be used to facilitate the detection and measurement of various subterranean features and characteristics. The logging while drilling system can "look-ahead" by obtaining data from regions ahead of the logging while drilling system during, for example, drilling of a wellbore.

Referring to FIG. 11, an example of a system 40 used to perform logging operations in a wellbore 42 is illustrated according to one embodiment of the present invention. In the illustrated embodiment, system 40 comprises a logging while drilling system 44 combined with a tool, such as a bottom hole assembly 46. Bottom hole assembly 46 may comprise a drill bit 48 used to drill wellbore 42 while logging a subterranean region 48 in which wellbore 42 is formed.

In the embodiment illustrated, bottom hole assembly 46, including logging while drilling system 44, can be conveyed downhole via a conveyance 50. Conveyance 50 may be in the form of drill pipe, coiled tubing or another suitable type of conveyance. Additionally, system 40 may comprise a control system 52 coupled to logging while drilling system 44 via an appropriate wired or wireless communication line 54. By way of example, control system 52 may comprise a computer-based control system for processing data received from logging while drilling system 44. The data/process results can be displayed for use by an operator on a suitable display 56, such as a computer monitor, positioned at a surface location.

In the example of FIG. 11, logging while drilling system 44 comprises a transmitter module 58 having a transmitter antenna 60 and a receiver module 62 having a receiver antenna 64. In the specific example illustrated, the logging while drilling system 44 comprises a plurality, e.g. two, of the receiver modules 62. The transmitter module 58 and the receiver module or modules 62 are positioned at separate locations along the bottom hole assembly 46, and the spacing is selected to provide a desired depth of investigation. The transmitter module 58 is located close to a drill bit 66 of bottom hole assembly 46. For example, the transmitter module 58 may be mounted on a sub 68 behind a drill bit 66 or otherwise in close proximity to the drill bit. With such a system, a measure point (taken as the midpoint between transmitter module 58 and receiver module 62) is pushed towards the drill bit 66 in a manner that provides not only radial sensitivity but also sensitivity ahead of the transmitter antenna 60.

In the embodiment illustrated in FIG. 11 and in other embodiments described below, various antenna configurations may be utilized. For example, the transmitter module 58 may have a tilted antenna 60. Use of a tilted antenna means the magnetic dipole moment is not aligned with the tool axis, e.g. the bottom hole assembly axis, nor is the magnetic dipole moment orthogonal to the tool axis. The receiver module 62 also may use a tilted antenna 64, or its antenna 64 may comprise an axial antenna in which its magnetic dipole moment is along the tool axis or orthogonal to the tool axis. In one useful embodiment, the total number of antennas in the transmitter and receiver modules is four, and many configurations of those four antennas can be utilized.

Although the antennas have been described in terms of magnetic dipole antennas, the antennas 60, 64 also may comprise electric dipole antennas. By way of example, magnetic dipole antennas, such as coils, may be used in induction and/or propagation measurements. Electric dipole antennas may use electrodes and/or toroids. Depending and the specific application, the roles of transmitter antennas and receiver antennas can be interchanged.

The embodiment of system 40 illustrated in FIG. 11 positions the transmitter module 58 directly behind drill bit 66. By way of example, the transmitter module 58 and antenna 60 may be added to a bit box 70 of a mud motor 72 used to drive the drill bit 66. It should be noted that each transmitter module 58 also may comprise one or more sensors 74 and the associated electronics 76 that are powered through an external or internal wire or by an onboard battery. Additionally, the logging while drilling system 44 may incorporate a variety of other modules 78 that may comprise a variety of tools or sensors depending on the specific logging operation anticipated for a given application.

Figure 13:
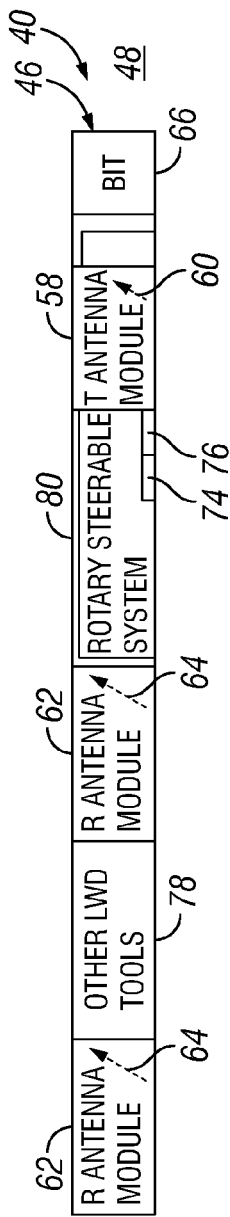
FIG. 13 is a schematic illustration similar to that of FIG. 11 but showing another example of the system, according to an alternate embodiment of the present invention.
Figure 14:
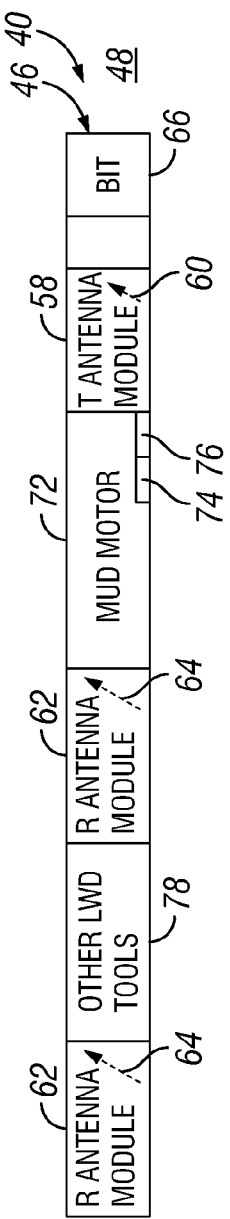
FIG. 14 is a schematic illustration similar to that of FIG. 11 but showing another example of the system, according to an alternate embodiment of the present invention.
Figure 15:
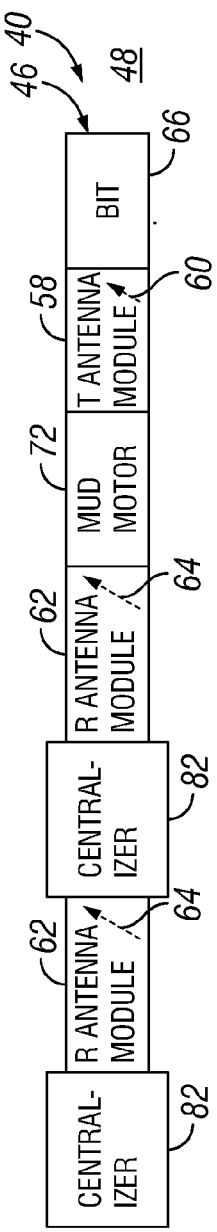
FIG. 15 is a schematic illustration similar to that of FIG. 11 but showing another example of the system, according to an alternate embodiment of the present invention.

Referring to FIG. 12, a similar embodiment is illustrated in which the drill bit 66 is driven by a rotary steerable system 80. By way of example, the embodiments illustrated in FIGS. 11 and 12 can position sensors 74, e.g. electromagnetic sensors, directly behind drill bit 66 or as integrated with drill bit 66. In alternate embodiments, the sensor or sensors 74, along with the corresponding electronics 76, can be mounted directly on the rotary steerable system 80, as illustrated in FIG. 13, or on the mud motor 72, as illustrated in FIG. 14. In the embodiments described above, a variety of antennas can be utilized. For example, the transmitter antenna 60 may be formed as a tri-axial antenna TX, and the receiver antennas 64 may be formed as tri-axial RCV antennas. The corresponding sensors may be individual sensors or combinations of induction/propagation and/or laterolog sensors. In another embodiment illustrated in FIG. 15, the antennas are toroidal electric dipole antennas that may be particularly useful for wells drilled with oil base mud. In this embodiment or other embodiments, additional components, such as centralizers 82, can be incorporated into bottom hole assembly 46.

Generally, having transmitter antennas at the drill bit is helpful because power is usually more readily available. For example, a rotary steerable system often uses a turbine from which power can be taken. Moreover, receiver antennas located at or near the drill bit are expected to have higher noise than customary logging while drilling tools because of the higher shock environment (microphonic noise) at or near the drill bit and because of the considerable amount of electrical power that is usually expended by the rotary steerable system.

A directional antenna is an antenna having a dipole moment not aligned with the tool axis. With one or more directional transmitter antennas 60 placed on or near the drill bit 66, measurements can be made that are sensitive to features ahead of the transmitter antenna and the drill bit. Often, voltage measurements are made for the amplitude and phase of the voltage induced at the receiver antennas 64 by a signal from one or more transmitter antennas 60. The voltage is proportional to the directions and magnitudes of the transmitter and receiver dipole moments via an electromagnetic coupling tensor. The coupling tensor depends on the frequency of the transmitted signal, the transmitter/receiver spacing, and the formation parameters.

Figure 16:
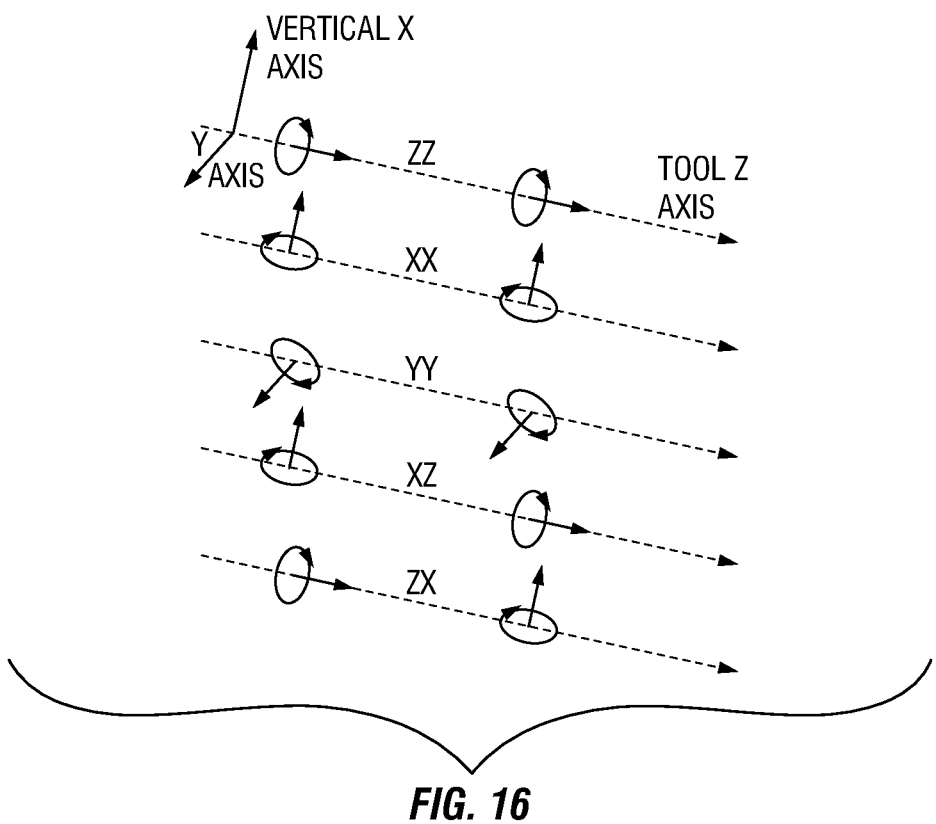
FIG. 16 is a representation that defines an electromagnetic coupling tensor and illustrates its relation to antenna orientations, according to an embodiment of the present invention.

In FIG. 16, an illustration is provided to define an electromagnetic coupling tensor and to show its relation to the antenna orientations. In the example of FIG. 16, the Z axis is aligned with the tool axis, and the X and Y axes are perpendicular to each other and to the Z axis. The first letter of the coupling tensor component corresponds to the dipole moment direction of the receiver, and the second letter corresponds to the dipole moment direction of the transmitter. Once voltage measurements are made and the orientations and magnitudes of the transmitter and receiver antenna dipole moments are known, the electromagnetic coupling tensor can be obtained. To infer properties of the features ahead of the drill bit 66, the electromagnetic coupling tensor can be used or the electromagnetic coupling tensor can be transformed to its corresponding formation parameter tensor, such as a conductivity tensor, which can then be used to infer desired properties of the subterranean region ahead of the drill bit. Individual components of those tensors may be used, or various combinations of the components may be used to infer the formation properties. For example, any of the following combinations may be used:

- ZZ/(XX+YY), sometimes referred to as the "harmonic resistivity" (HR);
- (ZZ−XZ)/(ZZ+XZ)*(ZZ+ZX)/(ZZ−ZX), sometimes referred to as the "symmetrized directional" (SD) or "first harmonic directional";
- XX/YY, sometimes referred to as the "second harmonic directional"; and
- (ZZ+XZ)/(ZZ−XZ)*(ZZ+ZX)/(ZZ−ZX), sometimes referred to as the "anti-symmetrized directional" (AD).

Each measurement contains information about the formation structure (resistivity, layering, dip, and other parameters). In operation, a response is measured that is sensitive to the surrounding formation, including the determination of a bed ahead of the drill bit 66 if one is present. A simulated response also can be produced by modeling a well bore with no boundary ahead of the drill bit. The difference between the actual response and the modeled response is computed via, for example, control system 52. If the difference is zero, a conclusion can be made that there is no bed ahead of the drill bit, but if the difference is not zero, a conclusion can be made that the difference is attributable to the presence of a bed ahead of the drill bit.

Figure 17:
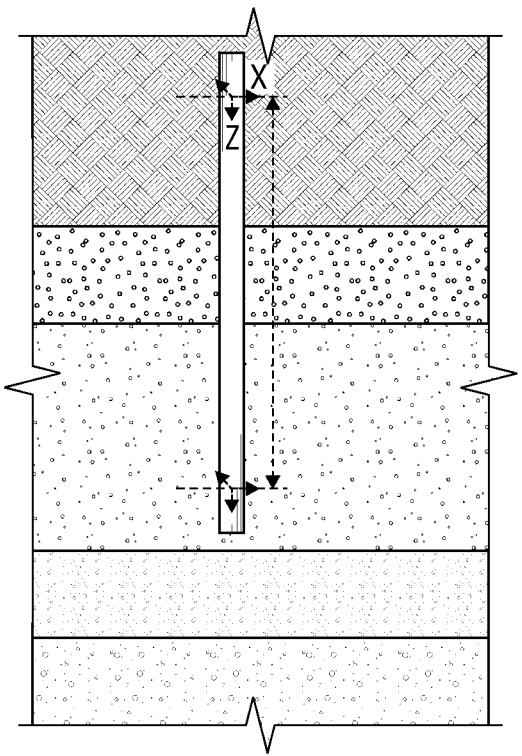
FIG. 17 is a model representation of the logging system utilized in a generally vertical well, according to an embodiment of the present invention.
Figure 18:
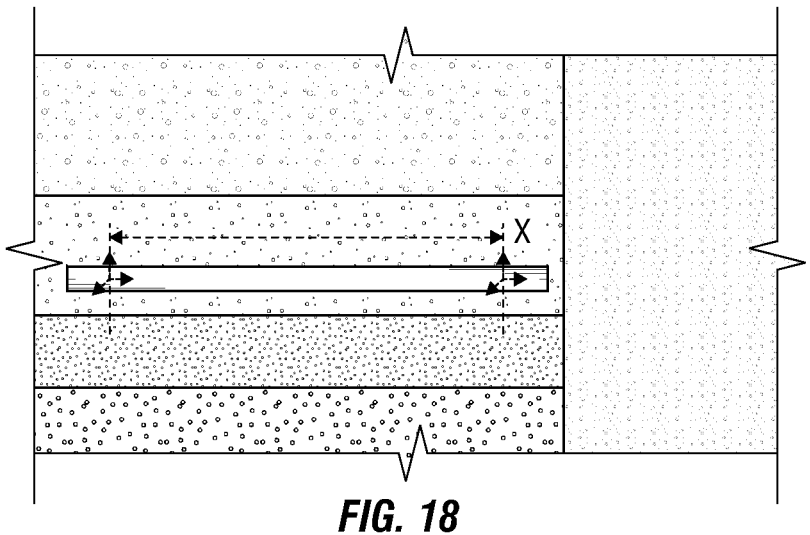
FIG. 18 is a model representation of the logging system utilized in a generally horizontal well, according to an embodiment of the present invention.

In FIGS. 17 and 18, illustrations are provided of modeling configurations used to generate the elementary couplings.

The elementary couplings are generated according to the bottom hole assembly orientation with respect to the formation. For example, the modeling configuration illustrated in FIG. 17 represents a generally vertical orientation, and the modeling configuration illustrated in FIG. 18 represents a generally horizontal orientation. The formation illustrated also can have a relative dip with respect to the bottom hole assembly.

Figure 19:
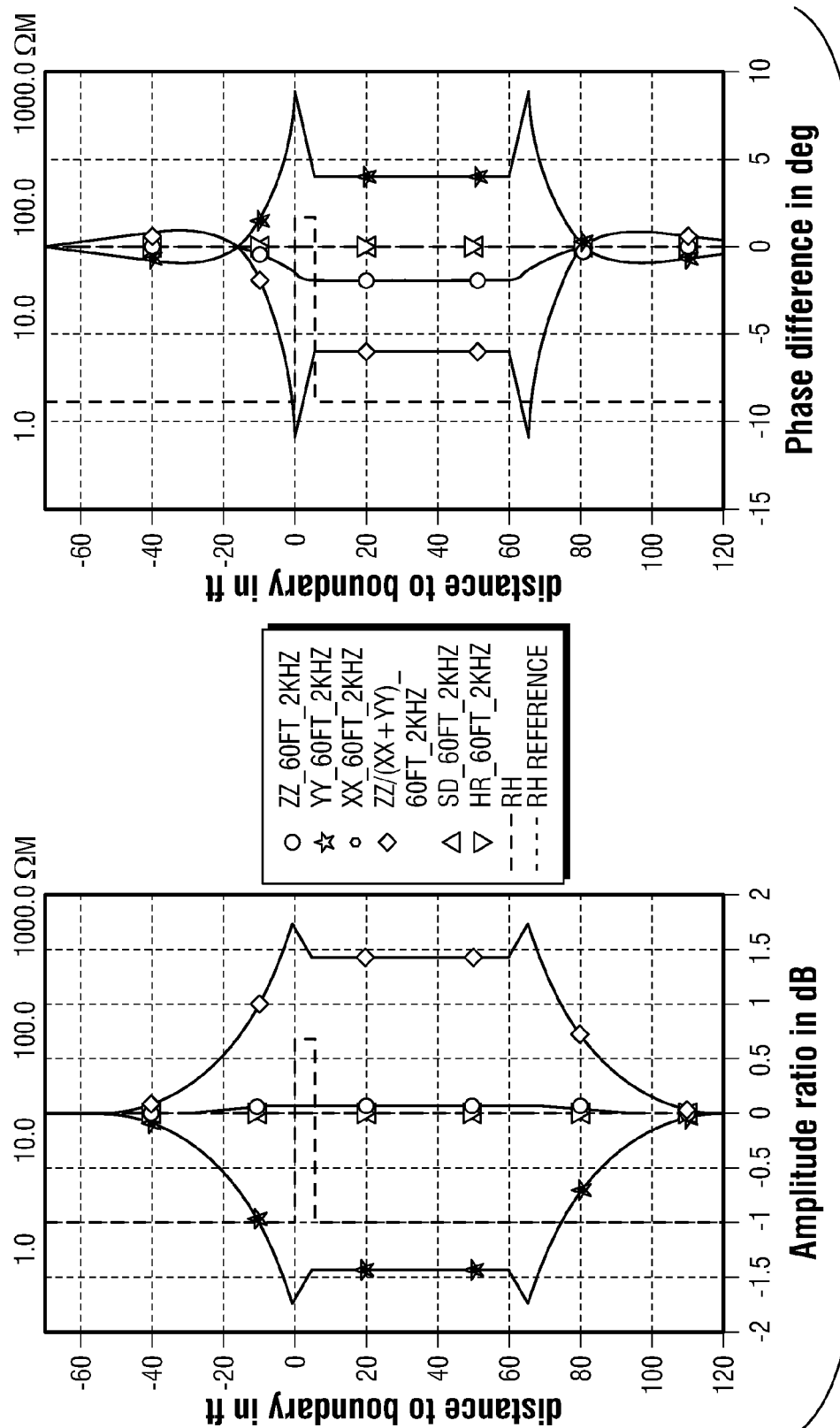
FIG. 19 is a graphical representation of results output by one example of the logging system in a substantially vertical well, according to an embodiment of the present invention.
Figure 20:
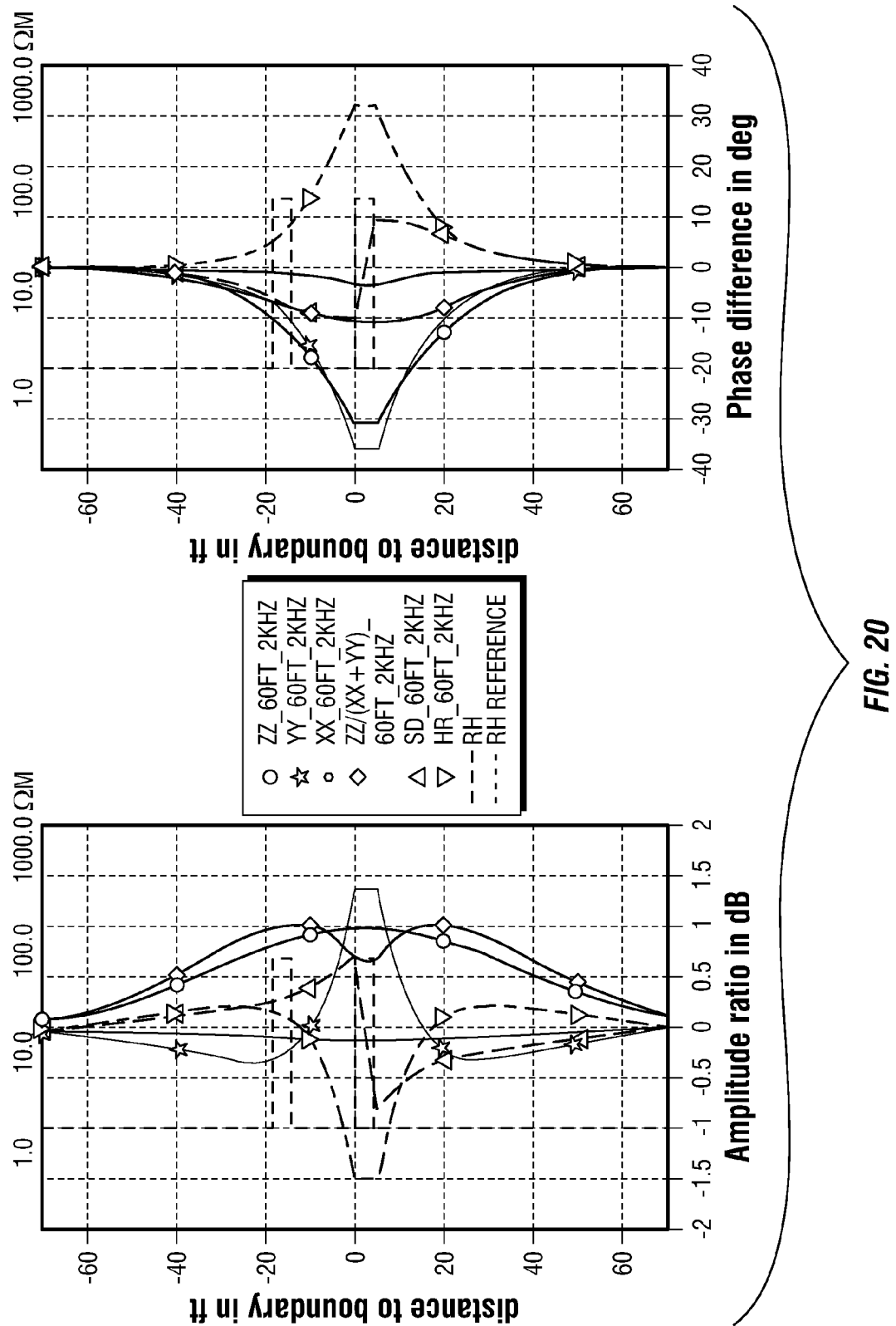
FIG. 20 is a graphical representation of results output by one example of the logging system in a substantially horizontal well, according to an embodiment of the present invention.

Referring generally to FIGS. 19 and 20, graphical examples are illustrated that represent results from the logging system 44 when it is constructed as an induction tool with a predetermined transmitter-receiver (T-R) antenna spacing and a predetermined frequency when crossing a formation of a specific thickness. By way of example, the T-R spacing is 60 feet and the frequency is 2 kHz when crossing a 5 foot thick formation. By way of example, the results may be displayed on display 56 of a suitable control system. In FIG. 19, a look-ahead case is provided in which the well is substantially vertical, and in FIG. 20 a look-around case is provided in which the well is substantially horizontal. In these examples, the response is the difference between signals generated with and without a bed ahead of the drill bit 66. The response is expressed both as an amplitude ratio on the left graph of each Figure and as a phase difference on the right graph of each Figure. In the substantially vertical example of FIG. 19, the ZX and XZ cross couplings are zero.

In the look-ahead example illustrated in FIG. 19, only the diagonal terms of the coupling tensor (XX, YY, and to a lesser extent ZZ) and ZZ/(XX+YY) show a dependence on the formation that can be used. It should be noted that the ratio ZZ/(XX+YY), when used in low dip and anisotropic formations, does not change drastically. In this example, at distances of about 50 ft above the bed, the amplitude ratio responses begin to deviate from zero, indicating the presence of a bed of different resistivity ahead of the drill bit. As the tool/bottom hole assembly nears the bed, the deviations increase until the first antenna crosses the bed boundary, at which time the response shows a maximum magnitude. Similarly, the phase difference of the responses begins to deviate from zero at approximately 60 ft above the bed boundary, as shown in the right graph of FIG. 19. In the responses shown, there is a crossover at approximately 20 ft above the bed that, in addition to the previously mentioned deviations, is indicative of a bed being present ahead of the bit. Generally, the phase difference responses have a greater look-ahead sensitivity than the amplitude ratio responses.

In the look-around example illustrated in FIG. 20, all responses plotted show a dependence on the formation. In this example, at distances of about 70 ft before the bed, the amplitude ratio responses begin to deviate from zero, indicating the presence of a bed of different resistivity ahead of the drill bit. As the tool/bottom hole assembly nears the bed, the deviations generally increase until the first antenna crosses the bed boundary, at which time certain responses show a maximum deviation. In the responses shown, there is a crossover at approximately 10 ft before the bed that is indicative of a bed being present ahead of the bit. Similarly, the phase difference of the responses begins to deviate from zero at approximately 50 ft before the bed boundary, as shown in the right graph of FIG. 20.

As illustrated in FIG. 20, any one of the responses plotted is sensitive to the bed ahead of the bit and can be used to estimate the distance to the bed boundary ahead of the bit. Consequently, the entire coupling tensor may not be required. For example, the symmetrized response may be determined using only a single tilted transmitter antenna and a single tilted receiver antenna.

The distances mentioned above are exemplary and are controlled by the T-R spacings, as well as the frequency used in operation. In general it is useful to make measurements with more than one T-R spacing and more than one frequency to improve confidence in the interpretation of the results.

In addition to plotting the responses, the responses can be inverted to compute, for example, a distance to the bed boundary ahead of the bit or the conductivity, anisotropy, and dip angle of the formation ahead of the bit. The inversion may be 1D, 2D, or 3D. A more stable and reliable inversion may be had by using various combinations of T-R spacings and frequencies. Inversions provide accurate estimates of the distances to the bed boundary ahead of the bit when that distance is within approximately ⅔ of the T-R spacing. However, that ratio can be improved depending on formation properties.

In the look-ahead example, look-ahead features are clearly present as a tail feature. Change in an RCV response due to look-ahead features is volumetric and can be taken separately from the formation around a TX RCV system. Each diagonal term can be used independently, but in the example provided both TX and RCV channels are calibrated so absolute measurements that are only sensitive to formation features can be determined. Calibration is performed because the TX output current and the RCV system, which usually comprise an antenna coupled with amplification electronics, can have variation that is dependent on temperature and other environmental factors. As illustrated in FIGS. 19 and 20, another combination having similar response to individual diagonal terms comprises taking the ratio ZZ/(XX+YY). Generating measurement as ratios of elementary couplings has the advantage of being calibrated so no absolute measurement is necessary.

Figure 21:
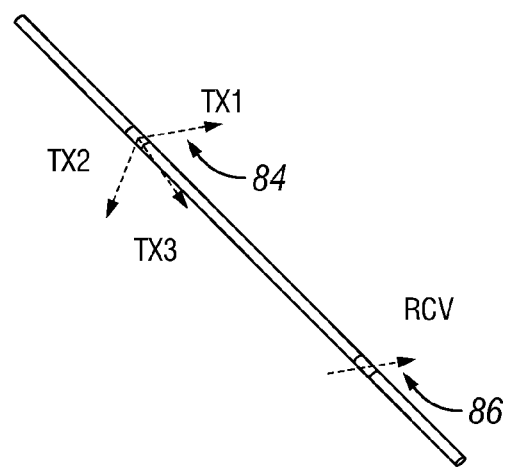
FIG. 21 is a schematic representation of a logging system example utilizing a three transmitter and receiver system, according to an alternate embodiment of the present invention.

Referring generally to the schematic illustration of FIG. 21, one example is provided for determining the calibrated measurement ZZ/(XX+YY). In this example, the calibrated measurement ZZ/(XX+YY) can be achieved with a logging system that uses three tilted TX antennas 84 coupled to a tilted RCV antenna 86. The received voltage at the receiver for each TX RCV pair has a constant term and a first and second harmonic term. When fitting the measurement with respect to the tool/bottom hole assembly rotation, the relative gain of the RCV channel is determined at the same time as the elementary coupling. In vertical wells or near vertical wells, the cross coupling terms are mostly zero, thereby having only constant behavior as a function of the tool azimuthal orientation (toolface), and therefore the individual relative gains cannot be extracted (gain can only be extracted from the first and second harmonics). To measure the relative gains when no first and second harmonic is present, a calibration of the receiver antennas can be applied using, for example, test coils embedded in the receiver antennas or other suitable electronics. In the example illustrated in FIG. 11, the basic three transmitter and receiver system is used to determine the elementary couplings. In this implementation, each transmitter and receiver pair is tilted at 45° with respect to the tool axis, and the TX magnetic moments are distributed azimuthally with an angle of 120° therebetween.

Figure 22:
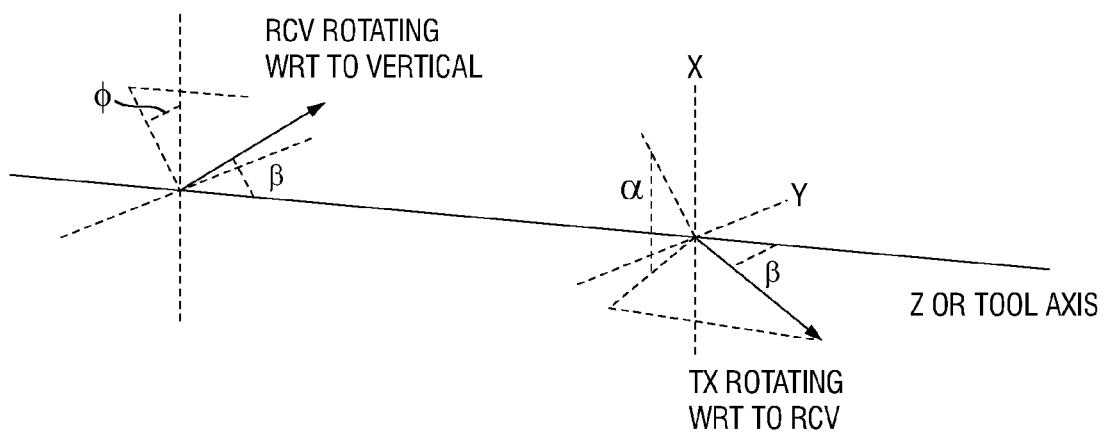
FIG. 22 is a graphical representation illustrating the use of tilted directional TX and RCV antennas, according to an embodiment of the present invention.

In the example illustrated in FIG. 22, the tilted directional TX and RCV antennas are illustrated as having certain magnetic dipole moments. The TX and RCV antennas are at a different azimuthal angle. In this example, a receiver signal is a function of elementary coupling and system orientation in matrix form as follows:

$$V_R = (\cos\alpha, \sin\alpha, 1) \cdot \begin{bmatrix} \cos\phi & \sin\phi & 0 \\ -\sin\phi & \cos\phi & 0 \\ 0 & 0 & 1 \end{bmatrix} \begin{bmatrix} XX & XY & XZ \\ YX & YY & YZ \\ ZX & ZY & ZZ \end{bmatrix} \begin{bmatrix} \cos\phi & -\sin\phi & 0 \\ \sin\phi & \cos\phi & 0 \\ 0 & 0 & 1 \end{bmatrix} \cdot \begin{pmatrix} 1 \\ 0 \\ 1 \end{pmatrix}$$

The RCV moment vector on the right is tilted at 45° and vertical. The TX moment is oriented with an azimuthal angle of α with respect to vertical. The angle ø corresponds to the rotation of the TX RCV pair/tool.

The receiver signal also can be described as a function of elementary coupling and system orientation where g is the transmitter receiver channel gain as follows:

$$\frac{V_R}{g} = ZZ + \frac{(XX+YY)}{2} \cdot \cos\alpha - \frac{(XY-YX)}{2} \cdot \sin\alpha +$$
$$ZX \cdot \cos\phi + ZY \cdot \sin\phi + XZ \cdot \cos(\alpha+\phi) + YZ \cdot \sin(\alpha+\phi) +$$
$$\frac{(XX-YY)}{2} \cdot \cos(\alpha+2\phi) + \frac{(XY+YX)}{2} \cdot \sin(\alpha+2\phi)$$

It should be noted that by using rotation, all couplings can be extracted. In the case of a true vertical well, only the constant term is present.

The receiver signal also can be described with respect to three tilted transmitter receiver pairs tilted at 45°, as follows:

$$V_{T1R} = g_{T1} \cdot \left( ZZ + \frac{(XX+YY)}{2} \cdot \cos\alpha_{T1} - \frac{(XY-YX)}{2} \cdot \sin\alpha_{T1} \right)$$
$$V_{T2R} = g_{T2} \cdot \left( ZZ + \frac{(XX+YY)}{2} \cdot \cos\alpha_{T2} - \frac{(XY-YX)}{2} \cdot \sin\alpha_{T2} \right)$$
$$V_{T3R} = g_{T3} \cdot \left( ZZ + \frac{(XX+YY)}{2} \cdot \cos\alpha_{T3} - \frac{(XY-YX)}{2} \cdot \sin\alpha_{T3} \right)$$

The receiver moment is oriented vertically with each TX antenna at a specific azimuthal angle $\alpha_{T1}$, $\alpha_{T2}$, $\alpha_{T3}$ with respect to vertical. Each TX RCV pair has an associated gain $g_{T1}$, $g_{T2}$, $g_{T3}$. ZZ, XX+YY and XY−YX can be calculated from the equations above only if the gains or at least the relative gains are known.

In FIGS. 23-30, examples are provided in graphical form of look-ahead sensitivity to two-step changes in resistivity with respect to spacing attenuation and phase shift. A reasonable cut off of 0.1 dB for attenuation and 0.25 degree phase shift can be assumed. The look-ahead depth of investigation is dependent on the transmission frequency resulting in a lower range at higher frequency. The phase shift response is deeper (for both resistivity profiles) than attenuation because of the presence of a lobe. The lobe increases with frequency. Combination attenuation and phase shift measurements at different frequencies can be used in a way similar to the look-around inversion.

Figure 23:
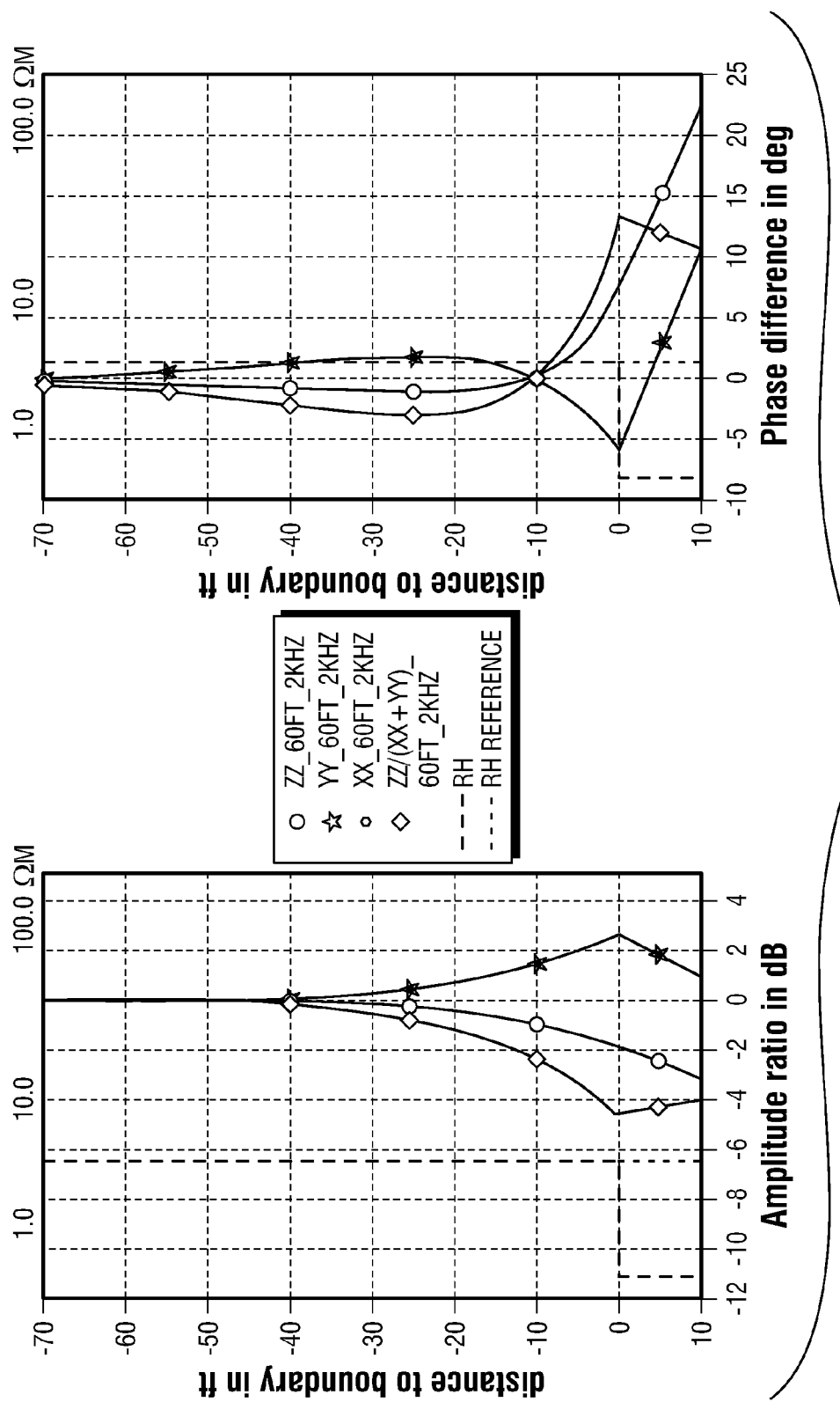
FIG. 23 is a graphical representation of results output by one example of the logging system illustrating tool sensitivity related to a step down resistivity profile for a given set of parameters, according to an embodiment of the present invention.

In FIG. 23, the example graphically illustrated is for a 2 kHz embodiment with a 60 foot TX RCV spacing attenuation in the left graph and illustrated phase shift in the right graph. The graphs represent induction 60 foot 2 kHz tool sensitivity to a step down resistivity profile (2 Ωm to 0.3 Ωm). A cut-off of 0.1 dB for attenuation and 0.25 degree for phase shift has been applied. The wider curves on the graph show the region of detection. In this example, the attenuation is illustrated as having a range of about 40 feet ahead of the lowest EM antenna. The phase shift, on the other hand, has a deeper range but with the presence of a lobe.

Figure 24:
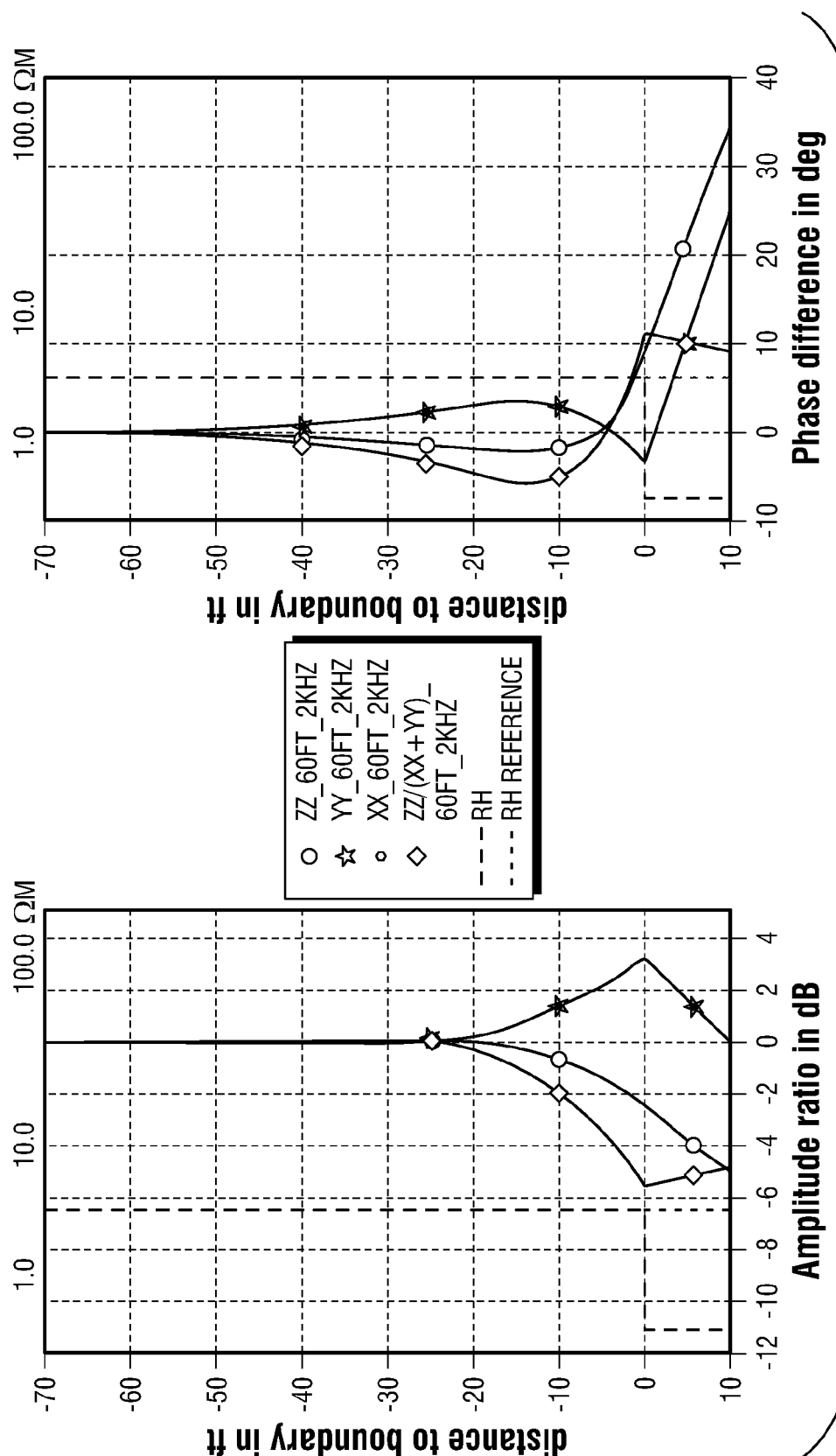
FIG. 24 is another graphical representation of results output by one example of the logging system illustrating tool sensitivity related to a step down resistivity profile for another set of parameters, according to an embodiment of the present invention.

In FIG. 24, another example is graphically illustrated and represents induction 60 foot 5 kHz tool sensitivity to a step down resistivity profile (2 Ωm to 0.3 Ωm). A cut-off of 0.1 dB for attenuation and 0.25 degree for phase shift has been applied. The wider curves on the graph show the region of detection. In this example, the range is reduced in both attenuation and phase shift.

Figure 25:
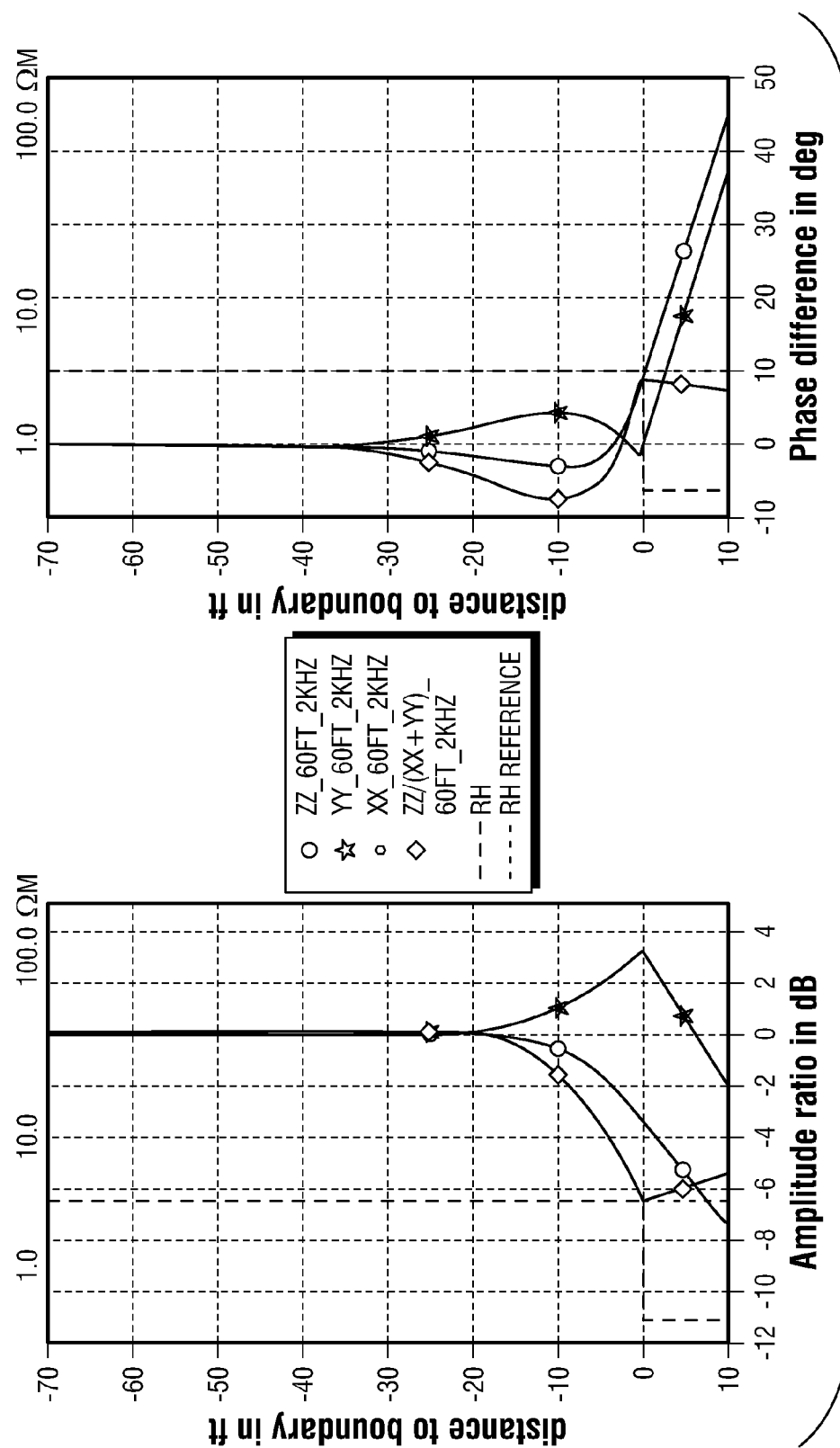
FIG. 25 is another graphical representation of results output by one example of the logging system illustrating tool sensitivity related to a step down resistivity profile for another set of parameters, according to an embodiment of the present invention.

In FIG. 25, another example is graphically illustrated and represents induction 60 foot 10 kHz tool sensitivity to a step down resistivity profile (2 Ωm to 0.3 Ωm). A cut-off of 0.1 dB for attenuation and 0.25 degree for phase shift has been applied. The wider curves on the graph show the region of detection. In this example, a decrease in the range is illustrated with a lobe starting to appear in the attenuation.

Figure 26:
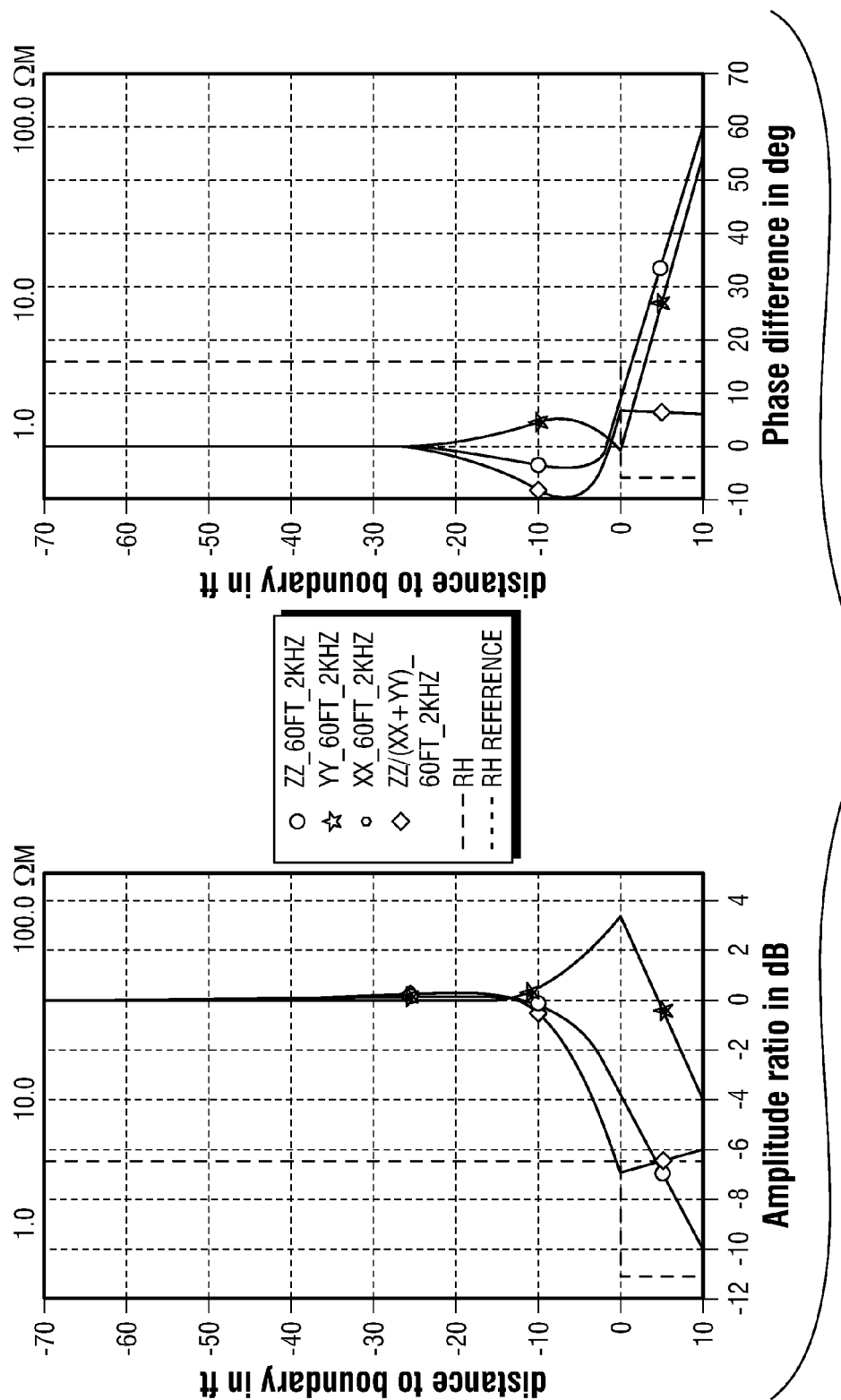
FIG. 26 is another graphical representation of results output by one example of the logging system illustrating tool sensitivity related to a step down resistivity profile for another set of parameters, according to an embodiment of the present invention.

In FIG. 26, another example is graphically illustrated and represents induction 60 foot 20 kHz tool sensitivity to a step down resistivity profile (2 Ωm to 0.3 Ωm). A cut-off of 0.1 dB for attenuation and 0.25 degree for phase shift has been applied. The wider curves on the graph show the region of detection.

Figure 27:
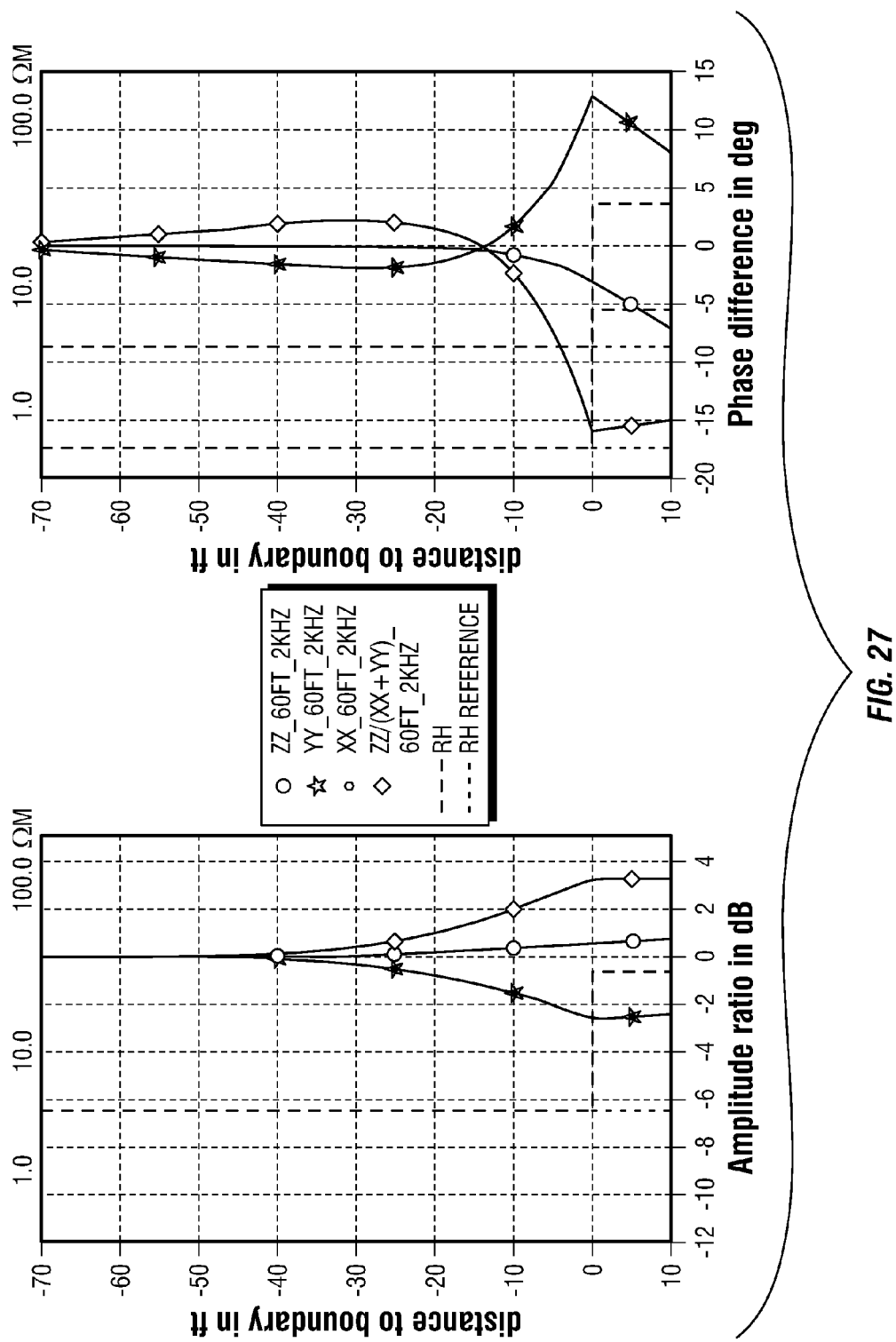
FIG. 27 is another graphical representation of results output by one example of the logging system illustrating tool sensitivity related to a step up resistivity profile for a given set of parameters, according to an embodiment of the present invention.

In FIG. 27, another example is graphically illustrated and represents induction 60 foot 2 kHz tool sensitivity to a step up resistivity profile (2 Ωm to 20 Ωm). A cut-off of 0.1 dB for attenuation and 0.25 degree for phase shift has been applied. The wider curves on the graph show the region of detection. A step up profile is similar to a step down profile as in the examples illustrated and described above.

Figure 28:
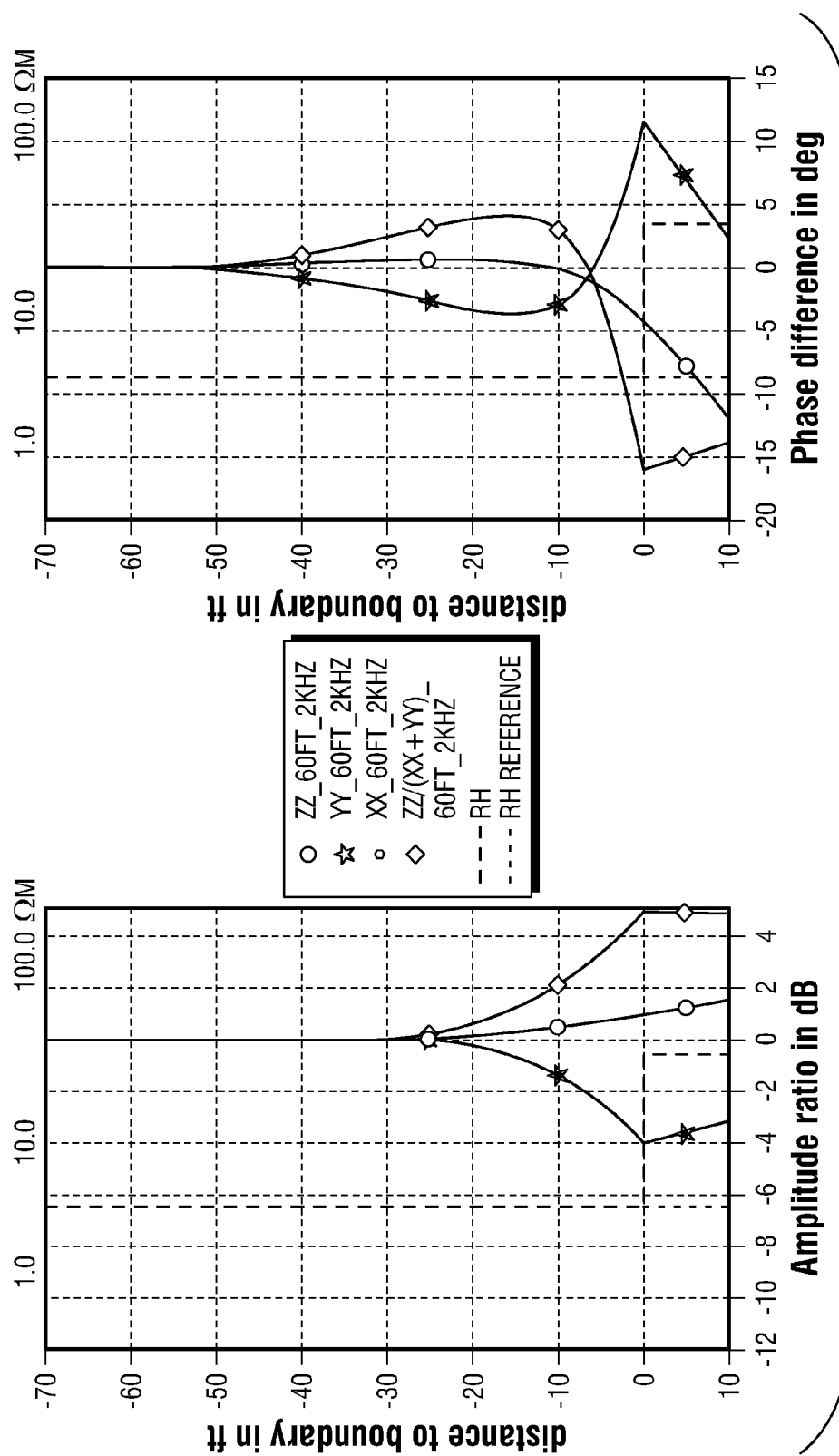
FIG. 28 is another graphical representation of results output by one example of the logging system illustrating tool sensitivity related to a step up resistivity profile for another set of parameters, according to an embodiment of the present invention.

In FIG. 28, another example is graphically illustrated and represents induction 60 foot 5 kHz tool sensitivity to a step up resistivity profile (2 Ωm to 20 Ωm). A cut-off of 0.1 dB for attenuation and 0.25 degree for phase shift has been applied. The wider curves on the graph show the region of detection.

Figure 29:
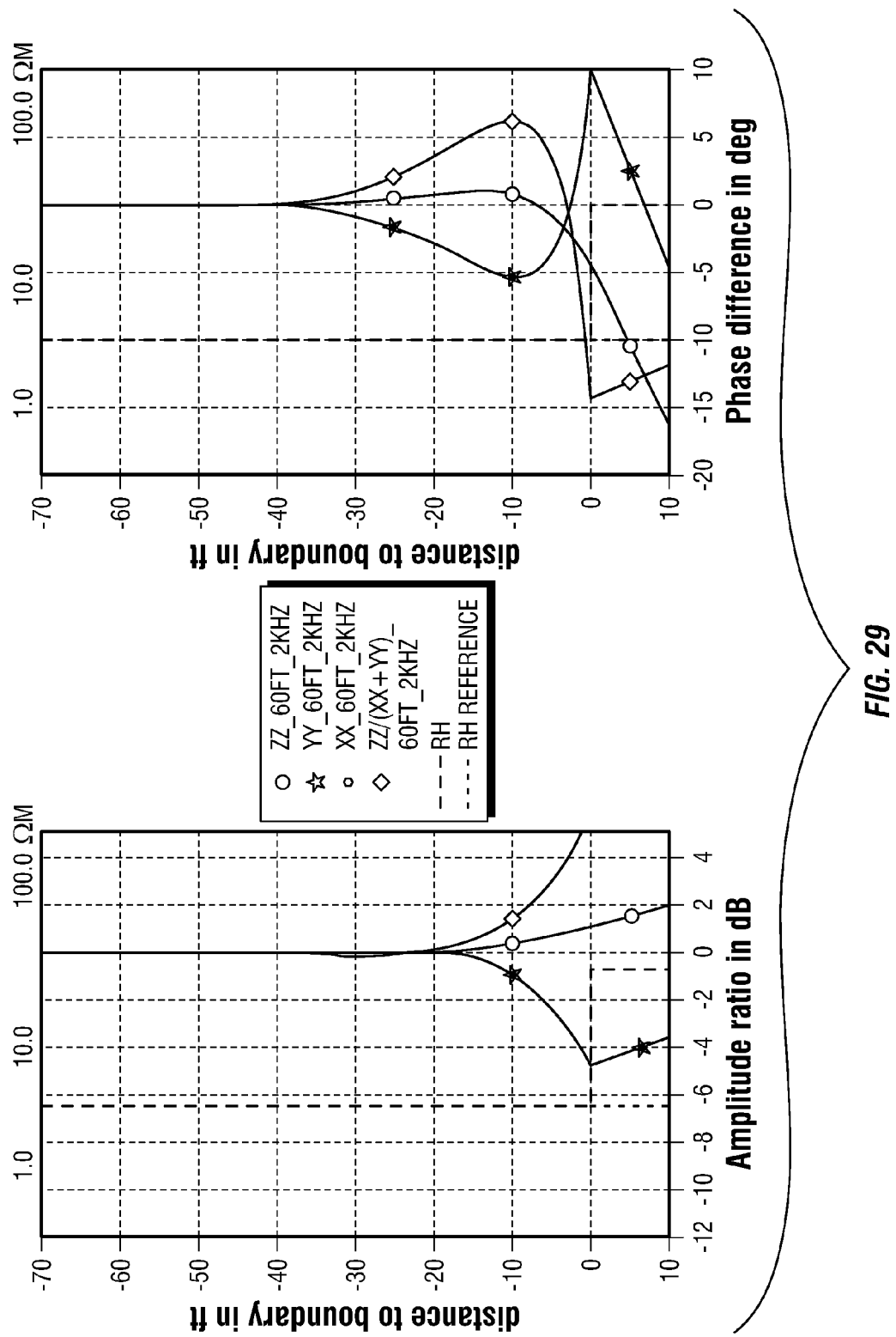
FIG. 29 is another graphical representation of results output by one example of the logging system illustrating tool sensitivity related to a step up resistivity profile for another set of parameters, according to an embodiment of the present invention.

In FIG. 29, another example is graphically illustrated and represents induction 60 foot 10 kHz tool sensitivity to a step up resistivity profile (2 Ωm to 20 Ωm). A cut-off of 0.1 dB for attenuation and 0.25 degree for phase shift has been applied. The wider curves on the graph show the region of detection.

Figure 30:
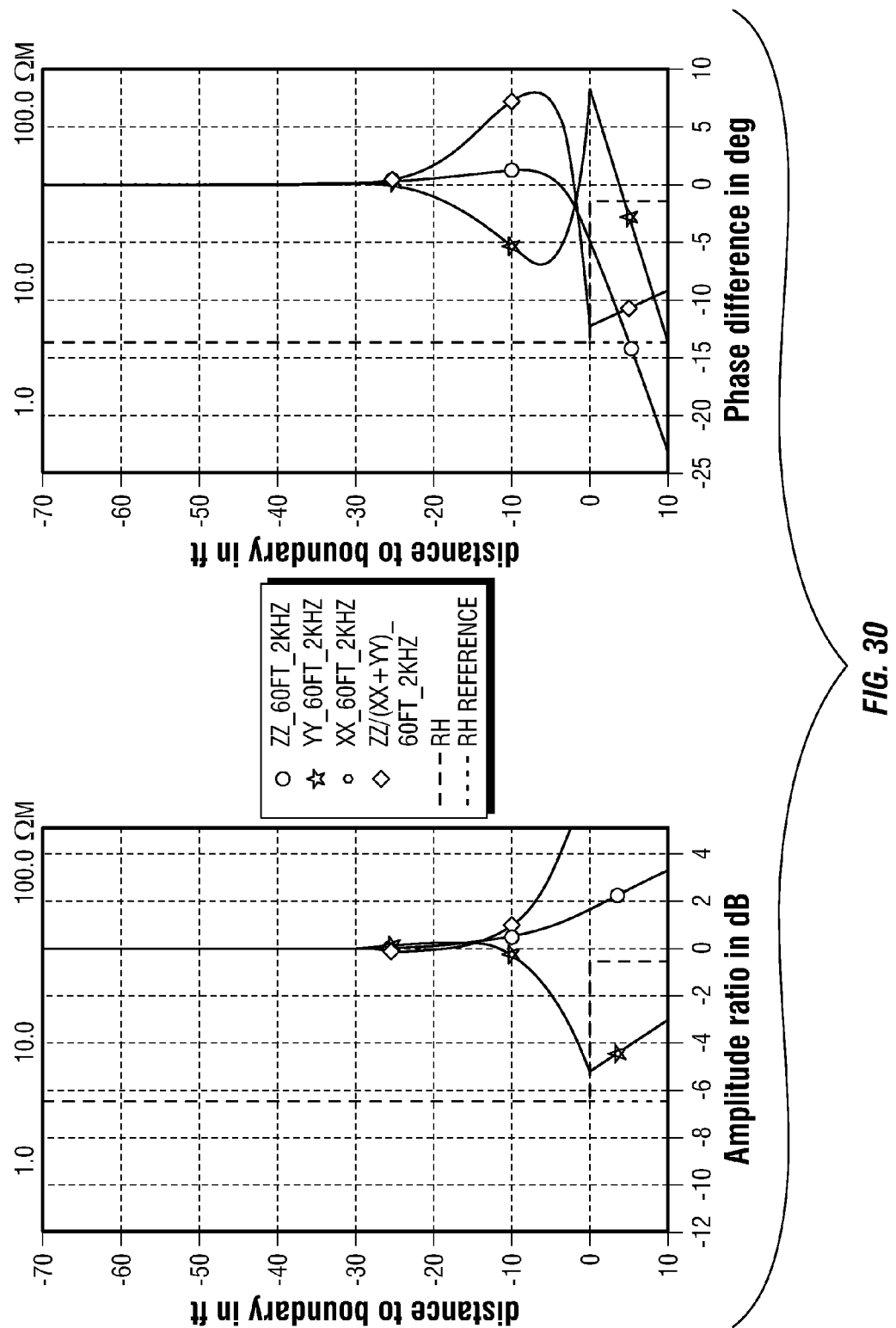
FIG. 30 is another graphical representation of results output by one example of the logging system illustrating tool sensitivity related to a step up resistivity profile for another set of parameters, according to an embodiment of the present invention.

In FIG. 30, another example is graphically illustrated and represents induction 60 foot 20 kHz tool sensitivity to a step up resistivity profile (2 Ωm to 20 Ωm). A cut-off of 0.1 dB for attenuation and 0.25 degree for phase shift has been applied. The wider curves on the graph show the region of detection. Similar to the step down profile examples, the illustrated range is inversely proportional to frequency.

Figure 31A:
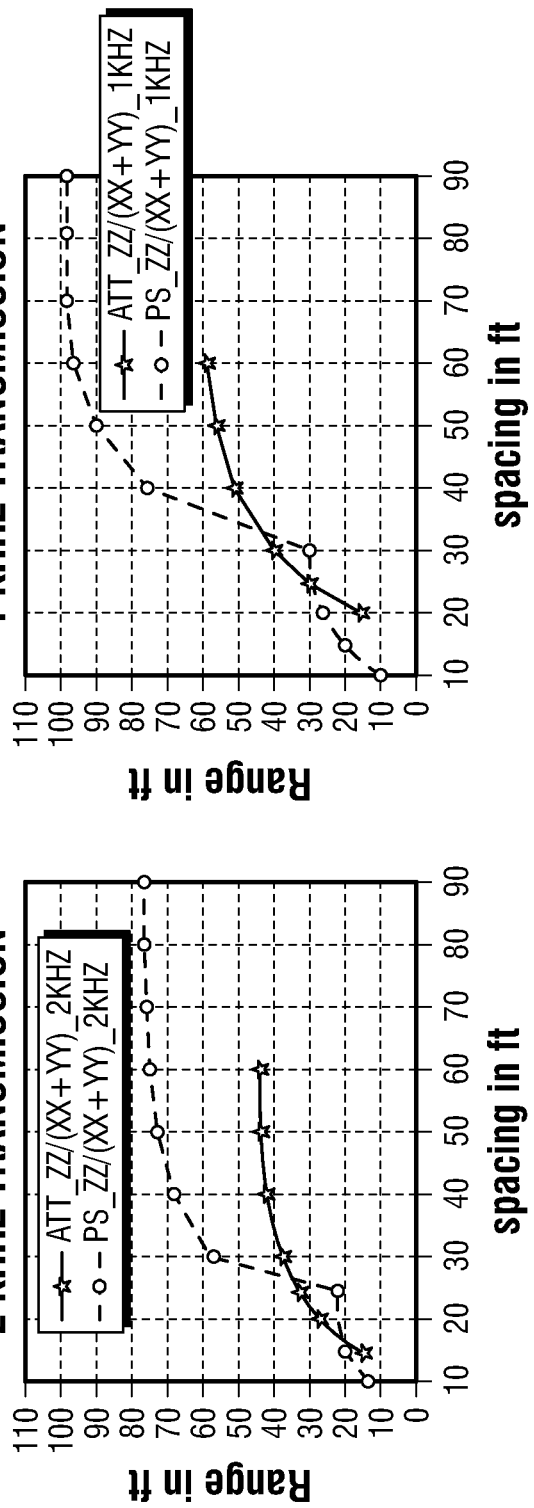
FIG. 31 is a graphical representation of look ahead range versus TX RCV spacing for attenuation and phase shift with respect to both step up and step down resistivity profiles, according to an embodiment of the present invention.
Figure 31B:
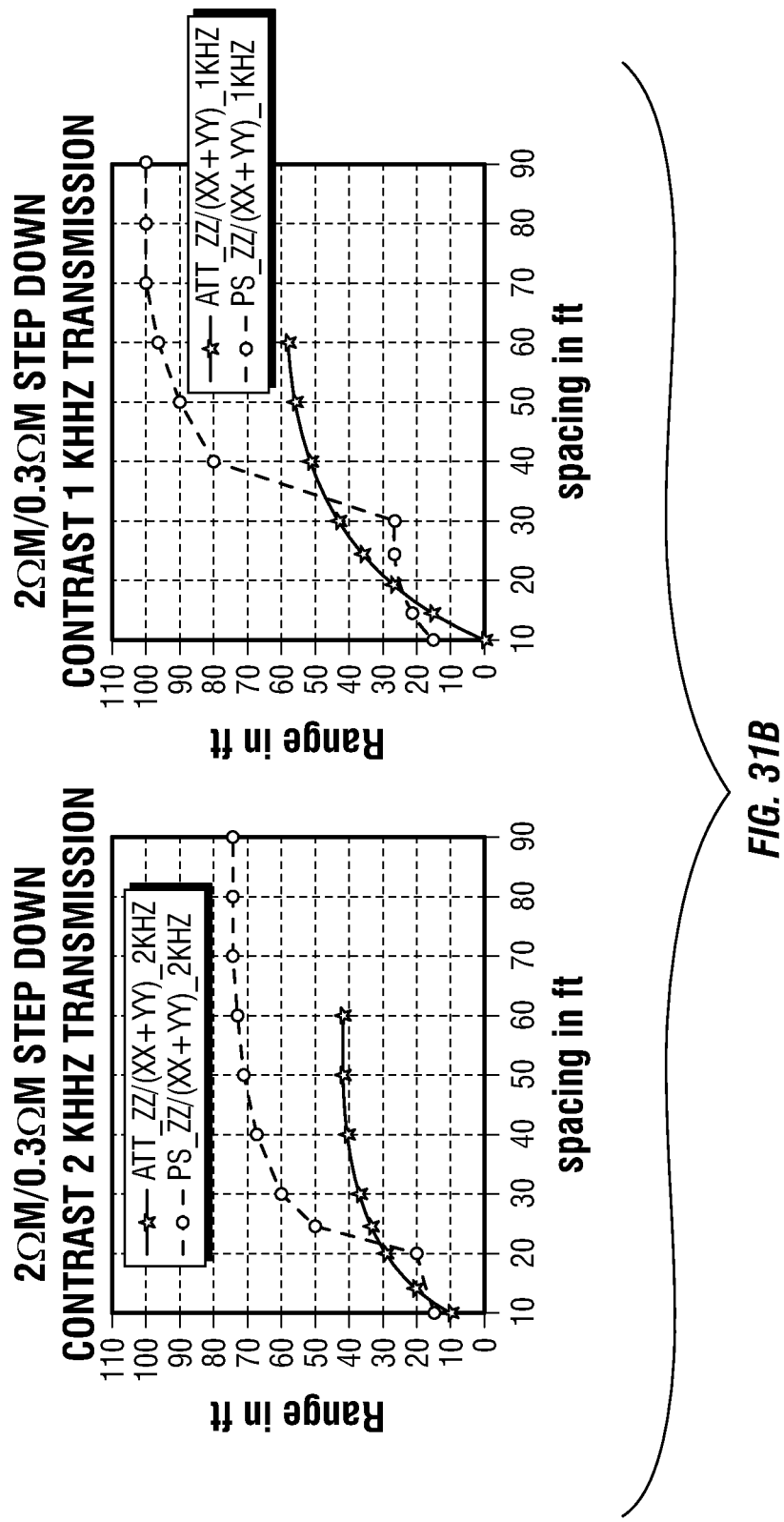

By using the cut-offs described above and varying the T-R spacing, the look-ahead range for the ZZ/(XX+YY) attenuation and phase shift can be represented graphically, as illustrated in FIG. 31. As shown in the graphs of FIG. 31, the examples utilize two transmission frequencies at 1 kHz or 2 kHz. As demonstrated, the range reaches a plateau for longer T-R spacing because of the cut-off parameters. To further increase the range, a lower frequency can be utilized as illustrated in the right side graphs of FIG. 31. The graphs provide examples of a look-ahead range versus TX RCV spacing for attenuation and phase shift with respect to step up and step down resistivity profiles at 2 kHz and 1 kHz.

The range also is dependent on a contrast ratio and resistivity level. In FIG. 32, for example, graphical representations are provided at 2 kHz and 5 kHz attenuation for a step down formation profile at different levels of resistivity and different resistivity contrast with respect to the top resistivity. Each transmission frequency has an optimal resistivity level (resistivity around the bottom hole assembly or a resistivity top)

where the higher frequency has a more optimum range for the higher resistivity level. A higher contrast results in a better range at all frequencies. Also, the 10 Ωm and 20 Ωm resistivity tops show the best range characteristics for 2 kHz and 5 kHz, respectively. Raising the transmission frequency enables higher resistivity. A cut-off of 0.1 dB for attenuation and 0.25 degree for phase shift has been applied. The wider curves on the graph show the region of detection. In this example, the range is reduced in both attenuation and phase shift.

Figure 33A:
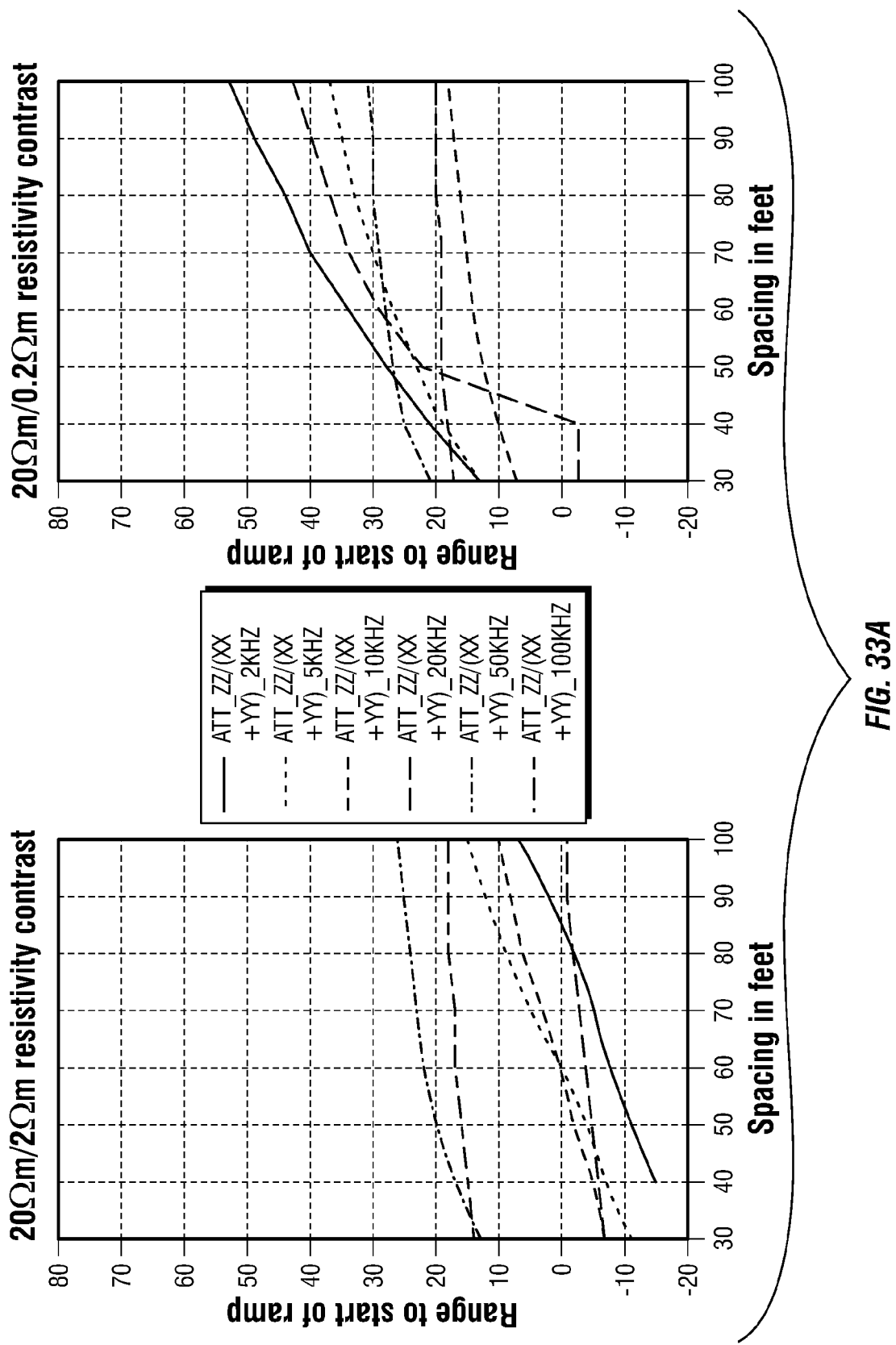
FIG. 33 is a graphical representation illustrating detection range and step down resistivity profiles at two resistivity contrasts, according to an embodiment of the present invention.
Figure 33B:
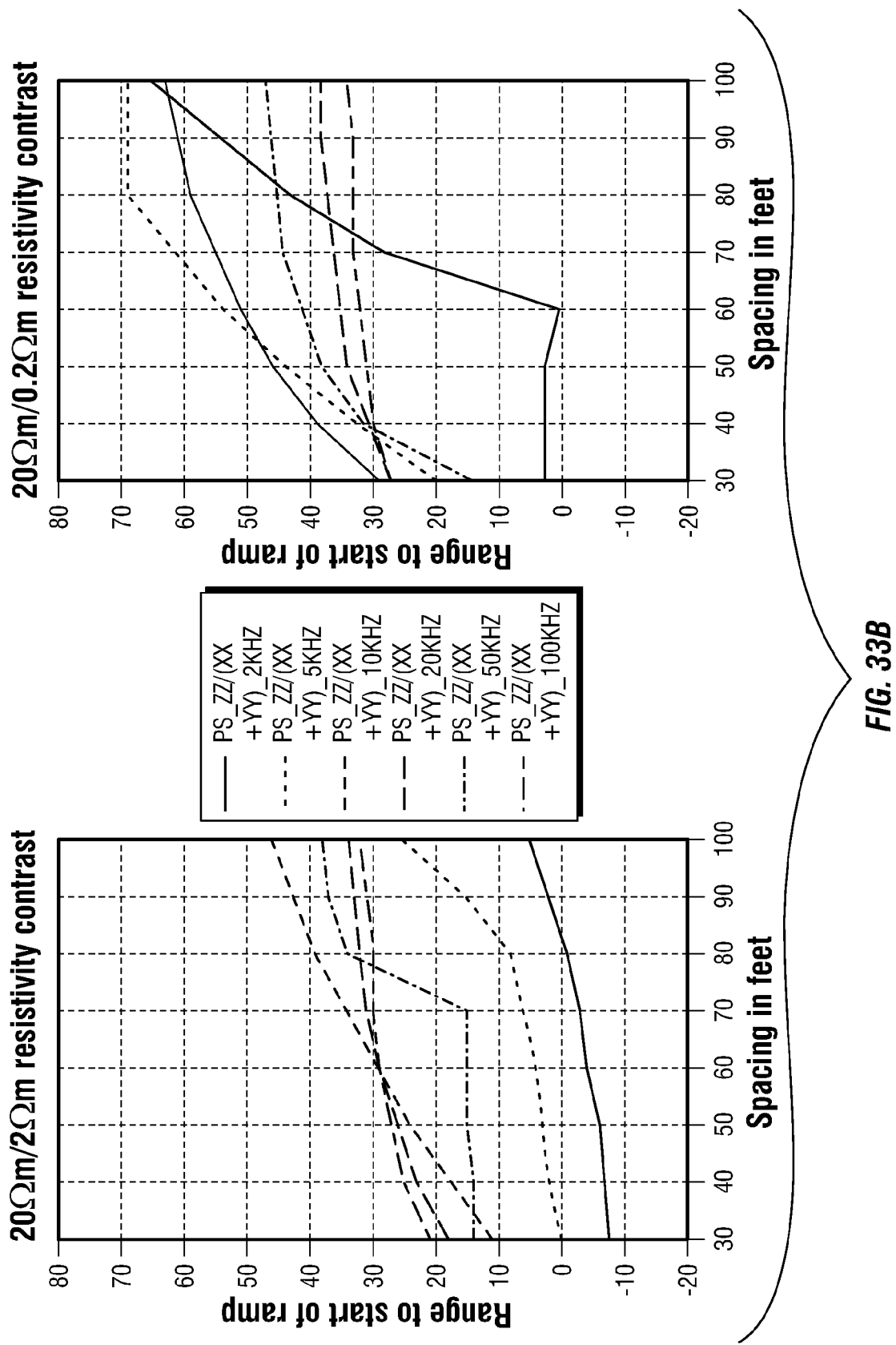
Figure 34A:
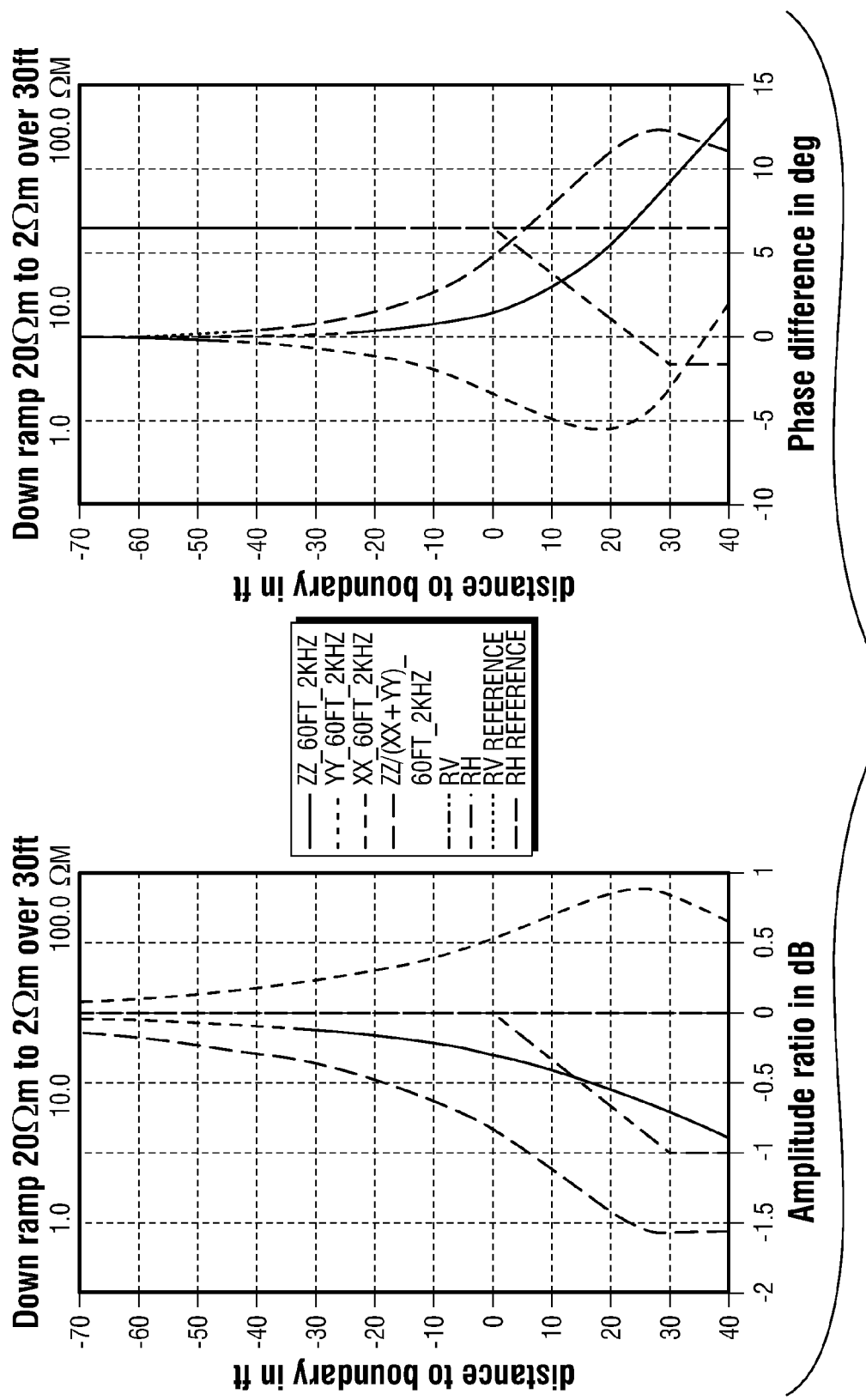
FIG. 34 is a graphical illustration providing examples of step down profiles and other information related to utilization of one example of the logging system, according to an embodiment of the present invention.
Figure 34B:
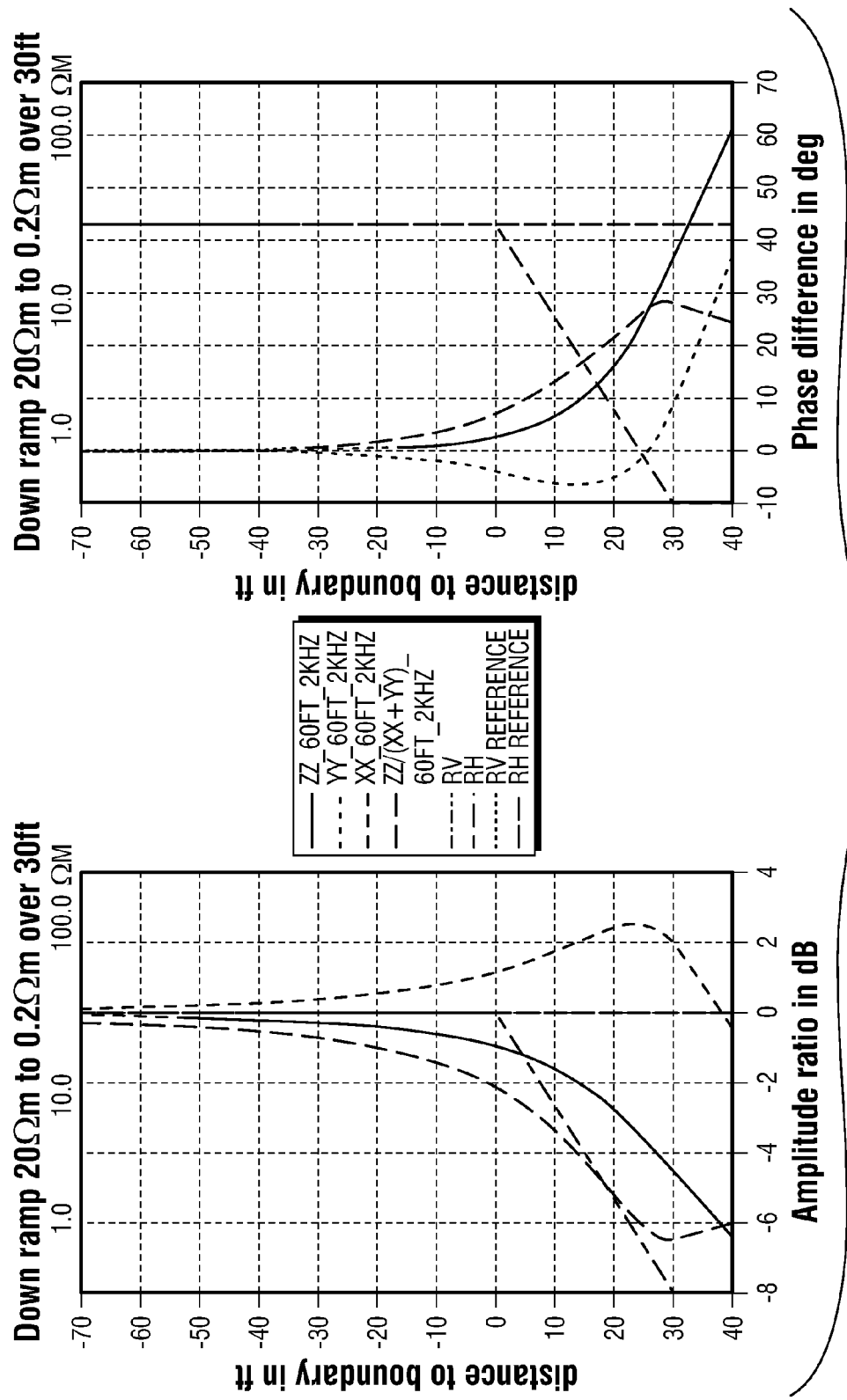
Figure 34C:
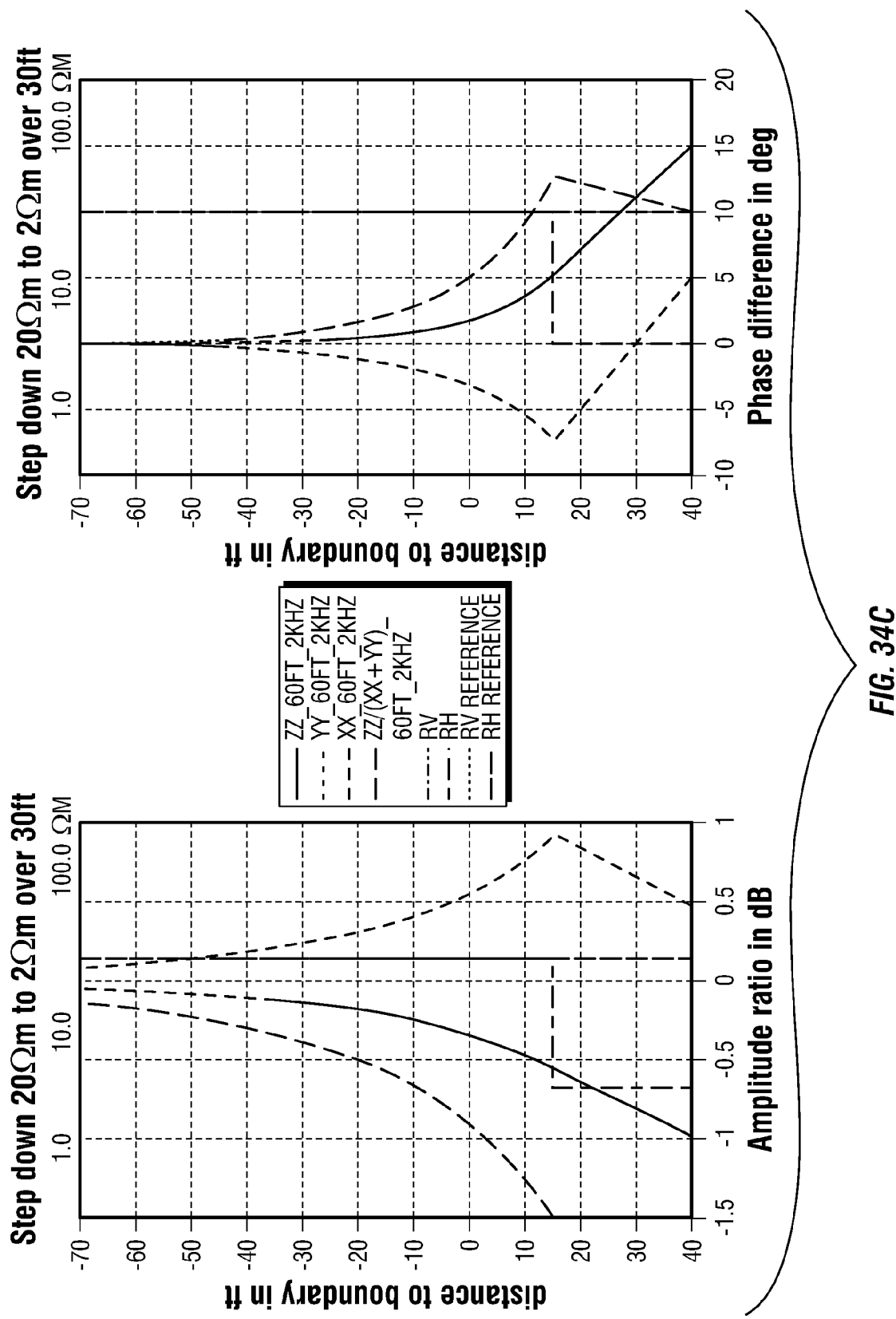
Figure 34D:
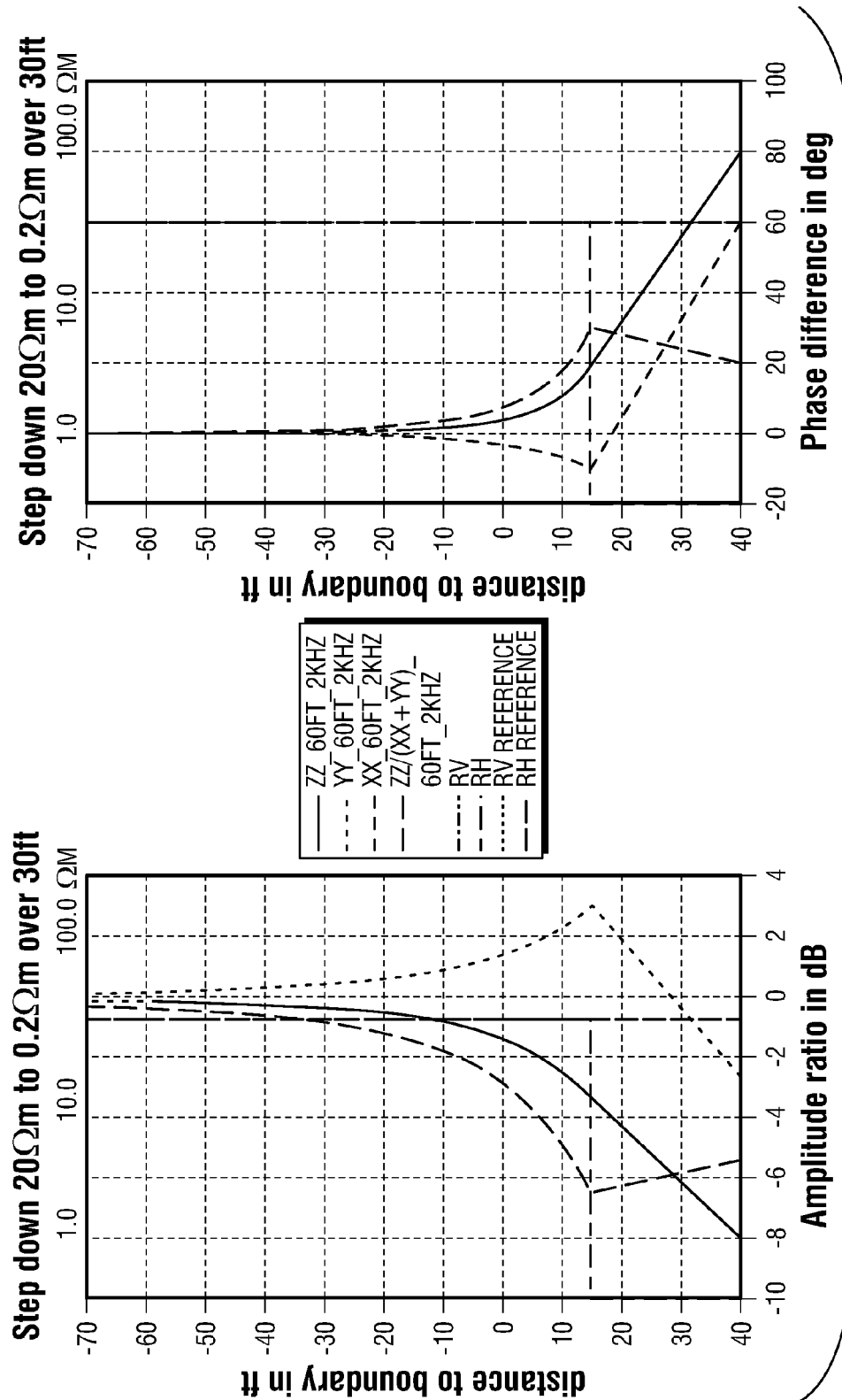
Figure 34E:
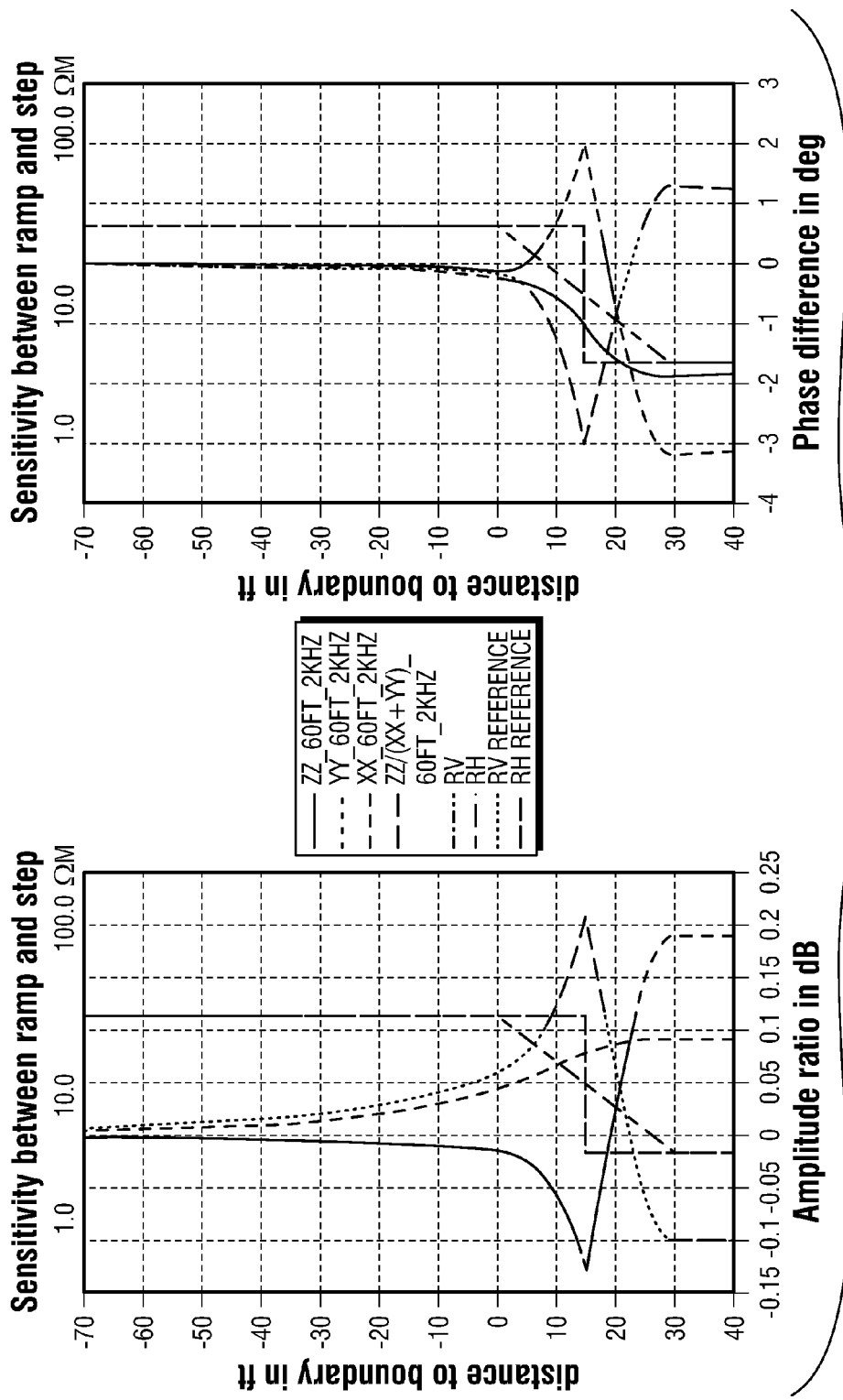
Figure 34F:
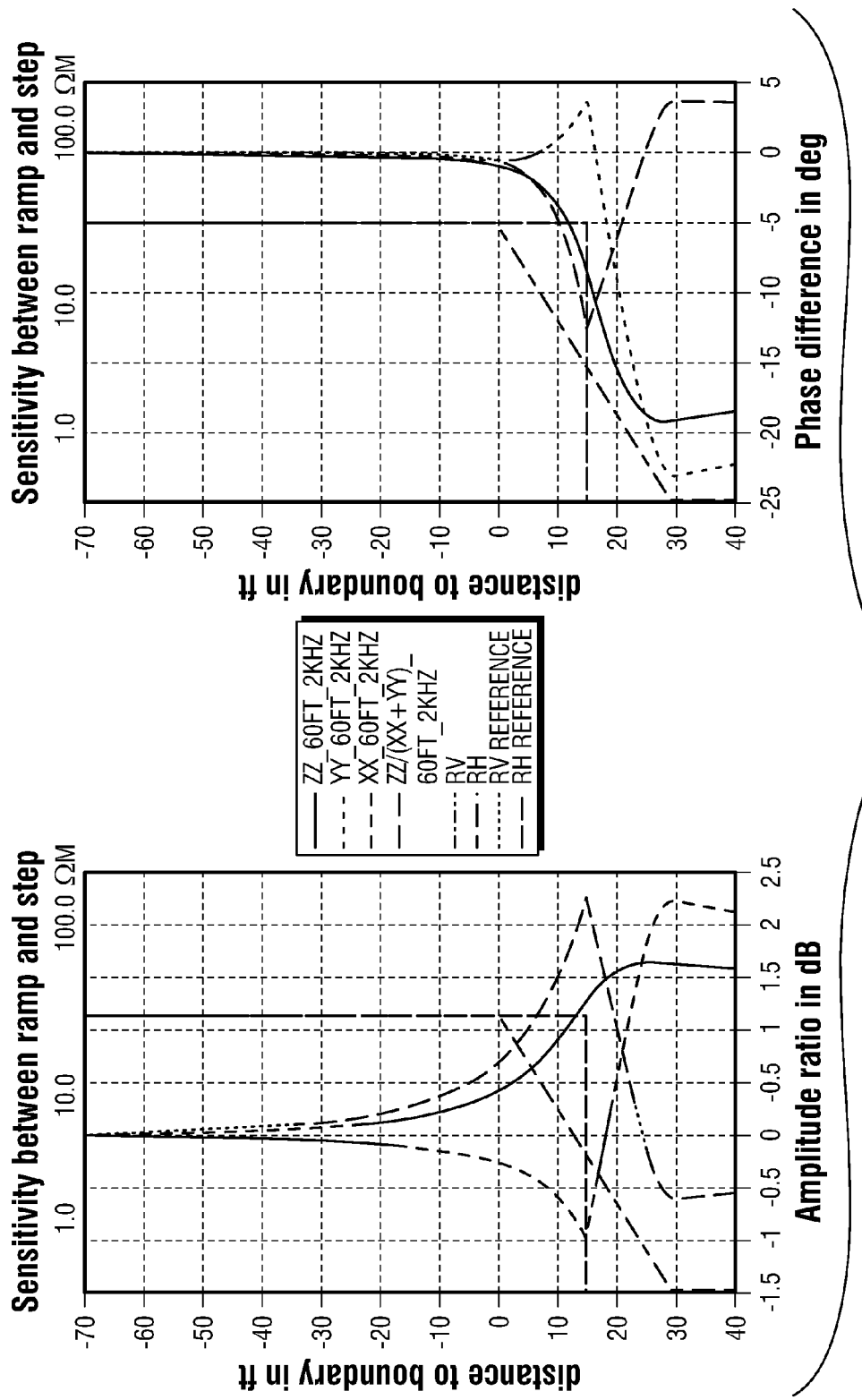
Figure 35A:
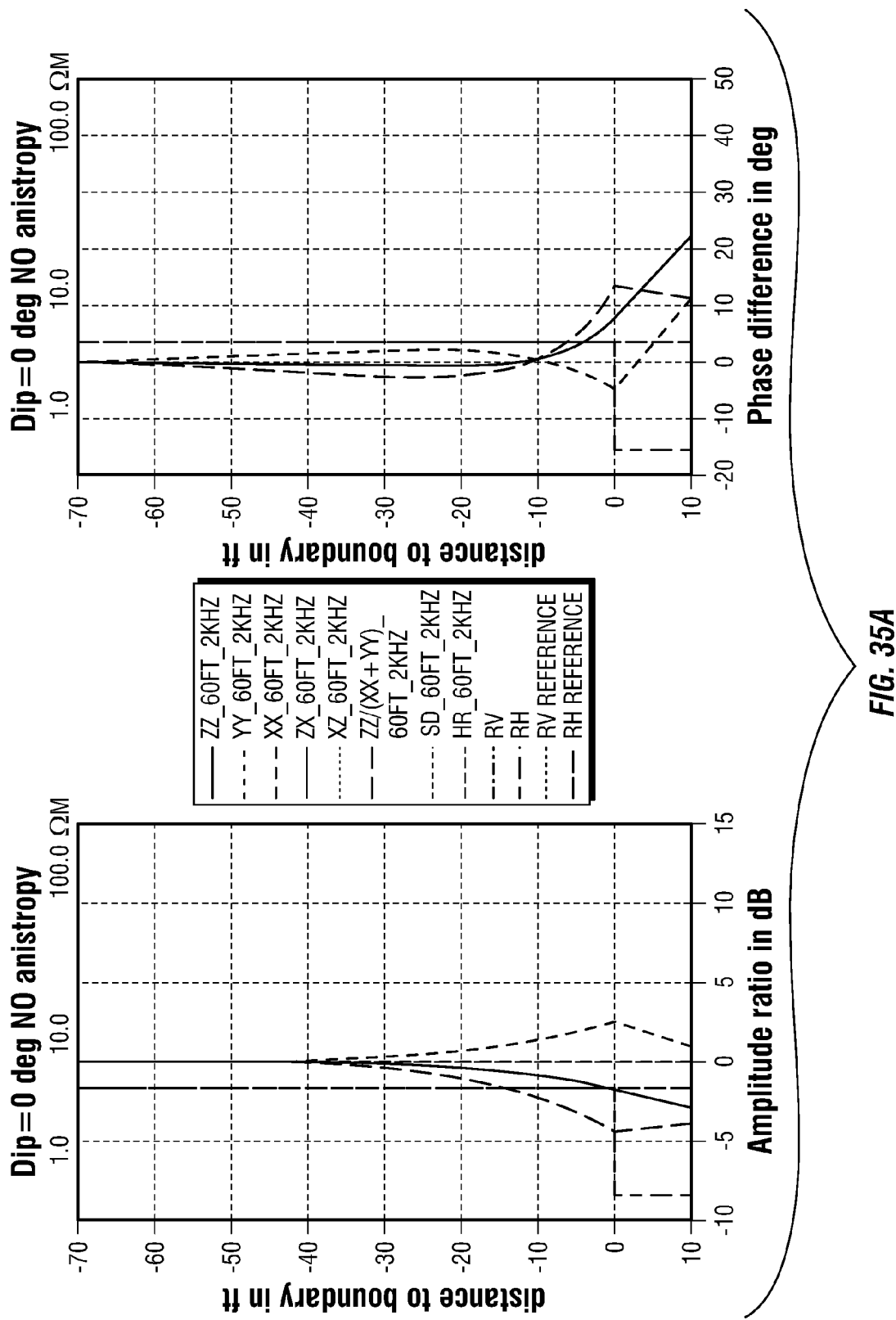
FIG. 35 is a graphical representation illustrating examples of results that can be obtained utilizing the logging system related to anisotropy and relative dip of the formation, according to an embodiment of the present invention.
Figure 35B:
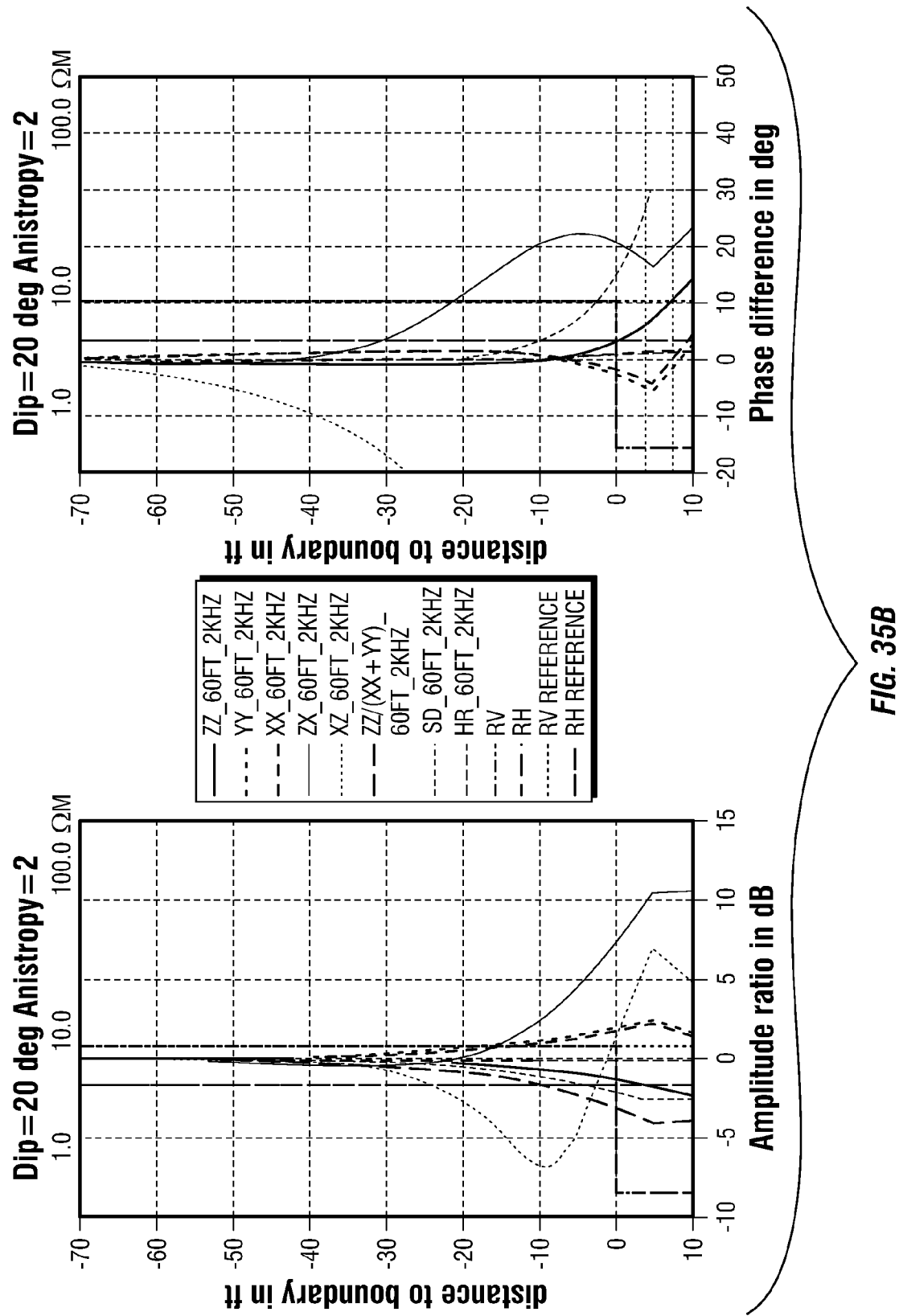
Figure 35C:
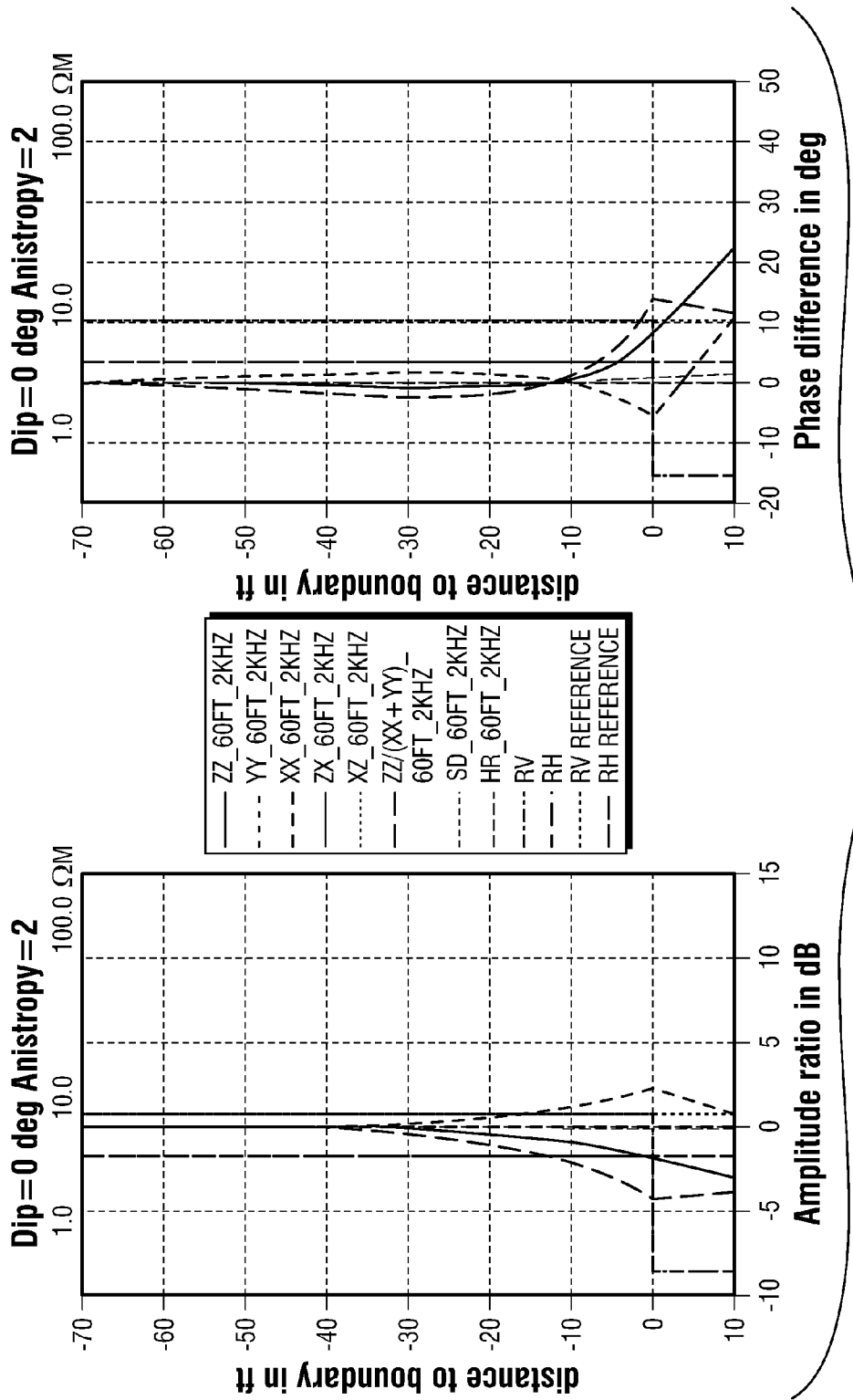
Figure 35D:
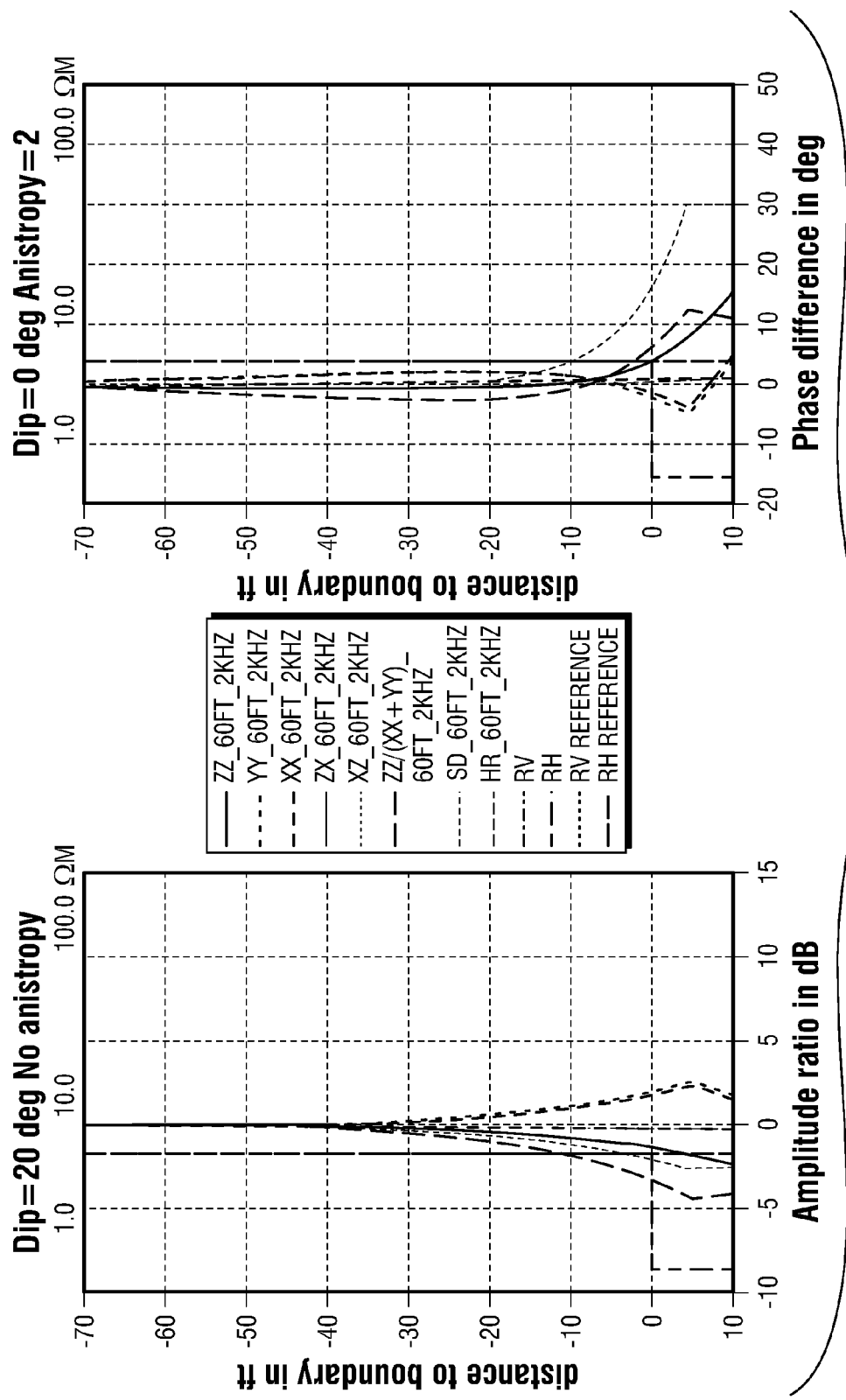
Figure 36A:
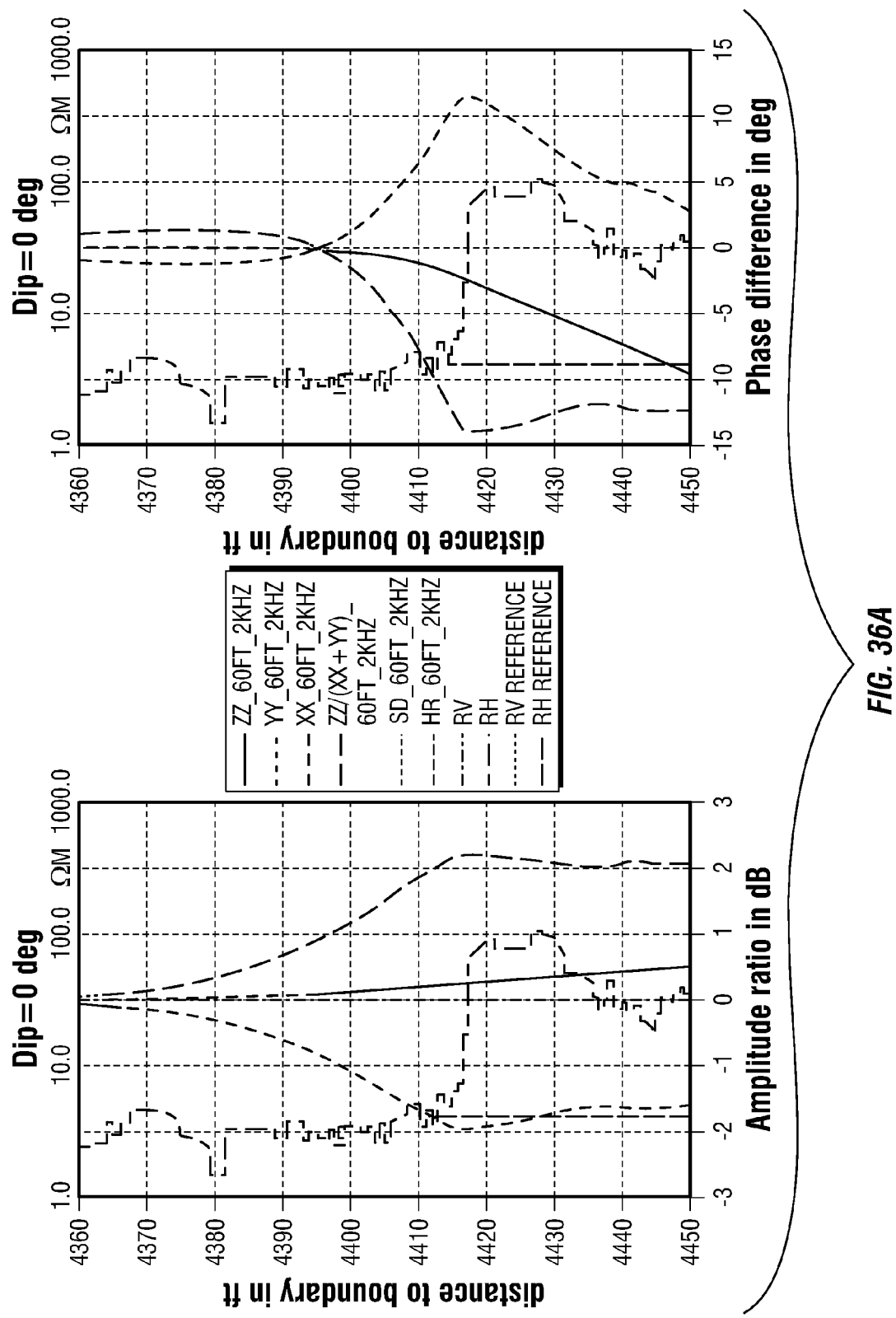
FIG. 36 is a graphical representation illustrating examples of measurements as a function of four different structural dips, according to an embodiment of the present invention.
Figure 36B:
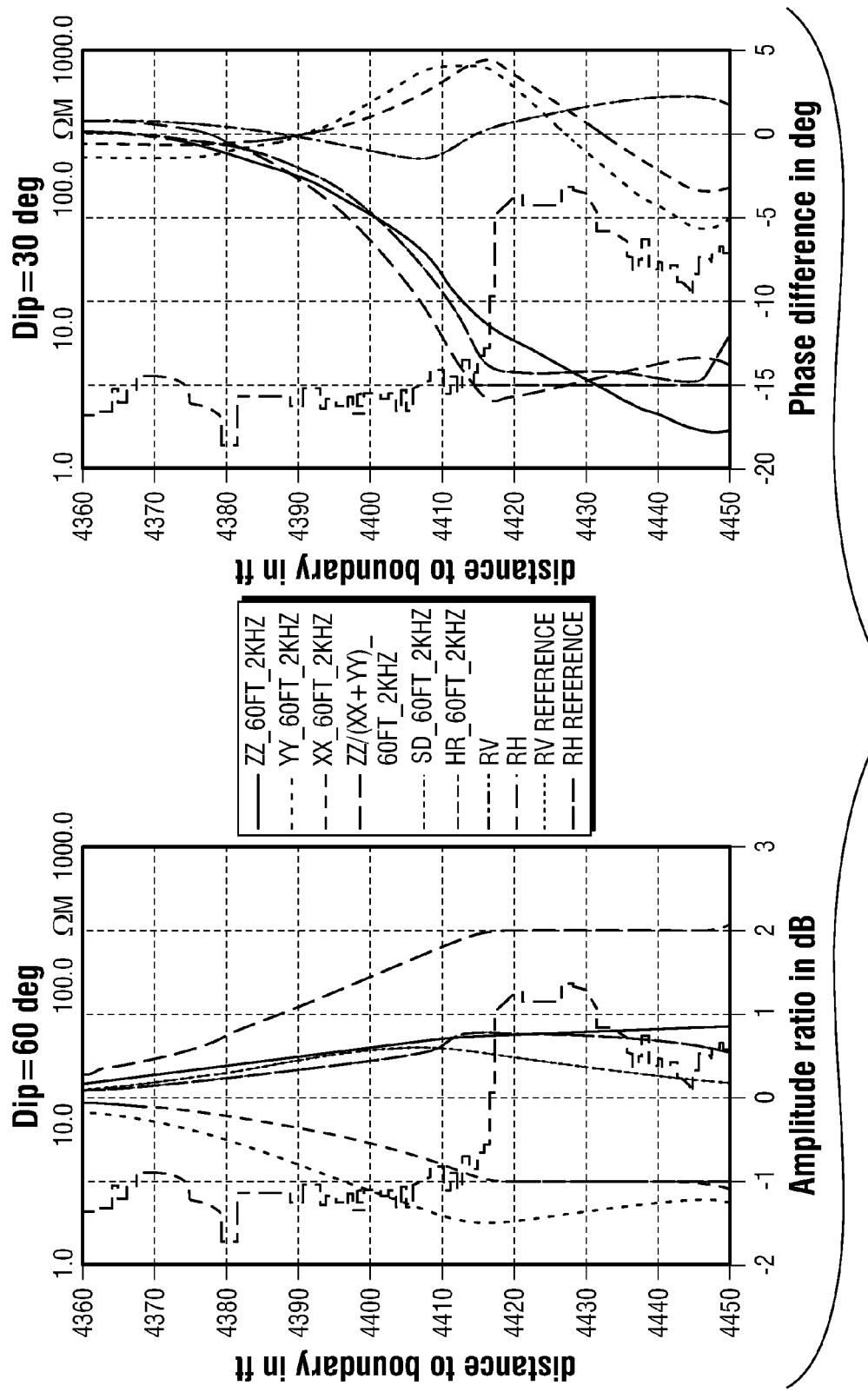
Figure 36C:
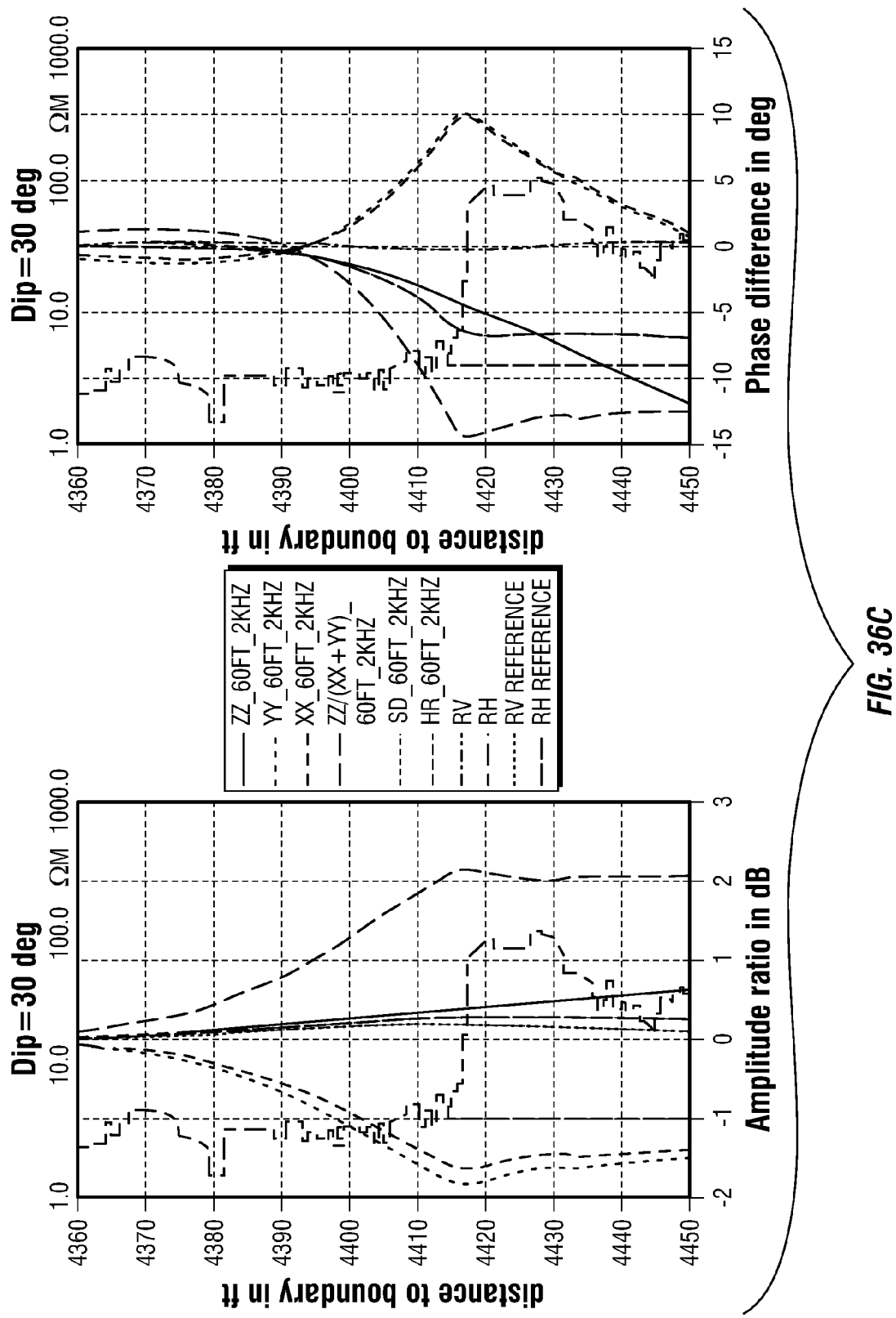
Figure 36D:
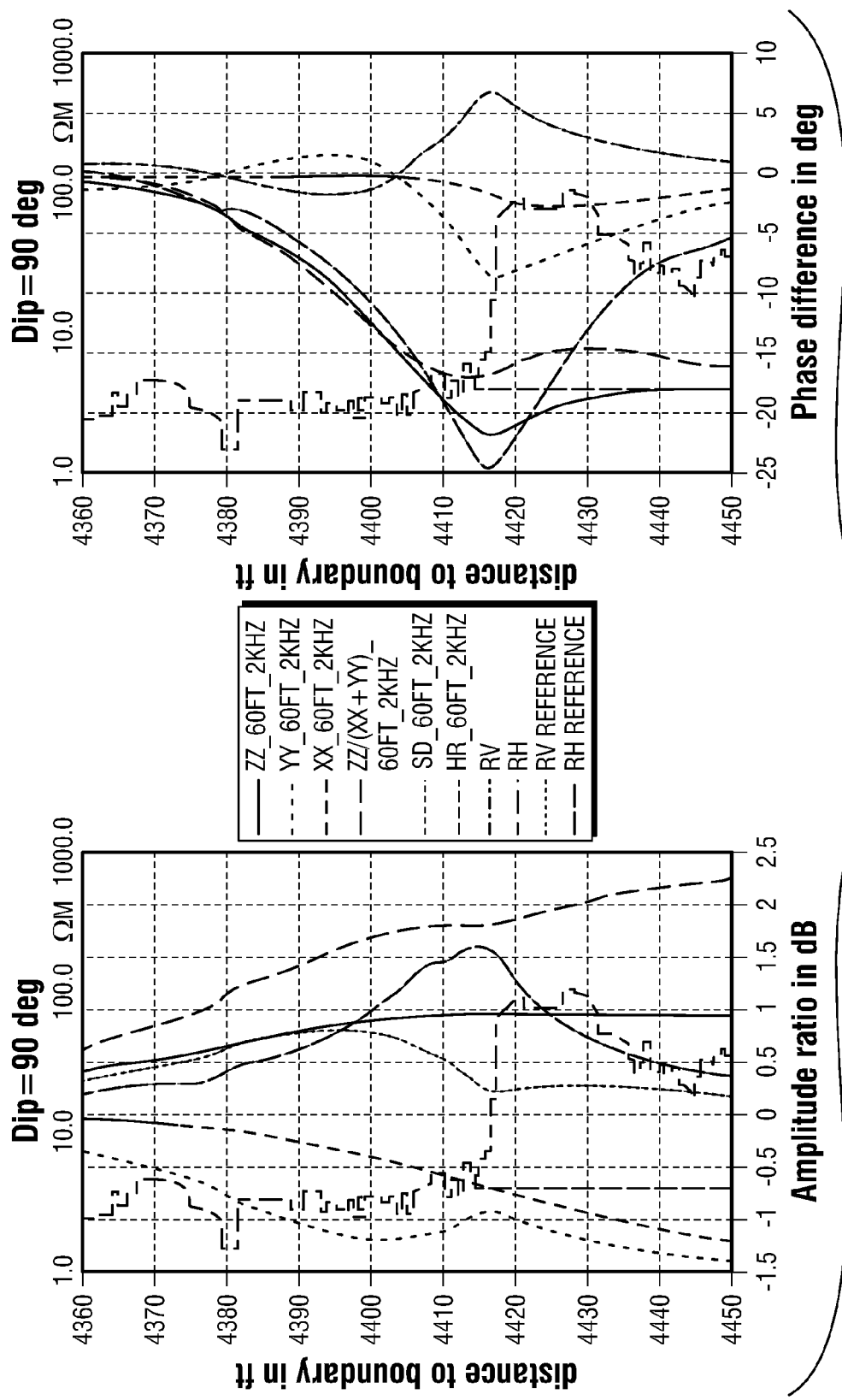

In logging while drilling applications, it can be important to be able to discriminate between a step change in resistivity and a gradual ramp increase or decrease in resistivity ahead of the drill bit 66. Referring generally to FIG. 33, graphical representations are provided to illustrate look-ahead step functions and ramp discriminations. The graphical representations help describe the sensitivity of logging while drilling system 44 with respect to look-ahead sensitivity to a resistivity ramp profile versus step profile.

The graphical representations in FIG. 33 are based on the detection range for a 30 foot down ramp and step down resistivity profile at two resistivity contrasts of 20 Ωm/2 Ωm and 20 Ωm/0.2 Ωm. In this example, the step down profile is shifted in depth to a location at half the ramp size. The examples/representations are provided for a range of TX RCV spacing (e.g. 30 feet to 100 feet) and a range of frequencies (e.g. 2, 5, 10, 20, 50, and 100 kHz). The range is taken as the earliest distance to the start of the ramp. For each contrast, the range corresponds to a smaller fraction of the TX RCV spacing. With the long spacing, the look-ahead discrimination of the ramp versus step may be available only for some frequencies. It should be noted that range variation as a function of frequency can be rather complex due to the presence of a second lobe at higher frequencies.

In FIG. 34, additional examples are provided in the form of graphical representations. FIG. 34 provides two examples corresponding to a contrast ratio of 10 and 100 with 60 foot spacing at 2 kHz. Moving from left to right along the graphical representations of FIG. 34, a 30 foot ramp is illustrated with respect to a homogeneous formation, a step down profile is provided at a midpoint of the ramp with respect to the homogeneous formation, and finally a ramp is illustrated with respect to the step down profile for different elementary coupling combinations.

The logging while drilling system 44 also provides look ahead sensitivity to a resistivity step profile with respect to an anisotropic formation and non-zero structural dip. As illustrated by the graphical representations of FIG. 35, the anisotropy and relative dip of the formation, for which the look-ahead data collection is performed by the logging while drilling system 44, does not noticeably change the behavior of the diagonal term of the elementary coupling matrix. ZZ/(XX+YY) is a good combination measurement to use in many applications. With dip and/or anisotropy, the cross couplings XZ and ZX are non-zero, so the standard symmetrized directional measurements (ZZ+ZX)/(ZZ−ZX)*(ZZ−XZ)/(ZZ+XZ) also can be used in obtaining the look-ahead information.

The look-ahead and look-around capabilities of the logging system as a function of structural dip are illustrated in the graphical representations of FIG. 36. In FIG. 36, examples are provided for looking at measurements as a function of four different structural dips (0° or vertical, 30°, 60°, and 90° or horizontal). As illustrated in the graphical representations, the XX and YY measurements have a pronounced horn effect in vertical wells, but the YY and ZZ measurements are affected in horizontal wells. ZZ/(XX+YY) provides a good measurement valid for all of the angles. Such a measurement does not contain the directional information that the other directional measurements (i.e., the first and second harmonic directional measurements) have.

Figure 37A:
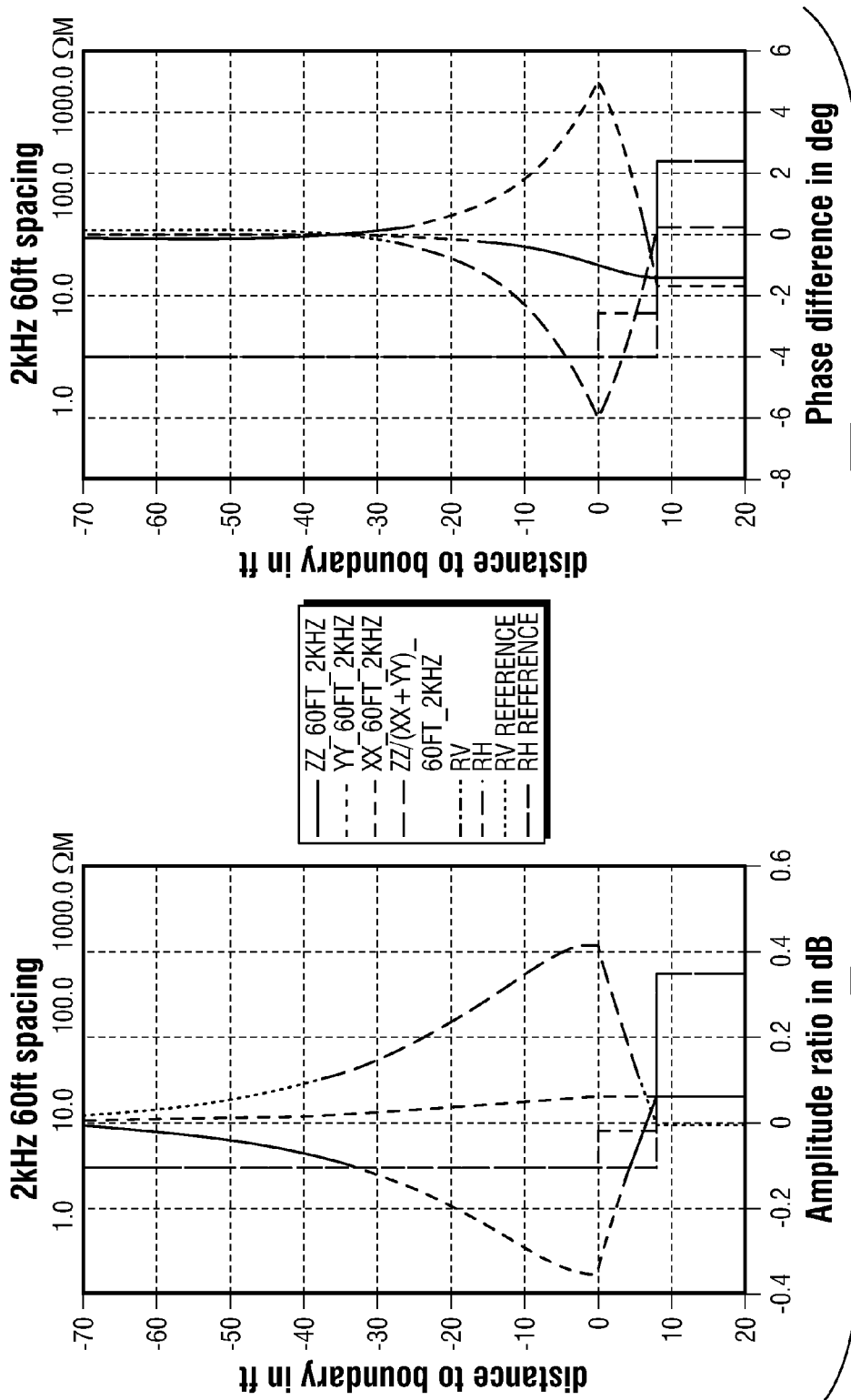
FIG. 37 is a graphical representation illustrating examples of measurements output by the logging system representing the determination of subterranean features, such as the proximity and presence of a dirty sand position, according to an embodiment of the present invention.
Figure 37B:
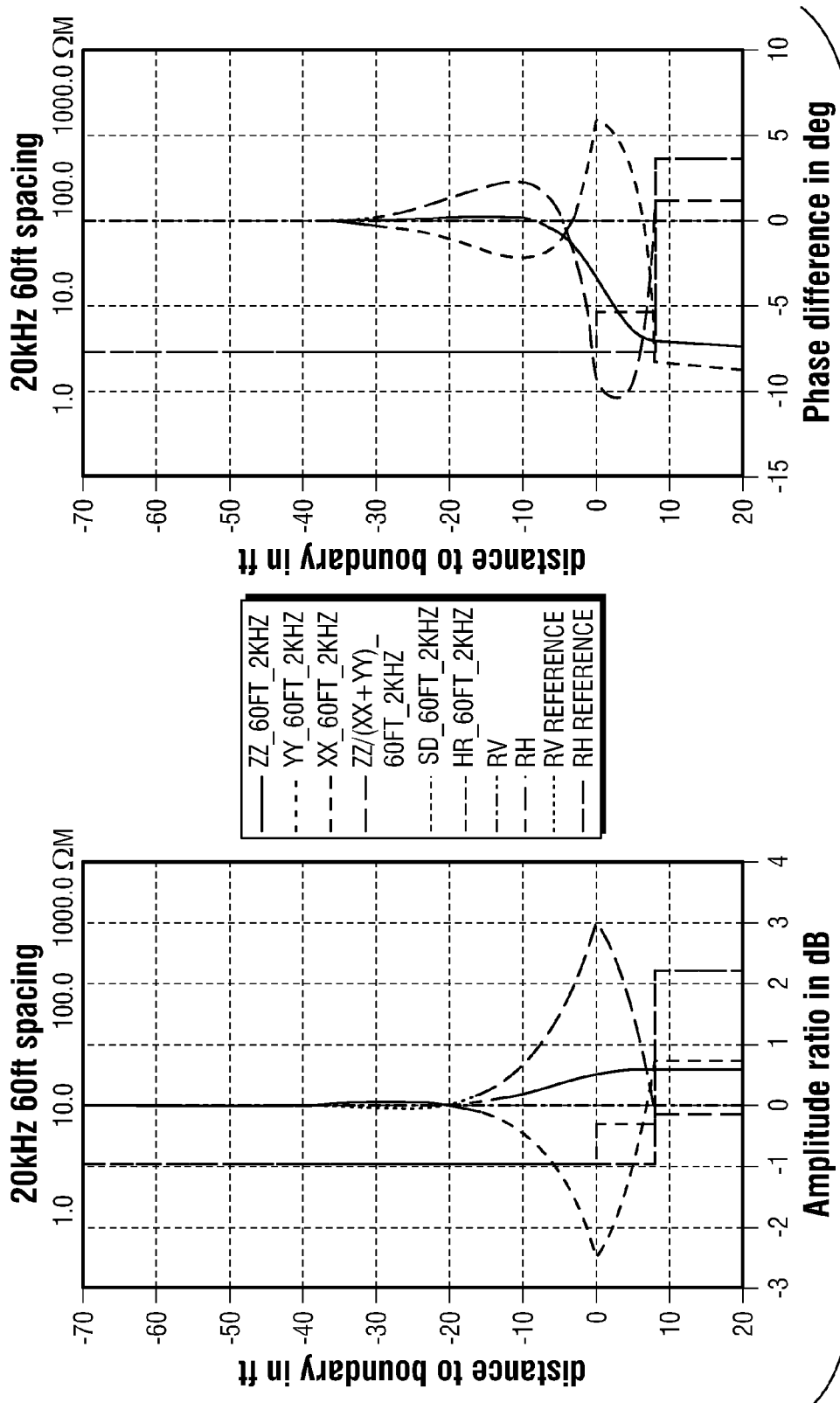
Figure 38A:
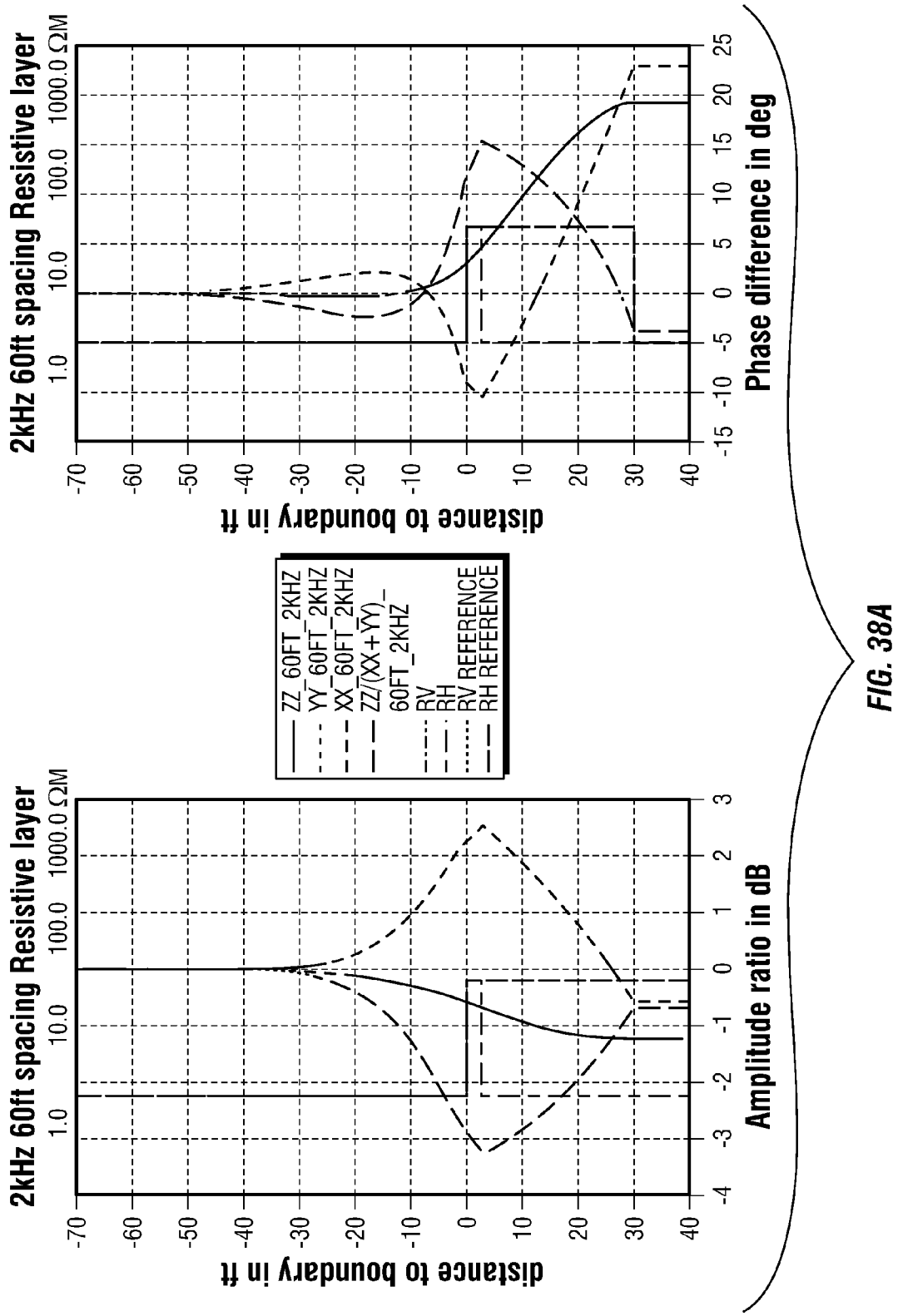
FIG. 38 is a graphical representation illustrating examples of measurements output by the logging system representing estimations of layer thickness, according to an embodiment of the present invention.
Figure 38B:
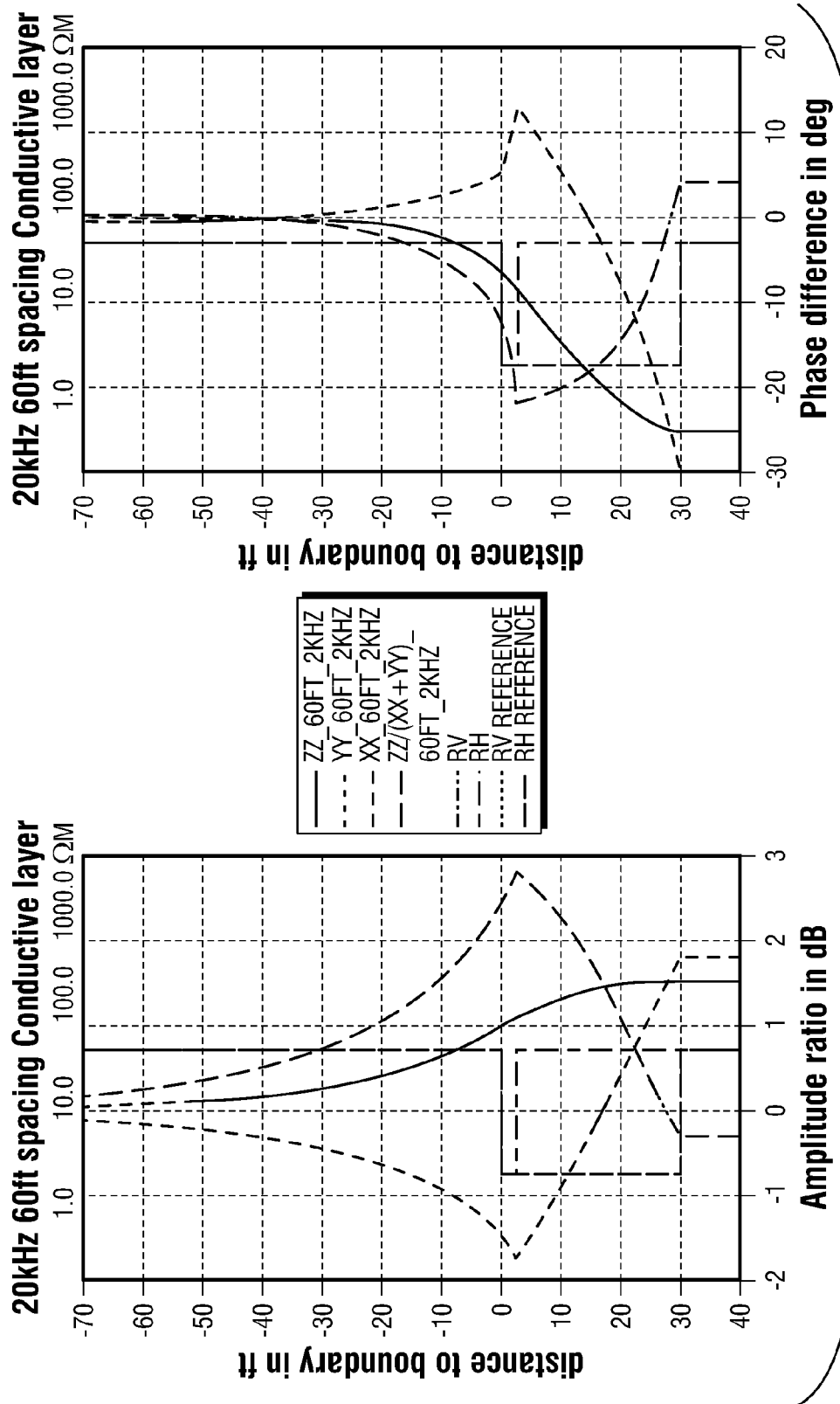

The look-ahead capabilities of the logging system also can be used to determine dirty sand proximity for optimum coring, as illustrated by the graphical results provided in FIG. 37. In this example, the look-ahead capabilities of logging while drilling system 44 are used to determine the proximity and presence of a dirty sand position just above a main reservoir so that coring can take place in the dirty sand layer or section. In the examples represented by the graphs of FIG. 37, the 2 kHz and 20 kHz examples both illustrate sensitivity to the middle layer but with a somewhat reduced look-ahead capability, e.g. less than one half the spacing. As illustrated in the graphical representations of FIG. 38, however, the layer thickness can be estimated with stronger effect for a conductive layer as opposed to a resistive layer. The numerous graphical representations illustrated and described above are provided to facilitate an understanding of the logging technique disclosed herein. However, the control system 52 also can be designed to display the various graphs and other information on display 56 to facilitate analysis of a wide variety of subterranean features and characteristics based on data obtained via logging system 44 and overall system 40.

Figure 39:
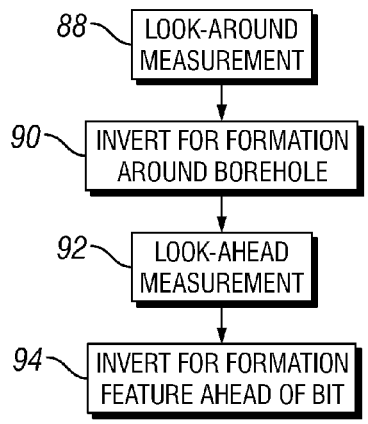
FIG. 39 is a flow chart representing one example of a procedure for acquiring data with the logging system in which a direct inversion is utilized, according to an embodiment of the present invention.
Figure 40:
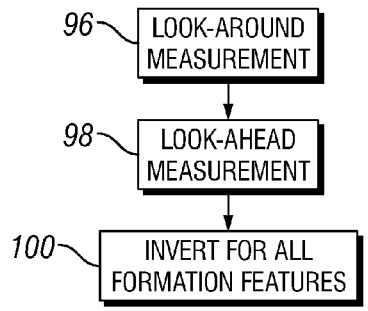
FIG. 40 is another flow chart representing an example of a procedure for acquiring data with the logging system in which a direct inversion is utilized, according to an embodiment of the present invention.

Referring generally to FIGS. 39 and 40, flow charts are provided to illustrate the process of determining a formation property ahead of the drill bit 66 through inversion. In the first example of FIG. 39, a look-around measurement is initially performed, as represented by block 88. The data is inverted for the formation around the borehole, e.g. wellbore 42, as represented by block 90. A look-ahead measurement can then be performed, as represented by block 92. The data obtained is inverted for a formation feature ahead of the drill bit 66, as represented by block 94.

Another example is illustrated by the flowchart of FIG. 40 in which a look-around measurement is initially performed, as represented by block 96. A look-ahead measurement also is performed, as represented by block 98. The measurement data obtained is inverted for all formation features, as represented by block 100. It should be noted that because the inversions are based on the volumetric effect of the formation on the measurements, the look-ahead capability and computations require knowledge and inversion of the formation structure and resistivity around the bottom hole assembly 46. Antennas having shorter T-R spacing and higher frequency (reduced depth of investigation) can be used to acquire data and to determine the formation around the bottom hole assembly while not being sensitive to the look-ahead features. As illustrated by the flowchart, a direct inversion can be used to invert for all depths of investigation at the same time.

Figure 41:
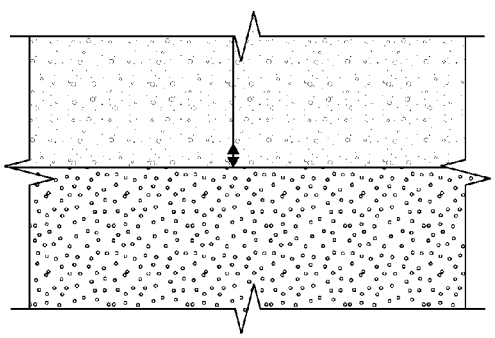
FIG. 41 is a schematic illustration of an example in which a look-ahead inversion is used by the logging system to determine information related to the subterranean environment, according to an embodiment of the present invention.
Figure 42:
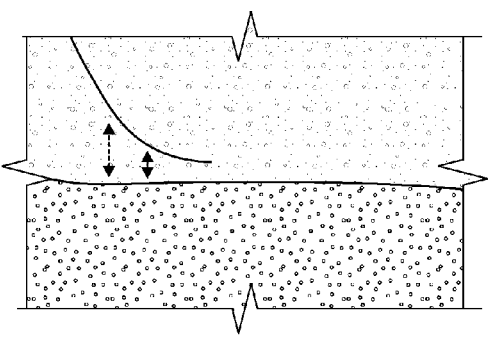
FIG. 42 is a schematic illustration of another example in which a look-ahead inversion is used by the logging system to determine information related to the subterranean environment, according to an alternate embodiment of the present invention.
Figure 43:
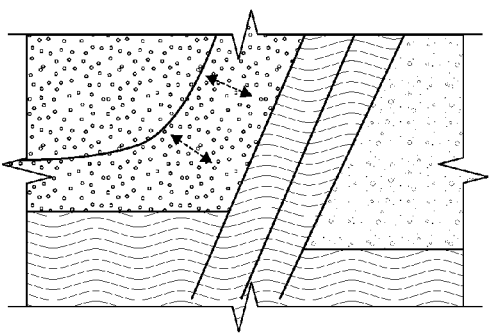
FIG. 43 is a schematic illustration of another example in which a look-ahead inversion is used by the logging system to determine information related to the subterranean environment, according to an alternate embodiment of the present invention.

With reference to FIGS. 41-43, the look-ahead inversion can be divided into two categories. As represented by FIG. 41, one category comprises a 1D inversion. This approach is useful for wide-ranging applications, although the approach is very suitable for vertical well applications where the formation structure dip is nearly horizontal. By way of example, this inversion technique can be used in applications involving pore-pressure detection, drilling management, geostopping, and landing into a reservoir. A second category comprises a 2D/3D inversion as represented by FIGS. 42 and 43. Applications utilizing this inversion technique tend to be used in horizontal wells. For example, the technique is useful for geosteering and in detecting features ahead of the drill bit, such as an incoming fault or shale that is to be avoided.

The system and methodology described herein can be used to improve the accumulation and analysis of data related to subterranean regions, such as regions ahead of or surrounding a wellbore. The system and methodology can be employed to acquire data at multiple depths of investigation in desired directions to improve the understanding of a given well formation or other subterranean region. As described, the transmitter antennas and the receiver antennas can be selected and oriented to enable radial sensitivity and/or sensitivity ahead of the logging system. For example, the system can provide sensitivity ahead of the drill bit 66. The location and spacing of the transmitting antenna and receiving antenna can be selected according to both the parameters of a given application and the environment in which the logging operation is performed to facilitate detection of features ahead of the drill bit/bottom hole assembly.

Accordingly, although only a few embodiments of the present invention have been described in detail above, those of ordinary skill in the art will readily appreciate that many modifications are possible without materially departing from the teachings of this invention. Such modifications are intended to be included within the scope of this invention as defined in the claims.

What is claimed is:

1. A logging while drilling system to detect and measure one or more subterranean features and/or characteristics ahead of or around a drill bit, comprising:
   a transmitter module having a transmitter longitudinal axis and a transmitter antenna located on or near the drill bit, the transmitter module having connectors on both ends and being removeably connected into a bottomhole assembly;
   a receiver module having a receiver longitudinal axis and a receiver antenna, the receiver module, the receiver module having connectors on both ends and being removeably connected into the bottom hole assembly and being positioned at a separate location along the logging while drilling system relative to the transmitter module such that the transmitter antenna and the receiver antenna are spaced apart axially along the bottom hole assembly, wherein at least one of the transmitter antenna and the receiver antenna is a directional antenna, and wherein the spacing between the transmitter antenna and the receiver antenna is selected to be equal to or greater than the thickness of at least one reservoir bed being investigated by the logging while drilling system; and
   a control system having a processor capable of:
   processing look-ahead data and/or look-around data received from the logging while drilling system;
   relating the look-ahead data or the look-around data to an electromagnetic coupling tensor;
   transforming one or more components of the electromagnetic coupling tensor to a corresponding formation parameter; and
   outputting the look-ahead data and/or the look-around data and/or corresponding formation parameters to an output device.

2. The logging while drilling system of claim 1, wherein the transmitter and receiver antennas are both directional antennas having dipole moments that intersect their respective module longitudinal axes at substantially equal angles.

3. The logging while drilling system of claim 1, wherein the transmitter and receiver antennas have dipole moments that intersect their respective module longitudinal axes at unequal angles.

4. The logging while drilling system of claim 1, wherein the transmitter antenna and the receiver antenna comprise magnetic dipole antennas, electric dipole antennas, or a combination of electric and magnetic dipole antennas.

5. The logging while drilling system of claim 1, further comprising one or more downhole tools located between the transmitter module and the receiver module.

6. The logging while drilling system of claim 1, wherein the locations of the transmitter and receiver antennas have a spacing based on a desired look-a head distance or a desired look-around distance.

7. The logging while drilling system of claim 1, wherein the measurements of the one or more subterranean features and/or characteristics ahead of or around the drill bit are made using the transmitter and receiver antenna at three or more frequencies per decade.

8. The logging while drilling system of claim 1, wherein the measurements of the one or more subterranean features and/or characteristics ahead of or around the drill bit are made at frequencies that satisfy $|k|\cdot L \in [0.1;10]$, wherein k represents a propagation coefficient calculated as $k^2 = \epsilon\mu\omega^2 + i\sigma\mu\omega$, wherein $\epsilon$ represents electromagnetic permittivity, $\mu$ represents electromagnetic permeability, $\sigma$ represents conductivity, and $\omega$ represents angular frequency.

9. A method to detect and measure one or more subterranean features and/or characteristics ahead of or around a drill bit, comprising:
   providing a logging while drilling system that has: a transmitter module having a transmitter longitudinal axis and a transmitter antenna located on or near the drill bit, the transmitter module having connectors on both ends and being removeably connected into a bottom hole assembly, a receiver module having a receiver longitudinal axis and a receiver antenna, the receiver module having connectors on both ends and being removeably connected into the bottomhole assembly and being positioned at a separate location along the logging while drilling system relative to the transmitter module, wherein at least one of the transmitter antenna and the receiver antenna is a directional antenna, and a control system having a processor, wherein the transmitter antenna and the receiver antenna are spaced apart axially along the bottomhole assembly, the spacing being selected to be equal to or greater than the thickness of at least one reservoir bed being investigated by the logging while drilling system;
   processing look-ahead data and/or look-around data received from the logging while drilling system;
   relating the look-ahead data or the look-around data to an electromagnetic coupling tensor;
   transforming one or more components of the electromagnetic coupling tensor to a corresponding formation parameter; and
   outputting the look-ahead data and/or the look-around data and/or corresponding formation parameter to an output device.

10. The method of claim 9, further comprising:
    comparing a measured response to a computed expected response based on a particular formation model; and
    determining the presence and position of one or more resistivity contrasts ahead of or around the drill bit.

11. The method of claim 10, further comprising using the presence and position of the one or more resistivity contrasts for geosteering, bed boundary detection, landing a wellbore, pore pressure detection, positioning for core sampling, geostopping, and drilling management.

12. The method of claim 11, further comprising determining a distance between a reference point and one or more bed boundaries.

13. The method of claim 10, wherein the comparing includes computing a difference between the measured response and the computed expected response.

14. The method of claim 10, wherein the measured response is related to a component of the electromagnetic coupling tensor or a combination of components of the electromagnetic coupling tensor.

15. The method of claim 10, wherein the computed expected response is related to a component of the electromagnetic coupling tensor or a combination of components of the electromagnetic coupling tensor.

16. The method of claim 9, wherein the outputting includes displaying on a screen and/or plotting on a tangible medium.

17. The method of claim 9, further comprising determining formation properties selected from the group consisting of: a pore pressure, a distance to a bed boundary, a bed thickness, a formation type, a conductivity tensor, a dip angle, a dip azimuth, and a fault detection.

18. The method of claim 17, further comprising using the determined formation property for geosteering, bed boundary detection, landing a wellbore, pore pressure detection, positioning for core sampling, geostopping, and drilling management.

19. The method of claim 9, further comprising calibrating the transmitter antenna and the receiver antenna.

20. The method of claim 9, further comprising determining a look-ahead sensitivity to two-step changes in resistivity with respect to spacing attenuation and phase shift.

21. The method of claim 9, further comprising determining a look-ahead range.

22. The method of claim 9, further comprising discriminating between a step change in resistivity ahead of the drill bit and a gradual ramp increase or decrease ahead of the drill bit.

23. The method of claim 9, further comprising determining a look-ahead sensitivity to a resistivity profile with respect to an anisotropic formation and a non-zero structural dip.

24. The method of claim 9, further comprising determining look-ahead capabilities and look-around capabilities of the logging while drilling system as a function of structural dip.

25. The method of claim 24, further comprising determining dirty sand proximity using the look-ahead capability of the logging while drilling system.

26. The method of claim 9, wherein the processing further comprises performing a 1D, 2D, or 3D inversion on the look-ahead data.

27. The method of claim 9, wherein the measurements of the one or more subterranean features and/or characteristics ahead of or around the drill bit are made using the transmitter and receiver antenna at three or more frequencies per decade.

28. The method of claim 9, wherein the measurements of the one or more subterranean features and/or characteristics ahead of or around the drill bit are made at frequencies that satisfy $|k|.L \in [0.1;10]$, wherein k represents a propagation coefficient calculated as $k^2 = \epsilon\mu\omega^2 + i\sigma\mu\omega$, wherein $\epsilon$ represents electromagnetic permittivity, $\mu$ represents electromagnetic permeability, $\sigma$ represents conductivity, and $\omega$ represents angular frequency.

29. A method to detect and measure one or more subterranean features and/or characteristics ahead of or around a drill bit, comprising:
providing a logging while drilling system that has: a transmitter module having a transmitter longitudinal axis and a transmitter antenna located on or near the drill bit, the transmitter module having connectors on both ends and being removeably connected into a bottom hole assembly, a receiver module having a receiver longitudinal axis and a receiver antenna, the receiver module having connectors on both ends and being removeably connected into the bottomhole assembly and being positioned at a separate location along the logging while drilling system relative to the transmitter module, wherein at least one of the transmitter antenna and the receiver antenna is a directional antenna, and a control system having a processor;
processing look-ahead data and/or look-around data received from the logging while drilling system;
relating the look-ahead data or the look-around data to an electromagnetic coupling tensor;
transforming one or more components of the electromagnetic coupling tensor to a corresponding formation parameter;
outputting the look-ahead data and/or the look-around data and/or corresponding formation parameter to an output device; and
determining formation properties selected from the group consisting of: a pore pressure, a distance to a bed boundary, a bed thickness, a formation type, a conductivity tensor, a dip angle, a dip azimuth, and a fault detection, wherein the determined formation property is used for geosteering, bed boundary detection, landing a wellbore, pore pressure detection, positioning for core sampling, geostopping, and drilling management.

* * * * *